US011001834B2

(12) United States Patent
McEwan et al.

(10) Patent No.: US 11,001,834 B2
(45) Date of Patent: May 11, 2021

(54) HIGH-MOLECULAR WEIGHT DNA SAMPLE TRACKING TAGS FOR NEXT GENERATION SEQUENCING

(71) Applicant: Kapa Biosystems, Inc., Wilmington, MA (US)

(72) Inventors: Paul McEwan, Western Cape (ZA); Martin Ranik, Cape Town (ZA); Eric van der Walt, Western Cape (ZA)

(73) Assignee: KAPA BIOSYSTEMS, INC., Wilmington, MA (US)

( * ) Notice: Subject to any disclaimer, the term of this patent is extended or adjusted under 35 U.S.C. 154(b) by 0 days.

(21) Appl. No.: 15/279,170

(22) Filed: Sep. 28, 2016

(65) Prior Publication Data

US 2017/0088832 A1    Mar. 30, 2017

Related U.S. Application Data

(60) Provisional application No. 62/234,630, filed on Sep. 29, 2015, provisional application No. 62/335,364, filed on May 12, 2016.

(51) Int. Cl.
*C12N 15/10* (2006.01)
*C12Q 1/6806* (2018.01)
*C12Q 1/6874* (2018.01)

(52) U.S. Cl.
CPC ....... *C12N 15/1065* (2013.01); *C12Q 1/6806* (2013.01); *C12Q 1/6874* (2013.01)

(58) Field of Classification Search
CPC .................................................. C12N 15/1065
See application file for complete search history.

(56) References Cited

U.S. PATENT DOCUMENTS

| 5,648,245 | A | 7/1997 | Fire et al. |
| 6,329,150 | B1 | 12/2001 | Lizardi et al. |
| 2012/0046175 | A1 | 2/2012 | Rodesch et al. |
| 2013/0072390 | A1 | 3/2013 | Wang et al. |

FOREIGN PATENT DOCUMENTS

| EP | 1 316 618 A2 | 6/2003 |
| WO | WO 90/14441 A1 | 11/1990 |
| WO | WO 2014/128453 A1 | 8/2014 |

OTHER PUBLICATIONS

Molecular Biology Reagents/Protocols 1992, United States Biochemical Corporation, 1991, Cleveland, Ohio, pp. 381-386.*
Altschul et al., "Basic local alignment search tool", J. Mol. Biol., vol. 215, No. 3, p. 403-410, (1990).
Altschul, et al., "Gapped BLAST and PSI-BLAST: a new generation of protein database search programs", Nucleic Acids Research, vol. 25, No. 17, p. 3389-3402, (1997).
Holliger, P., et al. ""Diabodies": Small bivalent and bispecific antibody fragments", Proc. Natl. Acad. Sci. USA, vol. 90, p. 6444-6448, (1993).
Myers, et al., "Optimal alignments in linear space", CABIOS, vol. 4, No. 1, p. 11-17 (1988).
Perkel, JM, Next-Gen DNA Sequencing: 2015 Update posted at Biocompare on Feb. 24, 2015; http://www.biocompare.com/Editorial-Articlest/171872-Next-Gen-DNA-Sequeneing-2015-Update.
Poljak, R. J., et al. "Productoin and structure of diabodies" 2: 1 121-1123, (1994).
V.I. Levenshtein, "Binary Codes Capable of Correcting Deletions, Insertions, and Reversals", Soviet Physics Doklady 10 (8): 707-710, Feb. 1966.
Srirangan Sampath, Ph.D., FACMG et al. "Use of Spike-ins for Sample Tracking in Agilent Array CGH", Agilent Technologies, Inc. (2016) p. 1-8.
Michael A. Quail et al., "SASI-Seq Sample assurance Spike-Ins, and highly differentiating 384 barcoding for Illumna sequencing", BMC Genomics (2014), 15:110, p. 1-12.
BI00 Scientific, Next-Gen Sequencing, NEXTflex™ Spike-In Controls, Product Sheet, © 2017.
Altschul and Gish, "Local Alignment Statistics," Methods Enzymol. 266:460-480 (1996).

* cited by examiner

*Primary Examiner* — James Martinelli
(74) *Attorney, Agent, or Firm* — Eric Grant Lee

(57) ABSTRACT

The present invention provides synthetic nucleic acid molecule tags that can be added into samples for identification and tracking. Among other things, the present invention provides synthetic, high-molecular weight concatemers, which can be combined with samples to yield hundreds of millions of unique identifiers. Examples applications for which the synthetic nucleic acid molecule tags can be used, include industrial, research and clinical applications.

28 Claims, 14 Drawing Sheets

Specification includes a Sequence Listing.

```
--  --------AGGCCGACAATA  GGCACGAGCATAGAAGTTAGTA  CGTAGCGTCGTCGCATA
--  ----------------------  ---------------AGTTAGTA  CGTAGCGTGGTCGCATA
--  ----------------------  ----------------------  -----------------
--  -----------------ATA  GGCACGAGCATAGAAGTTAGTA  CGTAGCGTCGTCGCATA
--  --------------ACAATA  GGCACGAGCATAGAAGTTAGTA  CGTAGCGTCGTCACATA
AG  ATGCACAAGGCCGACAATA  GGCACGAGCATAGAAGTTAGTA  CGTAGCGTCGTCGCATA
--  ----------------------  ----------------------  -----------------
--  ----------------------  ----------------------  -----------------
--  --------GGCCGACAATA  GGCACGAGCATAGAAGTTAGTA  CGTAGCGTCGTCGCATA
--  ----CACAAGGCCGACAATA  GGCACGAGCATAGAAGTTAGTA  CGTAGCGTCGTCGCATA
AG  ATGCACAAGGCCGACAATA  GGCACGAGCATAGATGTTAGTC  CGTTTCGTCGCCGCATA
AG  ATGCACAAGGCCGACAATA  GGCACGAGCATAGAAGTTAGTA  CGTAGCGTGGTCGCATA
    ATGCACAAGGCCGACAATA  GGCACGAGCATAGAAGTTAGTA  CGTAGCGTCGTCGCATA
AG  ATGCACAAGGCCGACAATA  GGCACGAGCATAGAAGGTAGTA  CGTAGCGTCGTCGCATA
AG  ATGCACAAGGCCGACAATA  GGCACGAGCATAGAAGTTAGTA  CGTAGCGTCGTCGCATA
AG  ATGCACAAGGCCGACAATA  GGCACGAGCATAGAAGTTAGTA  CGTAGCGTCGTCGCATA
-G  ATGCACAAGGCCGACAATA  GGCACGAGCATAGAAGTTAGTA  CGTAGCGTCGTCGCATA
-G  ATGCACAAGGCCGACAATA  GGCACGAGCATAGAAGTTAGTA  CGTAGCGTCGTCGCATA
AG  ATGCACAAGGCCGACAATA  GGCACGAGCATAGAAGTTAGTA  CGTAGCGTCGTCGCATA
AG  ATGCACAAGGCCGACAATA  GGCACGAGCATAGAAGTTAGTA  CGTAGCGTCGTCGCATA
    * * * * * * * * * * * * * * * * *  * * * * * * * * * * * * *  * * *    * * *   *  * * * * * *
AG  CCGCTCAAGTCCGACAATA  AGCACGAGCATAGAAGCTAGTC  ACTATCGTCGTCGCACT
AG  ATGCACAAGGC--------  ----------------------  -----------------
CG  ATGCACAAGGCCGACAATA  GGCACGCGCATAGAAGTTAGTA  CGTAGCGTCGTCGCATA
AG  ATGCACAAGGCCGACAATA  GGCACGAGCATAGAAGTGAGTA  CGTAGCGTCGTCGCATA
AG  ATGCACAAGGCCGACAATA  GGCACGAGCATAGAAGTTAGTA  CGTAGCGTCGTCGCATA
AG  ATGCACAAGGCCGACAATA  GGCACGAGCATAGAAGTTAGTA  CGTAGCGTCGTCGCATA
AG  ATGCACAAGGCCGACAATA  GG--------------------  -----------------
AG  ATGCACAAGGCCGACAATA  GGCACGAGC-------------  -----------------
AG  ATGCACAAGGCCGACAAT-  ----------------------  -----------------
AG  ATGCACAAGGCCGACAATA  GGCACGAGCATAGAAGATAGTA  CGTAGCGTCGTCGCATA
 *   ** ****  *
AG  ATGAACAAGACCTACAATA  GGCACTAGCATAGGACTTAGTC  CGCCGCGTCGTCCCATA
--  ----------------------  ----------------------  -----------------
AG  ATGCACAAGGCCGACAACA  GG--------------------  -----------------
AG  ATGCACAAGGCCGACAATA  GGCACGAGCAT-----------  -----------------
AG  ATGCACAAGGCCGAC----  ----------------------  -----------------
AG  ATGCACAAGGCCGACAACA  GGCACGCATAGAAGTTAGT---  -----------------
--  ----------------------  ----------------------  -----------------
--  ----------------------  ----------------------  -----------------
AG  CTGCACAAGGCCGACAATA  GGCACGAG--------------  -----------------
```

HIGH-MOLECULAR WEIGHT DNA SAMPLE TRACKING TAGS FOR NEXT GENERATION SEQUENCING

CROSS REFERENCE TO RELATED APPLICATIONS

This application is based on, claims the benefit of, and incorporates herein by reference the entire contents of: U. S. Provisional Application Ser. No. 62/234,630, filed on 29 Sep., 2015, and U. S. Provisional Application Ser. No. 62/335,364, filed on 12 May, 2016.

STATEMENT REGARDING FEDERALLY SPONSORED RESEARCH

Not applicable.

INCORPORATION OF SEQUENCE LISTING

The contents of the text file named "RMSI-006/001US_SeqList.txt," which was created on Aug. 16, 2017 and is 29 KB in size, are hereby incorporated by reference in their entirety.

BACKGROUND

The ongoing revolution in DNA sequencing technologies is transforming medical, agricultural, and forensic science, creating both an expectation and a demand that enormous numbers of samples be processed in limited time. A recent technology review describes current projects, such as the Roadmap Epigenomics Consortium—which uses high-throughput DNA sequencing technologies to describe the epigenomes of human cell types—studies that analyze the single-cell transcriptomics of the mouse brain, and efforts to document the metagenomics of the New York City subway, as "previously unimaginable". (Perkel, J M, *Next-Gen DNA Sequencing: 2015 Update* posted at Biocompare on 24 Feb. 2015).

SUMMARY

The present disclosure provides certain insights relating, among other things, to technologies for tracking nucleic acid samples. In one aspect, the present disclosure identifies the source of a problem associated with many existing nucleic acid management and/or analysis systems. For example, the present disclosure encompasses the insight that many high-throughput facilities such as clinical and core labs run the risk of confusing or cross-contaminating samples. In many scenarios, these types of errors are undetectable by standard quality control workflows, with potentially grave consequences, particularly in clinical settings (e.g., somatic mutation detection), errors in DNA analysis in forensics testing, and the like. The present disclosure therefore appreciates that detection of such errors is an important, unmet need in sample handling and analysis.

Among other things, the present invention provides high-molecular weight synthetic nucleic acid tags useful, for example, to confirm sample identity and/or to detect sample cross-contamination.

In some embodiments, provided tags comprise or consist of DNA. In some embodiments, provided tags comprise or consist of double-stranded DNA ("dsDNA"). In some embodiments, provided tags (e.g., dsDNA tags) have a nucleotide sequence that comprises or consists of repeats of a sequence element, wherein the sequence element comprises or consists of a tag sequence and a universal sequence, as described herein. In some embodiments, provided tags may be "spiked in" or added to a sample at a particular ratio of tag mass to sample mass.

In some embodiments, a provided tag may be added to ("spiked in"), for example, in a defined amount (weight and/or volume), to a nucleic acid sample under analysis (e.g., being subjected to a nucleic acid sequencing or other processing technology).

In some embodiments, it is possible to detect and discriminate between provided tags using technologies such as probe-based qPCR.

In some embodiments, provided tags may be used as stand-alone DNA markers (e.g., for tagging physical objects). In some embodiments, the tagged physical objects are not nucleic acid molecules.

In some such embodiments, a provided tag may be added to a plurality of samples undergoing a particular analysis. In some embodiments, a provided tag may be added to all samples undergoing a particular analysis.

In accordance with some embodiments of the present disclosure, a tag as described herein may be added to samples at a pre-determined mass ratio of tag to sample DNA (e.g., 0.1%).

In some embodiments, tags may be added to samples undergoing (and therefore containing components and/or reagents for) sequencing analysis (e.g., DNA sequencing analysis). In some embodiments, tags may be added to samples undergoing high-throughput sequencing analysis. In some embodiments, tags may be added to samples undergoing a so-called "next-generation sequencing" ("NGS") analysis.

In some embodiments, tags may be added to a set of samples that are related to one another in that they include sample nucleic acid (e.g., target DNA or RNA to be sequenced) from a single source (e.g., a single genome, single transcriptome, etc.) or from a set of related sources. In some embodiments, a set of samples is a "library".

In some embodiments, tags as described herein may be added to samples at the point of their collection (e.g., to crude samples, for example of particular organismal or cellular nucleic acid), further decreasing the chance of sample cross-contamination. In accordance with the present disclosure, in some embodiments, certain features of provided tags (e.g., their synthetic design, the inclusion of random and/or universal sequence elements, their repetitive structure, etc.) facilitate improved, unambiguous tag-derived sequence identification during data analysis. The large edit distance between unique tags can allow clear identification of sample cross-contamination, and can be used to assay technical parameters such as indexing adapter barcode cross-talk. In some embodiments, the repetitive tag structure allows use of provided tags in targeted sequencing applications such as hybrid capture and amplicon sequencing. Combinatorial sample tagging would allow the generation of many unique sample tag combinations using a relatively small set of unique tag sequences. Among other things, provided sample tagging methodologies provide simple and robust means for ensuring sample security (particularly for high-throughput, e.g., NGS samples) and process control from sample collection to sequence analysis.

In some embodiments, the present invention provides a synthetic nucleic acid tag whose nucleic acid sequence may have a plurality of repeating units of structure A-B—C, and has an overall structure represented by the following formula: X-[A-B—C]$_n$—Y. In one embodiment, n is at least two and each of A, B, and C has a defined length of 2 or more residues.

In some embodiments, a tag having a formula according to the formula: X-[A-B—C]$_n$—Y has sequences of each of A and C, which sequences have at least one primer landing pad sequence element in that a primer hybridized thereto can be extended, and further wherein A and C have nucleotide sequences that are compatible with one another in that oppositely directed primers can simultaneously hybridize to both so that an amplification product is generated by extension of the hybridized primers.

In some embodiments, at least B has a sequence that does not hybridize with any sequence found in a relevant sample for analysis, wherein B has a length sufficient to ensure an edit distance of at least two between individual B regions in the tag.

In some embodiments, a tag having a formula according to the formula: X-[A-B—C]$_n$—Y, has X optionally present or absent and, if present may consist of or comprise one or more instances of —C—, or otherwise may consist of or comprise another element. In some embodiments, Y is optionally present or absent and, if present, may consist of or comprise one or more instances of -A-, or otherwise may consist of or comprise another element.

In some embodiments, the present invention provides for a sequencing sample comprising DNA and at least one synthetic nucleic acid tag, wherein A and C are each at least 2 nucleic acids in length, and are the same or different lengths; and wherein B comprises at least 2 nucleic acids, and wherein the plurality of repeating units is at least two.

In some embodiments, the present invention provides for a set of samples for sequence analysis, wherein each sample contains at least one synthetic nucleic acid tag whose nucleotide sequence comprises a plurality of repeating units according to the formula A-B—C, wherein A and C are each at least 8 nucleic acids in length, and are the same or different lengths; and wherein B comprises at least 8 nucleic acids.

In some embodiments, the tag comprises a nucleic acid molecule that is double stranded.

In some embodiments, each of the length of A and the length of C is at least at least 2 nucleotides. In some embodiments, the length of B is at least 2 nucleotides.

In some embodiments, the number of repeating units per molecule is at least two.

In some embodiments, the present invention provides kits. In some embodiments, the kit includes a plurality of nucleic acid molecule tags, each of which has a nucleic acid sequence represented by the formula: [A-B—C]$_n$, wherein n is at least two, wherein each of A, B, and C has a defined length of 2 or more residues.

In some embodiments the kit has different tags or sets of tags. In some embodiments, the different tags in the kit are structurally related to one another in that: each tag has an identical A sequence element; each tag has an identical C sequence element; and each tag has a B sequence element that differs from that of the other tags in the kit.

In some embodiments, the present invention provides a sample collection tube that includes one or more tags as described herein.

In some embodiments, the nucleic acid molecule tags are double-stranded DNA.

In some embodiments, the length of each of A and C is at least 2 nucleotides. In some embodiments, the length of B is at least 2 nucleotides.

In some embodiments, the number of repeats within a tag is at least 2.

In some embodiments, the present invention provides for a method of tagging a sample. In some embodiments, the method includes contacting the sample with at least one tag as described herein, under conditions such that the tag and the sample are contained in the same vessel.

In some embodiments, the sample is a crude sample. In some embodiments, the sample is separated into one or more parts (subsample).

In some embodiments, the sample is a purified sample. In some embodiments, the purified sample is isolated DNA.

In some embodiments, the contacting of the sample with the tag occurs at the time the sample is collected. In some embodiments, the contacting occurs prior to sample purification. In some embodiments, the contacting occurs prior to DNA extraction. In some embodiments, the contacting occurs after DNA extraction. In some embodiments, the contacting occurs after DNA purification.

In some embodiments, the contacting occurs in a collection vessel containing the sample. In some embodiments, the contacting occurs in a well-plate/container, which container will be used to amplify and analyze samples. In some embodiments, the contacting occurs before the sample is separated into more than one portion. In some embodiments, the contacting occurs after the sample is separated into more than one portion.

In some embodiments, the contacting comprises adding the tag to the sample at least about 0.0001 percent to at least about 10 percent mass of tag, relative to the mass of the sample.

In another embodiment, the present disclosure provides a synthetic nucleic acid tag whose nucleic acid sequence includes a plurality of repeating units of a structure A-B—C. The synthetic nucleic acid tag has an overall structure represented by the formula: $X_i$-[A-B—C]$_n$—$Y_j$. The synthetic nucleic acid tag includes n repeats of the structure A-B—C, where n is at least two. In one aspect, each of A, B, and C is a nucleic acid having a defined length of at least two residues, the synthetic nucleic acid tag includes i repeats of X, and the synthetic nucleic acid tag includes j repeats of Y. In another aspect, X is at least one of C, another nucleic acid, and a nucleic acid modification, and Y is at least one of A, another nucleic acid, and a nucleic acid modification. In yet another aspect, i and j are integers independently selected from 0-100.

BRIEF DESCRIPTION OF THE DRAWING

FIG. 9 shows raw results of sequencing of an exemplary library. The alignment of raw reads from the library was mapped to the Tag 1 sequence. The sequences listed in the alignment, in order from top to bottom, are: SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141.

DEFINITIONS

Figure 1:
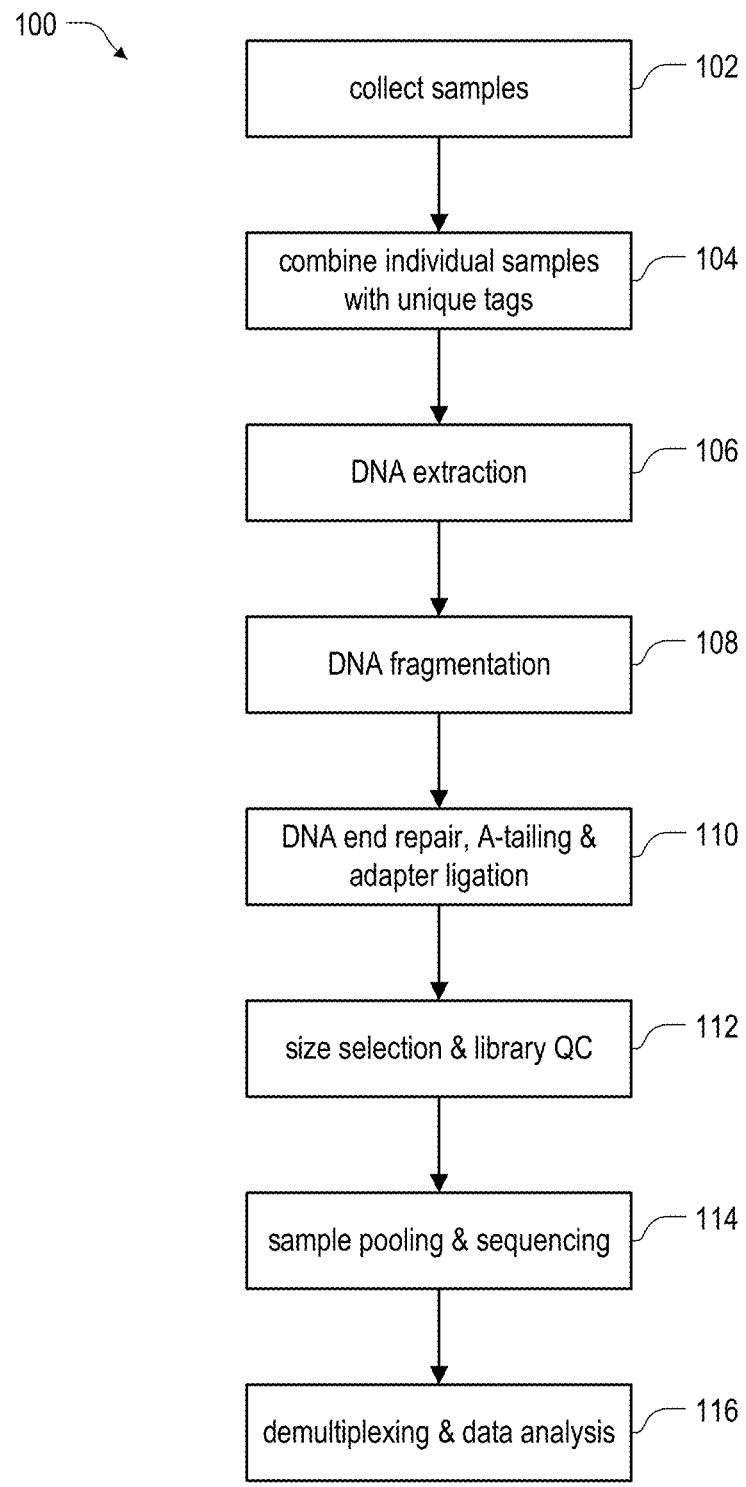
FIG. 1 is an example of a method of sample tracking using the high-molecular weight DNA tags according to the present disclosure.

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: Two events or entities are "associated" with one another, as that term is used herein, if the presence, level and/or form of one is correlated with that of the other. For example, a particular entity (e.g., polypeptide, genetic signature, metabolite, etc.) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Barcode: As used herein, the term "barcode" is meant to represent a particular nucleic acid molecule or sequence which serves as a machine readable identifier when mixed and/or added to a sample to be analyzed, (e.g., by nucleic acid sequencing analysis). In some embodiments, a bar code is used for identifying, tracking and/or confirming presence and/or absence of a particular sampl.

Biological Sample: As used herein, the term "biological sample" typically refers to a sample obtained or derived from a biological source (e.g., a tissue or organism or cell culture) of interest, as described herein. In some embodiments, a source of interest comprises or consists of an organism, such as an animal or human. In some embodiments, a biological sample is comprises or consists of biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; other body fluids, secretions, and/or excretions; and/or cells therefrom, etc. In some embodiments, a biological sample is comprises or consists of cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Carrier: As used herein, the term "carrier" refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

Cellular lysate: As used herein, the term "cellular lysate" or "cell lysate" refers to a fluid containing contents of one or more disrupted cells (i.e., cells whose membrane has been disrupted). In some embodiments, a cellular lysate includes both hydrophilic and hydrophobic cellular components. In some embodiments, a cellular lysate is a lysate of one or more cells selected from the group consisting of plant cells, microbial (e.g., bacterial or fungal) cells, animal cells (e.g., mammalian cells), human cells, and combinations thereof. In some embodiments, a cellular lysate is a lysate of one or more abnormal cells, such as cancer cells. In some embodiments, a cellular lysate is a crude lysate in that little or no purification is performed after disruption of the cells, which generates a "primary" lysate. In some embodiments, one or more isolation or purification steps is performed on the primary lysate. However, the term "lysate" refers to a preparation that includes multiple cellular components and not to pure preparations of any individual component.

Characteristic sequence: A "characteristic sequence" is a sequence that is found in all members of a family of polypeptides or nucleic acids, and therefore can be used by those of ordinary skill in the art to define members of the family.

Characteristic sequence element: As used herein, the phrase "characteristic sequence element" refers to a sequence element found in a polymer (e.g., in a polypeptide or nucleic acid) that represents a characteristic portion of that polymer. In some embodiments, presence of a characteristic sequence element correlates with presence or level of a particular activity or property of the polymer. In some embodiments, presence (or absence) of a characteristic sequence element defines a particular polymer as a member (or not a member) of a particular family or group of such polymers. A characteristic sequence element typically comprises or consists of at least two monomers (e.g., amino acids or nucleotides). In some embodiments, a characteristic sequence element includes at least 2, 3, 4, 5, 6, 7, 8, 9, 10, 11, 12, 13, 14, 15, 20, 25, 30, 35, 40, 45, 50, or more monomers (e.g., contiguously linked monomers). In some embodiments, a characteristic sequence element includes at least first and second stretches of contiguous monomers spaced apart by one or more spacer regions whose length may or may not vary across polymers that share the sequence element.

Compatible: The term "compatible" as used herein in the context compatible primers, refers to characteristics of, e.g., two primers within a reaction, that may be used in the same reaction without deleterious effects including, e.g., formation of primer dimers or binding to genomic or sample DNA sequences. Compatible primers may, for instance, possess similar characteristics including percent GC content, melting temperature and binding specificity, such that they have a greater likelihood of binding to the intended target than to each other.

Comprising: A composition or method described herein as "comprising" one or more named elements or steps is open-ended, meaning that the named elements or steps are essential, but other elements or steps may be added within the scope of the composition or method. It is to be understood that composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

Concatemer: As used herein, the term "concatemer" refers to a continuous nucleic acid molecule having a nucleic acid sequence comprising or consisting of repeats of a nucleic acid sequence that itself comprises or consists of a plurality of sequence elements linked to one another in series. In some embodiments, concatemers comprise copies of an entire genome. In some embodiments, concatemers comprise portions of a genome. In some embodiments, concatemers comprise one or more genes. In some embodiments, concatemers comprise one or more groups of synthetically generated nucleotides. In some embodiments, the linked series of sequence elements is separated, e.g., by short nucleotide sequences between each repeat. For example, a "concatemer" of sequence elements A, B, and C, might have a sequence represented by ABCABCABCABC or ACBAC-BACBACB or BCABCABCABCA or BACBACBACBAC or CABCABCAB or CBACBACBA or AABCAAB-CAABC, etc.

Degenerate Oligonucleotide: As used herein, the phrase "Degenerate oligonucleotide" refers to, in some embodiments, a mixture of oligonucleotides which are synthesized in a way that allows the incorporation of all four bases (i.e., A, T, G, and C) at specific oligonucleotide positions during the synthesis. For example, ACGCGACGNNNNNNTGGGACGA (SEQ ID NO: 108) is a degenerate sequence/degenerate oligonucleotide, where 'N' represents a degenerate nucleotide. Oligonucleotide synthesis with the exemplified sequence would produce $4^6$ oligonucleotides due to the presence of the 6 consecutive degenerate nucleotides and the use of 4 different bases (i.e., A, T, G, and C).

Designed: As used herein, the term "designed" refers to an agent (i) whose structure is or was selected by the hand of man; (ii) that is produced by a process requiring the hand of man; and/or (iii) that is distinct from natural substances and other known agents.

Determine: Those of ordinary skill in the art, reading the present specification, will appreciate that "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

Diagnostic information: As used herein, "diagnostic information" or "information for use in diagnosis" is information that is useful in determining whether a patient has a disease, disorder or condition and/or in classifying a disease, disorder or condition into a phenotypic category or any category having significance with regard to prognosis of a disease, disorder or condition, or likely response to treatment (either treatment in general or any particular treatment) of a disease, disorder or condition. Similarly, "diagnosis" refers to providing any type of diagnostic information, including, but not limited to, whether a subject is likely to have or develop a disease, disorder or condition, state, staging or characteristic of a disease, disorder or condition as manifested in the subject, information related to the nature or classification of a tumor, information related to prognosis and/or information useful in selecting an appropriate treatment. Selection of treatment may include the choice of a particular therapeutic agent or other treatment modality such as surgery, radiation, etc., a choice about whether to withhold or deliver therapy, a choice relating to dosing regimen (e.g., frequency or level of one or more doses of a particular therapeutic agent or combination of therapeutic agents), etc.

Domain: The term "domain" is used herein to refer to a section or portion of an entity. In some embodiments, a "domain" is associated with a particular structural and/or functional feature of the entity so that, when the domain is physically separated from the rest of its parent entity, it substantially or entirely retains the particular structural and/or functional feature. Alternatively or additionally, a domain may be or include a portion of an entity that, when separated from that (parent) entity and linked with a different (recipient) entity, substantially retains and/or imparts on the recipient entity one or more structural and/or functional features that characterized it in the parent entity. In some embodiments, a domain is a section or portion of a molecular structure (e.g., a small molecule, carbohydrate, a lipid, a nucleic acid, or a polypeptide). In some embodiments, a domain is a section of a polypeptide; in some such embodiments, a domain is characterized by a particular structural element (e.g., a particular amino acid sequence or sequence motif, α-helix character, β-sheet character, coiled-coil character, random coil character, etc.), and/or by a particular functional feature (e.g., binding activity, enzymatic activity, folding activity, signaling activity, etc.).

Edit distance: As used herein the phrase "edit distance" represents the number of nucleic acids by which e.g., a series of nucleic acids, nucleic acid molecule or tag (as tag is described herein) differs from another, and, refers to the number of, substitutions, insertions, deletions or other changes that would need to occur for one tag to be falsely identified as another tag (e.g., for two nucleic acid molecules, e.g., tag 1 and tag 2, with an edit distance of 8 nucleic acids, there would need to be seven altering events in the sequence of tag 1, wherein such altering events made tag 1 more similar to tag 2, in order for tag 1 to be identified as tag 2). In some embodiments, edit distance may be used interchangeably with "Levenshtein distance", as in Levenshtein, Vladimir I. (February 1966). "Binary codes capable of correcting deletions, insertions, and reversals". Soviet Physics Doklady 10 (8): 707-710.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Fragment: A "fragment" of a material or entity as described herein has a structure that includes a discrete portion of the whole, but lacks one or more moieties found in the whole. In some embodiments, a fragment consists of such a discrete portion. In some embodiments, a fragment consists of or comprises a characteristic structural element or moiety found in the whole. In some embodiments, a polymer fragment comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500 or more monomeric units (e.g., residues) as found in the whole polymer. In some embodiments, a polymer fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in the whole polymer. The whole material or entity may in some embodiments be referred to as the "parent" of the whole.

Gene: As used herein, the term "gene" refers to a DNA sequence in a chromosome that codes for a product (e.g., an RNA product and/or a polypeptide product). In some embodiments, a gene includes coding sequence (i.e., sequence that encodes a particular product); in some embodiments, a gene includes non-coding sequence. In some particular embodiments, a gene may include both coding (e.g., exonic) and non-coding (e.g., intronic) sequence. In some embodiments, a gene may include one or more regulatory elements that, for example, may control or impact one or more aspects of gene expression (e.g., cell-type-specific expression, inducible expression, etc.).

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

Genome: As used herein, the term "genome" refers to the total genetic information carried by an individual organism or cell, represented by the complete DNA sequences of its chromosomes.

Genome Profile: As used herein, the term "genome profile" refers to a representative subset of the total information contained within a genome. Typically, a genome profile contains genotypes at a particular set of polymorphic loci. In some embodiments, a genome profile may correlate with a particular feature, trait, or set thereof characteristic of, for example, a particular animal, line, breed, or crossbreed population.

Genomic DNA: As used herein the phrase "genomic DNA" refers to DNA that represents at least about one copy of the total genetic information contained within the genome of an organism. In some embodiments, genomic DNA is extracted from chromosomes. In some embodiments, genomic DNA is extrachromosomal genomic DNA that may be used e.g., for PCR amplification and/or sequencing analysis, etc.

Genotype: As used herein, the term "genotype" refers to the diploid combination of alleles at a given genetic locus, or set of related loci, in a given cell or organism. A homozygous subject carries two copies of the same allele and a heterozygous subject carries two distinct alleles. In the simplest case of a locus with two alleles "A" and "a", three genotypes can be formed: A/A, A/a, and a/a.

Genotyping: As used herein, the term "genotyping" refers to an experimental, computational, or observational protocol for distinguishing an individual's genotype at one or more well-defined loci. Those skilled in the art will be aware of a variety of technologies that can usefully and effectively perform genotyping. In some embodiments, genotyping involves direct detection of a nucleic acid or nucleic acid sequence. In some embodiments, genotyping involves indirect detection of a nucleic acid or nucleic acid sequence, for example through detection or analysis of a proxy marker or event that correlates with presence of the nucleic acid or nucleic acid sequence.

High-molecular weight DNA: As used herein the phrase "high-molecular weight DNA" refers to, among other things, DNA that will easily travel with and/or co-purify with genomic DNA throughout processing. High-molecular weight DNA typically will not travel through a standard, e.g., agarose gel (e.g., 1-2% agarose) used for genotyping or analysis of short (5 kilobases or less) PCR products or digested/cut DNA. In some embodiments, high-molecular weight DNA is distinct from PCR products in that PCR products are not typically high-molecular weight and may be structurally different. In some embodiments high-molecular weight DNA comprises or consists of at least about 400 bases, at least about 500 bases, at least about 600 bases, at least about 700 bases, at least about 800 bases, at least about 900 bases, at least about 1 kilobase, at least about 2 kilobases, at least about 3 kilobases, at least about 4 kilobases, at least about 5 kilobases, at least about 6 kilobases, at least about 7 kilobases, at least about 8 kilobases, at least about 9 kilobases, at least about 10 kilobases, at least about 11 kilobases, at least about 12 kilobases, at least about 13 kilobases, at least about 14 kilobases, at least about 15 kilobases, at least about 16 kilobases, at least about 17 kilobases, at least about 18 kilobases, at least about 19 kilobases, at least about 20 kilobases, at least about 30 kilobases, at least about 40 kilobases, at least about 50 kilobases, at least about 60 kilobases, at least about 70 kilobases, at least about 80 kilobases, at least about 90 kilobases, at least about 100 kilobases or greater than 100 kilobases.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar (e.g., containing residues with related chemical properties at corresponding positions). As will be understood by those skilled in the art, a variety of algorithms are available that permit comparison of sequences in order to determine their degree of homology, including by permitting gaps of designated length in one sequence relative to another when considering which residues "correspond" to one another in different sequences. Calculation of the percent homology between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position; when a position in the first sequence is occupied by a similar nucleotide as the corresponding position in the second sequence, then the molecules are similar at that position. The percent homology between the two sequences is a function of the number of identical and similar positions shared by the sequences, taking into account the number of gaps, and the length of each gap, which needs to be introduced for optimal alignment of the two sequences. Representative algorithms and computer programs useful in determining the percent homology between two nucleotide sequences include, for example, the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent homology between two nucleotide sequences can, alternatively, be determined for example using the GAP program in the GCG software package using an NWSgapdna.CMP matrix.

Identity: As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. Calculation of the percent identity of two nucleic acid or polypeptide sequences, for example, can be performed by aligning the two sequences for optimal comparison purposes (e.g., gaps can be introduced in one or both of a first and a second sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0). In some exemplary embodiments, nucleic acid sequence comparisons made with the ALIGN program use a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

Isolated: As used herein, the term "isolated", refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a nucleic acid molecule that is chemically synthesized or is synthesized in a cellular system different from that which produces it in nature is considered to be an "isolated" nucleic acid molecule. Alternatively or additionally, in some embodiments, a nucleic acid molecule that has been subjected to one or more purification techniques may be considered to be an "isolated" nucleic acid molecule to the extent that it has been separated from other components a) with which it is associated in nature; and/or b) with which it was associated when initially produced.

Linker: As used herein, the term "linker" is used to refer to that portion of a multi-element polypeptide that connects different elements to one another. For example, those of ordinary skill in the art appreciate that a polypeptide whose structure includes two or more functional or organizational domains often includes a stretch of amino acids between such domains that links them to one another. In some embodiments, a polypeptide comprising a linker element has an overall structure of the general form S1-L-S2, wherein S1 and S2 may be the same or different and represent two domains associated with one another by the linker. In some embodiments, a linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. In some embodiments, a linker is characterized in that it tends not to adopt a rigid three-dimensional structure, but rather provides flexibility to the polypeptide. A variety of different linker elements that can appropriately be used when engineering polypeptides (e.g., fusion polypeptides) known in the art (see e.g., Holliger, P., et al. (1993) Proc. Natl. Acad. Sci. USA 90:6444-6448; Poljak, R. J., et al. (1994) Structure 2: 1 121-1123).

Nucleic acid: As used herein, the term "nucleic acid", in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is single stranded; in some embodiments, a nucleic acid is double stranded. In some embodiments a nucleic acid has a nucleotide sequence comprising at least one element that encodes, or is the complement of a sequence that encodes, a polypeptide. In some embodiments, a nucleic acid has enzymatic activity.

Predominantly present: The term "predominantly present", as used herein, refers to the presence of an entity (e.g., an amino acid residue) at a particular location across a population. For example, an amino acid may be predominantly present if, across a population of polypeptides, a particular amino acid is statistically present at a particular position in at least about 50%, about 55%, about 60%, about 65%, about 70%, about 75%, about 80%, about 85%, about 90%, about 95%, about 96%, about 97%, about 98%, about 99% or more of the polypeptides within a relevant population.

Primer landing pad: As used herein, the phrase "primer landing pad" refers to a priming site on a stretch of a nucleic acid to which a complementary stretch of nucleic acids, such as an oligonucleotide used for priming a PCR amplification reaction, may bind. In some embodiments, such primer landing pads are suitable to priming multiple displacement amplification reactions.

Pure: As used herein, an agent or entity is "pure" if it is substantially free of other components. For example, a preparation that contains more than about 90% of a particular agent or entity is typically considered to be a pure preparation. In some embodiments, an agent or entity is at least 91%, at least 92%, at least 93%, at least 94%, at least 95%, at least 96%, at least 97%, at least 98%, or at least 99% pure.

Random: As used herein, the term "random" refers to a method of generating an algorithm-assembled sequence or an algorithm-assembled sequence used to generate arrangement of nucleic acids based on stochastic choice, filtered by criteria such as GC content, length, and edit distance between any two sequences.

Reference: As used herein, the term "reference" describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Sample: As used herein, the term "sample" refers to a substance that is or contains a composition of interest for qualitative and or quantitative assessment. In some embodiments, a sample is a biological sample (i.e., comes from a living thing (e.g., cell or organism). In some embodiments, a sample is from a geological, aquatic, astronomical or agricultural source. In some embodiments, a source of interest comprises or consists of an organism, such as an animal or human. In some embodiments, a sample for forensic analysis is or comprises biological tissue, biological fluid, organic or non-organic matter such as, e.g., clothing, dirt, plastic, water. In some embodiments, an agricultural sample, comprises or consists of organic matter such as leaves, petals, bark, wood, seeds, plants, fruit, etc.

Single Nucleotide Polymorphism (SNP): As used herein, the term "single nucleotide polymorphism" or "SNP" refers to a particular base position in the genome where alternative bases are known to distinguish one allele from another. In some embodiments, one or a few SNPs and/or CNPs is/are sufficient to distinguish complex genetic variants from one another so that, for analytical purposes, one or a set of SNPs and/or CNPs may be considered to be characteristic of a particular variant, trait, animal, line, breed, cross-breed, or set thereof. In some embodiments, one or a set of SNPs and/or CNPs may be considered to define a particular variant, trait, animal, line, breed, cross-breed, or set thereof.

Specific: The term "specific", when used herein with reference to an agent having an activity, is understood by those skilled in the art to mean that the agent discriminates between potential target entities or states. For example, in some embodiments, an agent is said to bind "specifically" to its target if it binds preferentially with that target in the presence of one or more competing alternative targets. In many embodiments, specific interaction is dependent upon the presence of a particular structural feature of the target entity (e.g., an epitope, a cleft, a binding site). It is to be understood that specificity need not be absolute. In some embodiments, specificity may be evaluated relative to that of the binding agent for one or more other potential target entities (e.g., competitors). In some embodiments, specificity is evaluated relative to that of a reference specific binding agent. In some embodiments specificity is evaluated relative to that of a reference non-specific binding agent. In some embodiments, the agent or entity does not detectably bind to the competing alternative target under conditions of binding to its target entity. In some embodiments, binding agent binds with higher on-rate, lower off-rate, increased affinity, decreased dissociation, and/or increased stability to its target entity as compared with the competing alternative target(s).

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantial identity: As used herein, the phrase "substantial identity" refers to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul et al., Basic local alignment search tool, J. Mol. Biol., 215(3): 403-410, 1990; Altschul et al., *Local Alignment Statistics*, Methods in Enzymology 266:460-480 (1996); Altschul et al., Nucleic Acids Res. 25:3389-3402, 1997; Baxevanis et al., Bioinformatics: A Practical Guide to the Analysis of Genes and Proteins, Wiley, 1998; and Misener, et al, (eds.), Bioinformatics Methods and Protocols (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial sequence homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, J. Mol. Biol., 215(3): 403-410, 1990; Altschul et al., *Local Alignment Statistics*, Methods in Enzymology 266: 460-480 (1996); Altschul, et al., "Gapped BLAST and PSI-BLAST: a new generation of protein database search programs", Nucleic Acids Res. 25:3389-3402, 1997; Baxevanis, et al., Bioinformatics: A Practical Guide to the Analysis of Genes and Proteins, Wiley, 1998; and Misener, et al., (eds.), Bioinformatics Methods and Protocols (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are homologous over a relevant stretch of residues. In some embodiments, the relevant stretch is a complete sequence. In some embodiments, the relevant stretch is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500 or more residues.

Synthetic: As used herein, the word "synthetic" means produced by the hand of man, and therefore in a form that does not exist in nature, either because it has a structure that does not exist in nature, or because it is either associated with one or more other components, with which it is not associated in nature, or not associated with one or more other components with which it is associated in nature.

Variable: As used herein, the term "variable" refers to differences between a particular element such that, for example, a region that is not considered constant. For example, in a sequence arranged according to an AB formula, if a set of sequences has a constant region "A" and a different sequence in each member of the set in region "B", the sequence of "B" is variable. As used herein, variable also applied to the concept of designing a tag of the present invention by producing a limiting dilution of a degenerate oligonucleotide mixture.

Variant: As used herein, the term "variant" refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs double, E vs Z, etc.) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to another in linear or three-dimensional space. For example, a variant polypeptide may differ from a reference polypeptide as a result of one or more differences in amino acid sequence and/or one or more differences in chemical moieties (e.g., carbohydrates, lipids, etc.) covalently attached to the polypeptide backbone. In some embodiments, a variant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, a variant may also have one or more functional defects and/or may otherwise be considered a "mutant". In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide.

DETAILED DESCRIPTION OF CERTAIN EMBODIMENTS

The present application provides, among other things, tags. In one aspect, the tags are useful for identifying samples, tracking samples, analyzing samples, the like, and combinations thereof.

Referring to FIG. 1, an embodiment of a method 100 according to the present disclosure includes the use of high-molecular weight DNA tags that can be combined with samples for identification, tracking, analysis, and the like. A step 102 of the method 100 includes collecting samples. In one aspect, the one or more samples can include nucleic acids to be analyzed. Accordingly, the samples can be collected from any suitable source comprising nucleic acids. One example source from which a sample can be collected includes one or more human, plant or animal subjects, although other sources can be suitable as described herein. In a step 104 of the method 100, the samples are combined with the tags of the present disclosure. In general, each sample can be combined with a unique tag sequence in order to differentiate the samples from one another during downstream analysis. With respect to the method 100, a tag is considered unique if the nucleic acid sequence of the tag is different from each other tag used in the method 100 by at least one nucleotide.

With continued reference to FIG. 1, a step 106 includes extracting the DNA and optionally other nucleic acids from the samples including the tags. DNA extraction will yield a combination of i) nucleic acids from the sample, and ii) tag DNA. In a step 108, the extracted DNA is fragmented using any suitable technique, such as shearing, enzymatic fragmentation, sonication, or the like. In a step 110, a variety of optional steps can be performed to further prepare the DNA samples for sequencing or other downstream analysis. For example, the ends of the fragmented DNA can be repaired, A-tailing can be performed for T-A based adapter ligation or the like, and adapters can be ligated or otherwise added to the fragmented DNA. Further manipulations such as DNA fragment size selection and quality control testing of the prepared DNA library can be performed in the step 112.

In a next step 114 of the method 100, the prepared samples including the tag DNA can be pooled together (i.e., multiplexed) for sequencing or other downstream analysis. Thereafter, the data acquired in the step 114 can be de-multiplexed and analyzed in the step 116.

In certain embodiments of the methods of the disclosure, the high-molecular weight DNA tags of the disclosure may be combined with one or more samples immediately following collection (see, for example, FIG. 1). Moreover, the high-molecular weight DNA tags of the disclosure may be processed along with the sample sequences (e.g. genomic DNA sequences within a sample), without the need for additional or distinct steps for processing or detection of the tags other than those steps used to analyze the sample itself. Thus, unlike a polypeptide tag or a tag commonly comprising a visually detectable label or a label that specifically binds to an antibody, which is meant to be detected by a means other than DNA sequencing, the high-molecular weight DNA tags of the disclosure provide the same result of unambiguously identifying each sample within a high-throughput reaction comprising a plurality of samples (the plurality comprising or consisting of 1, 2, 3, 4, 5, 10, 25, 50, 100, 500, 1000, or any integer in between of distinct samples) while eliminating the steps of processing or detecting the tags themselves that are commonly required in other technologies. Each distinct sample may comprise one or more tags that provide an identification code for each sample. The identification of any tag that does not belong to the designated code for any given sample within that sample indicates contamination. Because each code is unique to each sample, the origin of the contamination is immediately known once the contaminating tag is identified. For high-throughput applications, using a tag comprised of the same material as the sample (a DNA polymer), while having a unique sequence allows for significantly increased efficiency for identification, tracking, analysis, and the like of the sample sequences.

Samples

In some embodiments, a sample to be analyzed in accordance with the present invention (e.g., to which one or more tags may be added) contains nucleic acids. In some embodiments, a sample is characterized in that it is amenable to nucleic acid sequence analysis. For example, in some embodiments, a sample may be substantially free of one or more particular inhibitors of a nucleic acid sequencing enzyme or reagent. In some embodiments, a sample may be sufficiently pure with respect to the nucleic acid to be analyzed that such analysis can be successfully performed.

In some embodiments, a sample comprises or consists of a biological, clinical, forensic, geological, astronomical, aquatic, or agricultural sample. In certain embodiments, a sample is a crude sample (e.g., blood, rock, wood, pond water), which has not been processed, or a sample is processed and/or purified (e.g., DNA extracted and, optionally purified, from sources such as blood, bark, leaves, seeds) (FIG. 1).

In some embodiments, a biological sample comprises or consists of biological tissue or fluid. In some embodiments, a biological sample may comprise or consist of bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; other body fluids, secretions, and/or excretions; and/or cells therefrom, etc. In some embodiments, a biological sample comprises or consists of cells obtained from an individual. In some embodiments, obtained cells are or include cells from an individual from whom the sample is obtained.

In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from the context, the term "sample" refers to a preparation that is not processed or is minimally processed. Such a "crude sample" may comprise, for instance, urine that is not subject to further processing after collection from an organism. In some embodiments, a crude sample is collected and not further processed prior to analysis and/or prior to addition of a tag.

In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc. In some embodiments, processing applied to a crude sample has an effect of purifying nucleic acid that was present in the crude sample, so that a sample for analysis is provided.

As described herein, the present inventors have successfully developed tags and methods of using such tags that demonstrate their success in various applications. Tags are useful in applications such as sample tracking, sample identification and sample analysis (e.g., sequencing). Tags of the present invention provide certain characteristics and advantages over existing tags and methods of sample tracking, identification and/or analysis.

In some embodiments, such tags may be added, or "spiked in" to a sample, such that at least one sample and at least one or more tags are present in close proximity, such as, e.g., in a collection tube, in a well-plate, or on the surface of an object. Combining a sample and at least one tag in close proximity allows for easy determination of sample identity, which can be assayed by various sequencing protocols and without the need for any imputation.

In some embodiments, a sample is utilized in a nucleic acid sequencing reaction (e.g., a DNA sequencing reaction).

In some embodiments, a tag is used in, e.g., sample identification and/or analysis (FIG. 1).

Tags

The present disclosure provides tags for use e.g., in tracking, identifying and/or otherwise improving processing of nucleic acid samples undergoing analysis. Provided tags confer a variety of advantages relative to known tags or tagging systems, for example, when used to identify and/or detect cross-contamination of nucleic acid samples.

Known tagging systems include, for example, that described in international patent application publication WO 2014128453 by Quail et al. (hereinafter "Quail"), which discloses "nucleic acid marker molecules", e.g., for identifying nucleic acid samples and for detecting cross-contamination of samples. The marker molecules of Quail are PCR fragments of varying lengths, generated using phiX (a virus) as template, with out-nested (flanking the sequence on each end) barcodes. The described phiX sequences with flanking barcodes are themselves the tags ("Quail tags"), and are added to samples in order to e.g., track and/or identify samples through processing and sequence analysis. Quail discloses adding its nucleic acid marker molecules to track samples from pre-processing through sequencing and analysis (hereinafter, the "Quail technology").

The present disclosure identifies and/or appreciates certain limitations of known tagging systems such as the Quail technology. For example, the Quail technology utilizes nucleic acid marker molecules of various sizes that are relatively short and of low molecular weight. The present disclosure provides the insight that such a strategy is not suitable for certain applications including, e.g., long sequence read applications, and, furthermore, may not be readily scalable to applications involving hundreds, thousands and/or hundreds of thousands of samples or more. Moreover, the present disclosure appreciates that, if the nucleic acid marker molecules as described by Quail were added to a crude sample, they likely would be susceptible to breakdown during subsequent processing steps (e.g., during a shearing step).

The present invention provides, among other things, tags comprised of high-molecular weight DNA, methods of using the tags, and kits, collection vials, and other and containers including the tags. Further, the provided tags are suitable, among other things, for a variety of applications, such as e.g., long-read applications, scalability to applications involving at least hundreds, thousands and/or hundreds of thousands of samples or more, tagging, tracking, and/or identifying samples from e.g., point of collection, prior to separation or purification, through to sequencing and analysis.

In some embodiments, the tags described herein comprise synthetic, high-molecular weight nucleic acids (e.g., double-stranded DNA ("dsDNA")), such that when a tag is added to a sample and remains with the sample throughout processing. High-molecular weight DNA tags may, similar to genomic or high-molecular weight DNA in a sample, tolerate typical processing procedures, e.g., separation, purification and analysis.

In some embodiments, the high-molecular weight nature of the tags makes them ideal for use in sample tagging for long-read technologies (e.g., PACBIO, OXFORD NANOPORE, GENIA, ROCHE). Short PCR tags and/or short oligonucleotides are generally not suitable or desired for use in such applications.

Provided tags are useful, among other things, for example tracking, for example in forensic, medical and/or agricultural fields.

Tag Design

It is contemplated that useful such tags may be designed and/or constructed to have a nucleotide sequence that comprises or consists of a repeating unit of sequence A (constant) sequence B (unique to each tag) and sequence C (constant), with at least two repeating units of A-B—C per tag. In some embodiments, a tag is arranged according to a formula comprising X-[A-B—C]$_n$—Y, wherein n is at least two, and each of A, B, and C has a defined length of 2 or more residues. In some embodiments, X is optionally present or absent, and if present, may consist of or comprise one or more instances of —C—, or otherwise may consist of or comprise another element. In some embodiments, Y is optionally present or absent, and if present, may consist of or comprise one or more instances of -A-, or otherwise may consist of or comprise another element. In some embodiments, the element comprises or consists of nucleic acids, 5' or 3' primer modifications (e.g., phosphorothioation, internal modification, methylated cytosines, etc.).

In one aspect, it will be appreciated that the generalized X[A-B—C]$_n$—Y structure of the tags provides for straightforward and consistent identification of reads derived from tags. In another aspect, the structure of the tags can enable the confidential removal or sanitization of tag-derived reads, which can be useful for de novo genome sequencing and other like applications where there is no sample reference or key.

In some embodiments, a tag is considered to be high-molecular weight if it behaves similarly to genomic DNA. In some embodiments, a tag is considered to be high-molecular weight if it persists through a processing procedure (e.g., shearing).

In some embodiments, a tag is considered to be high-molecular weight if it has a molecular mass within a range bounded by a lower limit and an upper limit, where the upper limit is larger than the lower limit; in some such embodiments the lower limit is about 260000 Daltons, about 325000 Daltons, about 390000 Daltons, about 455000 Daltons, about 520000 Daltons, about 585000 Daltons, about 650000 Daltons, about 1300000 Daltons, about 1950000 Daltons, about 2600000 Daltons, about 3250000 Daltons, about 3900000 Daltons, about 4550000 Daltons, about 5200000 Daltons, about 5850000 Daltons, about 6500000 Daltons, about 7150000 Daltons, about 7800000, about 8450000 Daltons, about 9100000 Daltons, about 9750000 Daltons, about 10400000 Daltons, about 11050000 Daltons, about 11700000 Daltons, about 12350000 Daltons, about 13000000 Daltons, about 19500000 Daltons, about 26000000 Daltons, about 32500000, about 39000000 Daltons, about 45500000 Daltons, about 52000000 Daltons, about 58500000 Daltons, about 65000000 Daltons or greater than 65000000 Daltons. In some embodiments, the upper limit is about 325000 Daltons, about 390,000 Daltons, about 450000 Daltons, about 520000 Daltons, about 585000 Daltons, about 650000 Daltons, about 1300000 Daltons, about 1950000 Daltons, about 2600000 Daltons, about 3250000 Daltons, about 3900000 Daltons, about 4550000 Daltons, about 5200000 Daltons, about 5850000 Daltons, about 6,500,000 Daltons, about 7150000 Daltons, about 7800000, about 8450000 Daltons, about 9100000 Daltons, about 9750000 Daltons, about 10400000 Daltons, about 11050000 Daltons, about 11700000 Daltons, about 12350000 Daltons, about 13000000 Daltons, about 19500000 Daltons, about 26000000 Daltons, about 32500000, about 39000000 Daltons, about 45500000 Daltons, about 52000000 Daltons, about 58500000 Daltons, about 65000000 Daltons or greater than 65000000 Daltons. In some embodiments, a high-molecular weight tag has a molecular mass within a range of about 260000 Daltons to about greater than 65000000 Daltons. In some embodiments, a high-molecular weight tag has a molecular mass within a range of about 325000 Daltons to about 65000000 Daltons. In some embodiments, a high-molecular weight tag has a molecular mass within a range of about 390,000 Daltons to about 58500000 Daltons.

In some embodiments, a tag is considered to be high-molecular weight if it has a length within a range bounded by a lower limit and an upper limit, where the upper limit is larger than the lower limit; in some such embodiments the lower limit is about 400 bases, about 500 bases, about 600 bases, about 700 bases, about 800 bases, about 900 bases, about 1 kilobase, about 2 kilobases, about 3 kilobases, about 4 kilobases, about 5 kilobases, about 6 kilobases, about 7 kilobases, about 8 kilobases, about 9 kilobases, about 10 kilobases, about 11 kilobases, about 12 kilobases, about 13 kilobases, about 14 kilobases, about 15 kilobases, about 16 kilobases, about 17 kilobases, about 18 kilobases, about 19 kilobases, about 20 kilobases, about 30 kilobases, about 40 kilobases, about 50 kilobases, about 60 kilobases, about 70 kilobases, about 80 kilobases, about 90 kilobases, about 100 kilobases, and greater than 100 kilobases. In some embodiments, the upper limit is about 500 bases, about 600 bases, about 700 bases, about 800 bases, about 900 bases, about 1 kilobase, about 2 kilobases, about 2 kilobases, about 2 kilobases, about 3 kilobases, about 4 kilobases, about 5 kilobases, about 6 kilobases, about 7 kilobases, about 8 kilobases, about 9 kilobases, about 10 kilobases, about 11 kilobases, about 12 kilobases, about 13 kilobases, about 14 kilobases, about 15 kilobases, about 16 kilobases, about 17 kilobases, about 18 kilobases, about 19 kilobases, about 20 kilobases, about 30 kilobases, about 40 kilobases, about 50 kilobases, about 60 kilobases, about 70 kilobases, about 80 kilobases, about 90 kilobases, about 100 kilobases and greater than 100 kilobases. In some embodiments, a high-molecular weight tag has a length within a range between about 400 bases and about greater than 100 kilobases. In some embodiments, a high-molecular weight tag has a length within a range between about 500 bases and about 100 kilobases. In some embodiments, a high-molecular weight tag has a length within a range between about 600 bases and about 90 kilobases. In some embodiments, a high-molecular weight tag has a length within a range between about 700 bases and about 80 kilobases. In some embodiments, a high-molecular weight tag has a length within a range between about 800 bases and about 70 kilobases. In some embodiments, a high-molecular weight tag has a length within a range between about 900 bases and about 60 kilobases. In some embodiments, a high-molecular weight tag has a length within a range between about 1 kilobase and about 50 kilobases. In some embodiments, a high-molecular weight tag has a length within a range between about 2 kilobases and about 40 kilobases. In some embodiments, a high-molecular weight tag has a length within a range between about 3 kilobases and about 30 kilobases. In some embodiments, a high-molecular weight tag has a length within a range between about 4 kilobases and about 20 kilobases. In some embodiments, a high-molecular weight tag has a length within a range between about 5 kilobases and about 19 kilobases. In some embodiments, a high-molecular weight tag has a length within a range between about 6 kilobases and about 18 kilobases. In some embodiments, a high-molecular weight tag has a length within a range between about 7 kilobases and about 17 kilobases. In some embodiments, a high-molecular weight tag has a length within a range between about 7 kilobases and about 16 kilobases. In some embodiments, a high-molecular weight tag has a length within a range between about 8 kilobases and about 15 kilobases. In some embodiments, a high-molecular weight tag has a length within a range between about 9 kilobases and about 14 kilobases. In some embodiments, a high-molecular weight tag has a length within a range between about 10 kilobases and about 13 kilobases. In some embodiments, a high-molecular weight tag has a length within a range between about 11 kilobases and about 12 kilobases. In some embodiments, a high-molecular weight tag has a length within a range between about 500 bases and about 5 kilobases. In some embodiments, a high-molecular weight tag has a length within a range between about 600 bases and about 6 kilobases. In some embodiments, a high-molecular weight tag has a length within a range between about 700 bases and about 7 kilobases. In some embodiments, a high-molecular weight tag has a length within a range between about 800 bases and about 8 kilobases. In some embodiments, a high-molecular weight tag has a length within a range between about 900 bases and about 9 kilobases. In some embodiments, a high-molecular weight tag has a length within a range between about 1 kilobase and about 50 kilobases. In some embodiments, a high-molecular weight tag has a length within a range between about 2 kilobases and about 40 kilobases. In some embodiments, a high-molecular weight tag has a length within a range between about 2 kilobases and about 30 kilobases. In some embodiments, a high-molecular weight tag has a length within a range between about 2 kilobases and about 20 kilobases. In some embodiments, a high-molecular weight tag has a length within a range between about 1 kilobase and about 5 kilobases.

In some embodiments, it is contemplated that a tag may comprise or consist of at least about 12 nucleotides to at least about than 300,000 nucleotides. In some embodiments, a tag may comprise or consist of at least about 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 550, 600, 650, 700, 750, 800, 850, 900, 950, 1000, 2000, 300, 4000, 5000, 6000, 7000, 8000, 9000, 10000, 11000, 12000, 13000, 14000. 15000, 16000, 17000, 18000, 19000, 20000, 21000, 22000, 23000, 24000, 25000, 26000, 27000, 28000, 29000, 30000, 31000, 32000, 33000, 34000, 35000, 36000, 37000, 38000, 39000, 40000, 41000, 42000, 43000, 44000, 45000, 46000, 47000, 48000, 49000, 50000, 60000, 70000, 80000, 90000, 100000, 110000, 120000, 130000, 140000, 150000, 160000, 170000, 180000, 190000, 200000, 210000, 220000, 230000, 240000, 250000, 260000, 270000, 280000, 290000, or 300000 bases.

In some embodiments, a tag may comprise or consist of at least about 12 nucleotides to at least about 100 nucleotides. In some embodiments, a tag may comprise or consist of at least about 13 nucleotides to at least about 99 nucleotides. In some embodiments, a tag may comprise or consist of at least about 14 nucleotides to at least about 98 nucleotides. In some embodiments, a tag may comprise or consist of at least about 15 nucleotides to at least about 97 nucleotides. In some embodiments, a tag may comprise or consist of at least about 16 nucleotides to at least about 96 nucleotides. In some embodiments, a tag may comprise or consist of at least about 17 nucleotides to at least about 95 nucleotides. In some embodiments, a tag may comprise or consist of at least about 18 nucleotides to at least about 94 nucleotides. In some embodiments, a tag may comprise or consist of at least about 19 nucleotides to at least about 93 nucleotides. In some embodiments, a tag may comprise or consist of at least about 20 nucleotides to at least about 92 nucleotides. In some embodiments, a tag may comprise or consist of at least about 20 nucleotides to at least about 90 nucleotides. In some embodiments, a tag may comprise or consist of at least about 20 nucleotides to at least about 80 nucleotides. In some embodiments, a tag may comprise or consist of at least about 20 nucleotides to at least about 70 nucleotides. In some embodiments, a tag may comprise or consist of at least about 20 nucleotides to at least about 60 nucleotides. In some embodiments, a tag may comprise or consist of at least about 20 nucleotides to at least about 50 nucleotides.

Without being bound to any particular theory, it is considered that, in some embodiments, having multiple units per tag may provide certain particular advantages. In some embodiments, a tag has at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90, 100, 110, 120, 130, 140, 150, 160, 170, 180, 190, 200, 210, 220, 230, 240, 250, 260, 270, 280, 290, 300 or greater than 300 units. In some embodiments, a tag comprises or consists of at least about 2 to about 300 units. In some embodiments, a tag comprises or consists of at least about 3 to about 290 units. In some embodiments, a tag comprises or consists of at least about 24 to about 280 units. In some embodiments, a tag comprises or consists of at least about 5 to about 270 units. In some embodiments, a tag comprises or consists of at least about 6 to about 260 units. In some embodiments, a tag comprises or consists of at least about 7 to about 250 units. In some embodiments, a tag comprises or consists of at least about 8 to about 240 units. In some embodiments, a tag comprises or consists of at least about 9 to about 230 units. In some embodiments, a tag comprises or consists of at least about 10 to about 220 units. In some embodiments, a tag comprises or consists of at least about 11 to about 210 units. In some embodiments, a tag comprises or consists of at least about 12 to about 200 units. In some embodiments, a tag comprises or consists of at least about 13 to about 190 units. In some embodiments, a tag comprises or consists of at least about 14 to about 180 units. In some embodiments, a tag comprises or consists of at least about 15 to about 170 units. In some embodiments, a tag comprises or consists of at least about 16 to about 180 units. In some embodiments, a tag comprises or consists of at least about 17 to about 190 units. In some embodiments, a tag comprises or consists of at least about 18 to about 180 units. In some embodiments, a tag comprises or consists of at least about 19 to about 170 units. In some embodiments, a tag comprises or consists of at least about 20 to about 160 units. In some embodiments, a tag comprises or consists of at least about 21 to about 150 units. In some embodiments, a tag comprises or consists of at least about 22 to about 140 units. In some embodiments, a tag comprises or consists of at least about 23 to about 130 units. In some embodiments, a tag comprises or consists of at least about 24 to about 120 units. In some embodiments, a tag comprises or consists of at least about 25 to about 110 units. In some embodiments, a tag comprises or consists of at least about 26 to about 100 units. In some embodiments, a tag comprises or consists of at least about 27 to about 90 units.

In some embodiments, number of units included in a particular tag may be influenced and/or determined by length of an individual unit. In general, a tag comprised of shorter individual units may have a larger number of such units than does a tag whose units are longer.

In some embodiments unit length is at least about 6 nucleic acids to at least about greater than 1000 nucleic acids. In some embodiments, unit length is at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 550, 600, 650, 700, 750, 800, 850, 900, 950, 1000 and greater than 1000 nucleic acids.

In some embodiments, unit length is at least about 20 to at least about 100. In some embodiments, unit length is at least about 20 to at least about 80. In some embodiments, unit length is at least about 30 to at least about 80. In some embodiments, unit length is at least about 20 to at least about 60. In some embodiments, unit length is at least about 10 to at least about 100. In some embodiments, unit length is about 10 to at least about 80. In some embodiment, unit length is at least about 40 to at least about 80. In some embodiments, unit length is at least about 30 to at least about 90. In some embodiments, unit length is at least about 40 to at least about 70. In some embodiments, a tag has a general structure X[A-B—C]$_n$—Y, wherein X and Y are optional, and each of A, B, and C, is a sequence element defined and/or selected as described herein. Without wishing to be bound by any particular theory, it is proposed herein that high-molecular weight nucleic acid tags having such structure (i.e., having a structure characterized by multiple repeating A-B—C units), may show particular advantageous features including, for example, high stability. Among other things, the present disclosure provides the insight that tags of such structure may share certain characteristics with high-molecular weight DNA found in natural samples (e.g., in genomic DNA).

As demonstrated herein, tags with concatemeric structure (e.g., whose structure comprises or consists of repeats of units arranged in series according to the formula X-[A-B—C]$_n$—Y, as described herein) are capable of surviving/persisting through various sample preparation procedures, including some that do or may destroy or degrade other available marking agents (e.g., Quail nucleic acid marker molecules and/or other shorter oligonucleotide agents, particularly linear oligonucleotides, and/or oligonucleotides of a length within the range of about 2 to about 600 residues as may be generated, for example, by PCR, that do not have the structure [e.g., X-[A-B—C]$_n$—Y] of tags described herein).

In some embodiments, elements A and C in provided tags have sequences designed and/or selected to hybridize with primers and permit their extension to generate nucleic acid (e.g., DNA) polymers. In some embodiments, elements A and C are specifically designed to hybridize with members of a primer pair useful in a polymerase chain reaction ("PCR"). In some embodiments, elements A and C are designed to be compatible with one another in the context of multiplex PCR reactions, such that priming is supported in a multiplex formation. In some embodiments, sequences of A and C are compatible with one another in the context of one or more (and, in some embodiments, with multiple) different platforms, e.g., hybridization capture, etc. For example, in some embodiments, elements A and C have sequences characterized by primers which hybridize to each of A and C, having comparable melting temperatures.

In general, element B has a sequence designed and/or selected to have a low or zero probability of being present in a sample to be analyzed. In some embodiments, element B has a sequence designed and/or selected to be distinct from any and all known sequences (e.g., as determined by reference to available databases of sequence information). For example, in some embodiments, element B has a sequence designed and/or selected to have equal to or less than 1%, 2%, 3%, 4%, 5%, 6%, 7%, 8%, 9%, 10%, 15%, 20%, 25%, 30%, 35%, 40%, 45%, 50%, or any percentage value in between of homology or identity to any and all known sequences (e.g., as determined by reference to available databases of sequence information). In some embodiments, element B has a sequence designed and/or selected to be distinct from any and all known plant sequences (e.g., as determined by reference to available databases of sequence information). For example, in some embodiments, element B has a sequence designed and/or selected to have equal to or less than 1%, 2%, 3%, 4%, 5%, 6%, 7%, 8%, 9%, 10%, 15%, 20%, 25%, 30%, 35%, 40%, 45%, 50%, or any percentage value in between of homology or identity to any and all known plant sequences (e.g., as determined by reference to available databases of sequence information). In some embodiments, element B has a sequence designed and/or selected to be distinct from any and all known vertebrate sequences (e.g., as determined by reference to available databases of sequence information). For example, in some embodiments, element B has a sequence designed and/or selected to have equal to or less than 1%, 2%, 3%, 4%, 5%, 6%, 7%, 8%, 9%, 10%, 15%, 20%, 25%, 30%, 35%, 40%, 45%, 50%, or any percentage value in between of homology or identity to any and all known vertebrate sequences (e.g., as determined by reference to available databases of sequence information). In some embodiments, element B has a sequence designed and/or selected to be distinct from any and all known invertebrate sequences (e.g., as determined by reference to available databases of sequence information). For example, in some embodiments, element B has a sequence designed and/or selected to have equal to or less than 1%, 2%, 3%, 4%, 5%, 6%, 7%, 8%, 9%, 10%, 15%, 20%, 25%, 30%, 35%, 40%, 45%, 50%, or any percentage value in between of homology or identity to any and all known invertebrate sequences (e.g., as determined by reference to available databases of sequence information). In some embodiments, element B has a sequence designed and/or selected to be distinct from any and all known mammalian sequences (e.g., as determined by reference to available databases of sequence information). For example, in some embodiments, element B has a sequence designed and/or selected to have equal to or less than 1%, 2%, 3%, 4%, 5%, 6%, 7%, 8%, 9%, 10%, 15%, 20%, 25%, 30%, 35%, 40%, 45%, 50%, or any percentage value in between of homology or identity to any and all known mammalian sequences (e.g., as determined by reference to available databases of sequence information). In some embodiments, element B has a sequence designed and/or selected to be distinct from any and all known human sequences (e.g., as determined by reference to available databases of sequence information). For example, in some embodiments, element B has a sequence designed and/or selected to have equal to or less than 1%, 2%, 3%, 4%, 5%, 6%, 7%, 8%, 9%, 10%, 15%, 20%, 25%, 30%, 35%, 40%, 45%, 50%, or any percentage value in between of homology or identity to any and all known human sequences (e.g., as determined by reference to available databases of sequence information). In some embodiments, element B has a sequence designed and/or selected to be distinct from any and all known viral, bacterial, microbial, and/or yeast sequences (e.g., as determined by reference to available databases of sequence information). For example, in some embodiments, element B has a sequence designed and/or selected to have equal to or less than 1%, 2%, 3%, 4%, 5%, 6%, 7%, 8%, 9%, 10%, 15%, 20%, 25%, 30%, 35%, 40%, 45%, 50%, or any percentage value in between of homology or identity to any and all known viral, bacterial, microbial, and/or yeast sequences (e.g., as determined by reference to available databases of sequence information). Publicly available databases of sequence information include, but are not limited to, for example, GenBank (ncbi.nlm.nih.gov/genbank), which is incorporated by reference herein in its entirety. Alternatively or additionally, in some embodiments, element B has a sequence designed and/or selected to have a sequence characterized by approximately 35-65%, approximately 40-60%, approximately 45-55%, or approximately 50% G/C content. In some embodiments, any or all of A, B, and/or C is or comprises a synthetic element in that it is chemically synthesized through action of the hand of man. In some embodiments, such chemical synthesis does not utilize a polymerase enzyme. In some embodiments, such chemical synthesis does utilize a polymerase enzyme, but not in the context of a cell, and/or not in the context of a cell that naturally produces the polymerase enzyme. In some embodiments, such chemical synthesis utilizes a polymerase enzyme that is a variant of a naturally occurring enzyme and/or is utilized in a context other than that in which it operates in nature (e.g., in vitro, ex vivo, absent natural template nucleic acid, in the presence of a label, etc.).

One insight provided by the present disclosure is that, in many embodiments, the precise identity of sequences included in elements A, B, and/or C as described herein may not be critical in order to achieve benefits provided by the overall structure of described tags. That is, in some embodiments, the present disclosure contemplates that any of a variety of specific sequences may be utilized as A, B, and C elements, subject to the guidelines provided herein, to assemble a high-molecular weight tag of desired repeating unit structure as described herein.

Thus, the present disclosure teaches and demonstrates utility and unexpected advantages of high-molecular weight nucleic acid tags of structure:

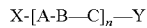

wherein X and Y are optional, and A, B, and C are as described herein. In many embodiments, each "A" within a tag is identical to each other "A" within the tag; each "B" within a tag is identical to each other "B" within the tag; and each "C" within a tag is identical with each other "C" within a tag, such that the tag has a structure of truly identical repeating units. However, as described herein, one aspect of the present disclosure is the insight that rigid definition of precise sequence identity within elements may not be required for effective and useful tagging as described herein. In some embodiments, a tag as described herein, may still be effective even when each and every repeated unit is not perfectly identical with every other unit. For example, in some embodiments, one or more "B" elements within a tag may vary. In some embodiments, one or more A or C elements may vary although, in general, it is preferred that all A and C elements in a single tag are compatible in that they can hybridize with an permit extension of the same primer set to generate an amplification product of comparable or identical length (which also requires that the B element between them be of an appropriate length to ensure such comparability or identity). Thus, for example, it is conceivable that a useful tag as described herein may have a structure:

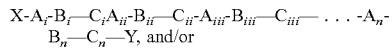

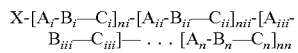

wherein each A is not necessarily identical to every other A, each B is not necessarily identical to each other B, and/or each C is not necessarily identical to each other C (and/or each n may or may not be equal to each other n), subject to the parameters described herein. In many or most embodiments, however, each A is identical to every other A, each B is identical to each other B, and/or each C is identical to each other C.

In some embodiments, any or all of A, B, and/or C has a sequence that is considered "random" or "synthetic" in that it is not selected or modeled on a particular reference sequence. In many embodiments, precise sequences included as elements A, B, and/or C, may be designed by inputting into a computer or otherwise implementing design guidelines as described herein (e.g., A and C include compatible primer hybridization sites, B has GC content within a relevant range, together A, B, and C form a unit of appropriate length and functional character to be a "unit" of a tag as described herein). In some embodiments, a "random" or "synthetic" sequence is characterized in that it does not (or is predicted not) to hybridize above background with other nucleic acids found (or expected to be found) in a particular sample or set of samples of interest; in some embodiments, such a random or synthetic sequence is considered to be able to "uniquely" mark (e.g., label) a sample to which it may be added. Such marking may permit ready identification and/or characterization of that sample if and when it undergoes other processing and/or analysis.

In some embodiments, a tag may have a structure that includes one or more linker elements (e.g., within one or more units, within all units, and/or between a terminal unit and any X or Y element that may be present). In general, a linker element, particularly an intra-unit linker element, is or comprises a small number (typically fewer than about 30, about 29, about 28, about 27, about 26, about 25, about 24, about 23, about 22, about 21, about 20, about 19, about 18, about 17, about 16, about 15, about 14, about 13, about 12, about 11, about 10, about 9, about 8, about 7, about 6, about 5, about 4, about 3, about 2, about 1, about 0) of nucleic acid residues. A linker should not interfere with function, as described herein, of individual elements, of units, and/or of tags, in which they are included or to which they are adjoined.

In some embodiments, a tag does not include any linker elements (e.g., has a structure that consists of X-[A-B—C]$_n$—Y) as described herein.

In some embodiments, a tag may have a sequence that includes a cleavage site (e.g., a restriction site). In some embodiments, a tag may have a sequence that includes multiple cleavage sites. In some embodiments, such cleavage site may be entirely within a single element (e.g., an X, Y, A, B, or C element); in some embodiments, it may be formed by juxtaposition of two different sequence elements.

In some embodiments, relatively long tags are preferable to ensure compatibility with the widest range of prep and sequencing protocols. In some embodiments, it is desirable that tags include a barcode motif, preferably long enough to be unequivocally identifiable, but short enough to ensure at least one full tag, e.g., per ~100 bp read; in certain embodiments exemplified herein, 20 base pair barcode motifs were utilized. In some embodiments barcode motifs are at least about 6 to at least about 10000 nucleotides. In some embodiments, barcode motifs are at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 550, 600, 650, 700, 750, 800, 850, 900, 950, 1000, 2000, 300, 4000, 5000, 6000, 7000, 8000, 9000, 10000 nucleotides. In some embodiments, barcode motifs are at least about 6 to at least about 100 nucleotides. In some embodiments, barcode motifs are at least about 8 to at least about 80 nucleotides. In some embodiments, barcode motifs are at least about 8 to at least about 60 nucleotides. In some embodiments, barcode motifs are at least about 10 to at least about 50 nucleotides. In some embodiments, barcode motifs are at least about 10 to at least about 40 nucleotides. In some embodiments, barcode motifs are at least about 10 to at least about 30 nucleotides. In some embodiments, barcode motifs are at least about 10 to at least about 20 nucleotides.

In some embodiments, tags are prepared at a standardized concentration, for example to allow accurate spiking. It is typically preferred that mass ratio of spike-in to template correlate well to percentage of spike-in derived reads in the relevant analysis (e.g., sequencing analysis, particularly Next Generation Sequencing analysis).

In some embodiments, tags are spiked into samples at a concentration of tag to sample of at least about 0.0001% to at least about 10%. In some embodiments, tags are spiked into samples at a concentration of tag to sample of at least about 0.001% to at least about 2%. In some embodiments, tags are spiked into samples at a concentration of tag to sample of at least about 0.01% to at least about 2%. In some embodiments, tags are spiked into samples at a concentration of tag to sample of at least about 0.1% to at least about 2%. In some embodiments, tags are spiked into samples at a concentration of tag to sample of at least about 1% to at least about 2%. In some embodiments, tags are spiked into samples at a concentration of tag to sample of at least about 0.001% to at least about 1%. In some embodiments, tags are spiked into samples at a concentration of tag to sample of at least about 0.01% to at least about 1%. In some embodiments, tags are spiked into samples at a concentration of tag to sample of at least about 0.1% to at least about 1%. In certain preferred embodiments, the ratio of tag to sample results in at least about 1 tag read per 100-100,000 sample reads.

It is appreciated that use of a high-molecular weight tag with repeating structure allows the use of conserved sequences (e.g., sequence elements A and C as exemplified herein) for capturing the spike in tags using either targeted polymerase chain reaction ("PCR"; (e.g., AMPLISEQ) or hybridization-based capture technologies.

Sets of Tags

In some embodiments, the present disclosure provides sets of tags as described herein, for example as may be utilized together (e.g., in a multiplexed sequencing analysis) to individually mark/label multiple distinct samples. In some embodiments, different tags within a set have related structures. To give but one example, in some embodiments, all tags in a set may have common A and/or C elements, but differ from one another in their B elements. In some such embodiments, all tags within a set may have B elements of comparable or identical lengths and/or GC content, etc., but different precise sequences.

For instance, in some embodiments, provided sets of tags (e.g., collections that comprise multiple tag populations) may be represented by the following sets of formulas:

Set 1:Tag 1,Tag 2, . . . ,Tag N

Tag 1:$X_1$-$[A_1$-$B_1$—$C_1]_{n1}$—$Y_1$

Tag 2:$X_2$-$[A_2$-$B_2$—$C_2]_{n2}$—$Y_2$

Tag N:$X_3$-$[A_N$-$B_N$—$C_N]_{nN}$—$Y_N$;

In some embodiments, n1, n2, and nN are all the same (i.e., all tags in the set have the same length); in some embodiments, n1, n2, and nN are comparable (i.e., all tags in the set have comparable lengths). In some embodiments, different tags in a set may have different lengths.

In some embodiments, as noted above, $A_1$, $A_2$, and $A_N$ are all the same (i.e., all tags in the set have a common "A" element) and/or $C_1$, $C_2$, and $C_N$ are all the same (i.e., all tags in the set have a common "C" element). In some embodiments, each B is different from each other B between sets of tags. In some embodiments, each B may or may not be different from each other B within a tag.

In some embodiments according to the generalized structure of a tag in a set as described herein, it is contemplated that so long as different tags within a set are distinguishable from one another, but share sufficient common characteristics or features to effectively function as a tag for, e.g., uniquely identifying a sample when exposed to comparable processing conditions, such tags will be suitable for at least applications as described herein, including, e.g., in the context of a multiplexed assessment such as multiplex sequencing.

In some embodiments, tags within a set are related to one another with their edit distance. The present disclosure provides the insight that tag sets with an edit distance of not more than about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30 and more and can be particularly useful as described herein. In some embodiments, a tag set is characterized by an edit distance within a range bounded by a lower limit and an upper limit, the upper limit being higher than the lower limit. In some embodiments, the lower limit is 2 and the upper limit is 30, and in certain embodiments within a range bounded by a lower limit in some embodiments, e.g., sets of tags, such that A and C are constant between tags and B is different, use of edit distance as an advantageous feature is contemplated.

The present invention particularly appreciates that primer sets with a limited edit distance as described herein show certain advantages relative to other technologies sometimes used for marking nucleic acid samples. For example, the Quail technology described herein, and other technologies (e.g., Illumina Sequencing platform), typically utilize short (e.g., within the range of about 4 to about 11) nucleic acids as barcodes or as markers (or "adapters") for indexing samples ("indexing barcodes"). The present disclosure provides the insight that use of such short adapters increases the likelihood that events during processing and sequencing may introduce changes to sequences of adapters such that, e.g., Barcode 1 is falsely identified as Barcode 2 due to an edit distance, for example, of 4 (i.e., three changes were introduced into Barcode 1, resulting in the call of the sequence being identified as Barcode 2).

In some embodiments, a large edit distance is contemplated such that the likelihood of falsely identifying one tag as another is decreased. In some embodiments, edit distance of at least about 4 to at least about 15 is contemplated. In some embodiments, edit distance is at least 4, 5, 6, 7, 8, 9, 10, 11, 12, 13, 14, 15, 16, 17, 18, 19, 20, 21, 22, 23, 24, 25, 26, 27, 28, 29 or 30. In some embodiments, the edit distance is between about 4 and about 15.

The present invention particularly appreciates that large edit distance is an advantage over other available methods. In some embodiments, the large edit distance allows for the possibility that potentially infinite numbers of tags and combinations can be generated. In addition to the large edit distance, the repetitive nature of the tags allows for the interrogation of multiple variable (B) regions in a single sequencing read on a next generation sequencing platform, which can provide further protection against sequencing and manufacturing errors.

Method of Making Tags

Tags according to the present invention may be produced using several methodologies. In some embodiments, tags generated via ligation of double-stranded DNA circles followed by multiple displacement amplification (MDA). In some embodiments, tags are produced according to the exemplary method shown in FIGS. 2-5.

Figure 2:
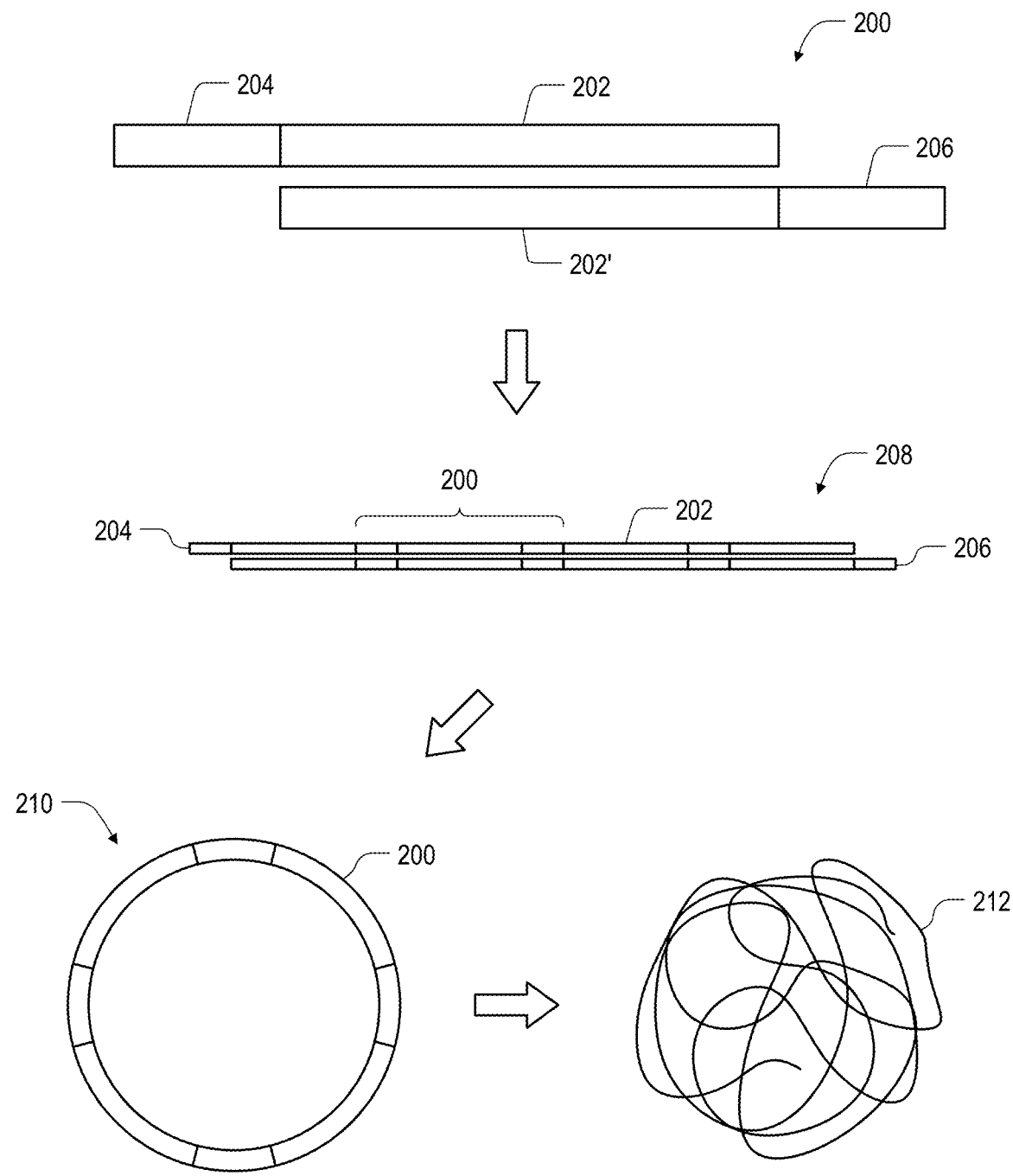
FIG. 2 is a schematic illustration of an embodiment of a method of making a number of tags according to the present disclosure.

Turning to FIG. 2, tag monomer 200 is a double-stranded DNA including a top strand 202 and a complimentary bottom strand 202'. In one aspect, the monomer 200 can include at least one unique nucleotide tag monomer of the formula [A-B—C] as described herein. The top strand 202 of the monomer 200 includes a 5' overhang 204, and the bottom strand 202' includes a 5' overhang 206. In the present example, the overhang 204 is complimentary to the overhang 206. Accordingly, the overhang 204 of one monomer 200 can be annealed the overhang 206 of another monomer 200, and the annealed monomers 200 can be ligated together. One example of a combination of four monomers 200 is shown as a linear tetramer 208 in FIG. 2. The linear tetramer 208 can be circularized and ligated to provide a double-stranded circular template 210. Notably, the circular template 210 includes a plurality of repeat units of the monomer 200. The circular template 210 can be replicated using a method such as one or more of the techniques described herein to provide a high-molecular weight DNA tag 212 having the formula $X_i$-[A-B—C]$_n$—$Y_j$. In one aspect, n represents the number of monomer or repeat units of a particular monomer sequence (typically at least two), and X and Y represent additional nucleic acids or nucleic acid modifications made to the ends of the tag 212.

In some embodiments, tags are produced using random or specific tag monomer oligonucleotides ligated to form small single-stranded DNA (ssDNA) circles (e.g., template 332, FIG. 3) followed by multiple displacement amplification (MDA). In some embodiments, tags are produced according to the exemplary method shown in FIGS. 3A, 3B, and 4. In some embodiments, tags are produced according to a method comprising or consisting of multiple steps. Such steps may occur sequentially or simultaneously and steps may be combined into single steps, e.g., in some embodiments, a first step and a second step may be performed in an order such as step 1 followed by step 2, whereas in some embodiments, a first step and a second step may be performed within a single step. In some embodiments, a first step comprises or consists of placement of specific tags or placement of a limiting dilution of a degenerate tag into a plate.

Figure 3A:
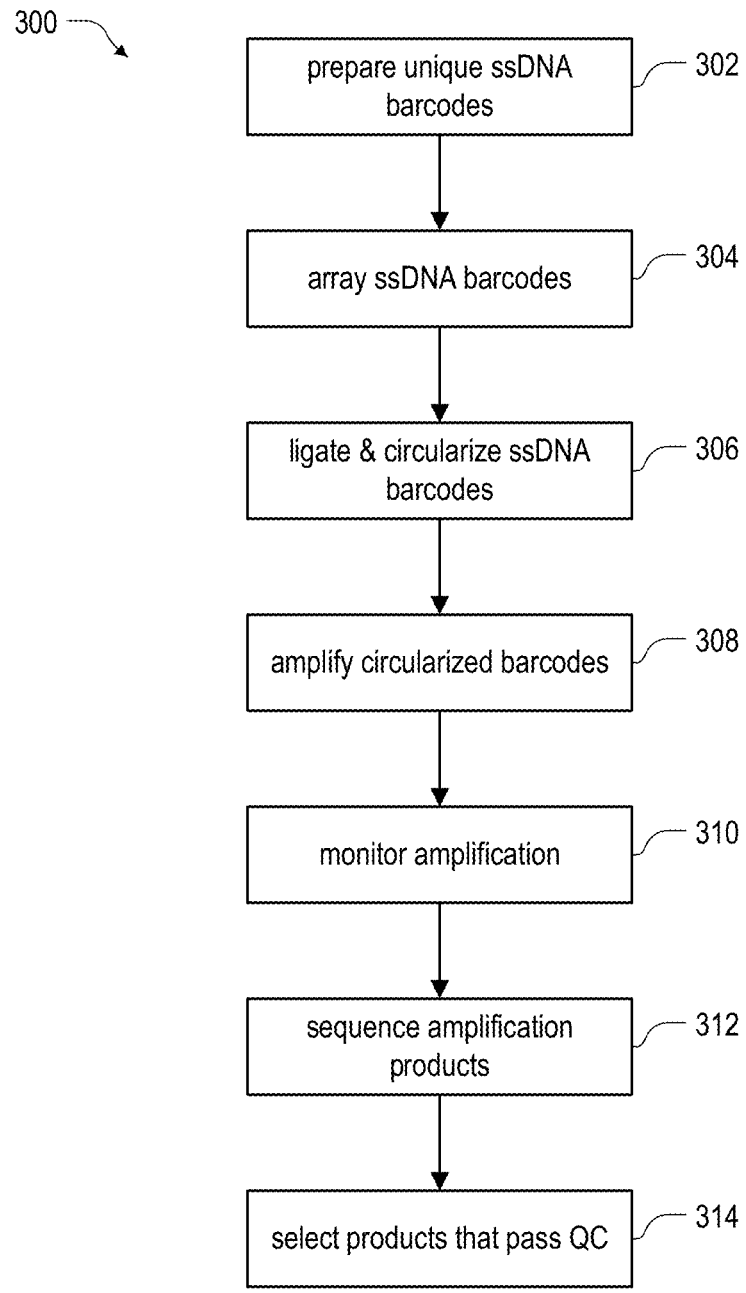
FIG. 3A is a first example of a high-throughput method of producing high-molecular weight sample tracking DNA tags according to the present disclosure.

Referring to FIG. 3A, one example method 300 of producing a tag includes a step 302 of preparing single stranded DNA (ssDNA) tag monomers having unique B region or barcode sequences. In a step 304, the tag monomers are arrayed, for example, into a multi-well plate (e.g., a standard 96 well plate). Thereafter, each of the ssDNA tag monomers can be circularized in a step 306 and amplified in a step 308. In a step 310, the amplification of the circularized tag monomers can be monitored using, for example, fluorescence-based quantitative polymerase chain reaction (qPCR), or another suitable technique. In one aspect, it may be useful to monitor amplification as a quality control measure to determine which of the tag monomers may have been successfully amplified. In a step 312, the products produced from amplification in the step 308 can be sequenced to further confirm successful amplification and to ensure that each of the tags was not contaminated with another one of the tags or tag monomers. Those products that pass the various quality control measures can be selected for further use in a step 314.

Figure 3B:
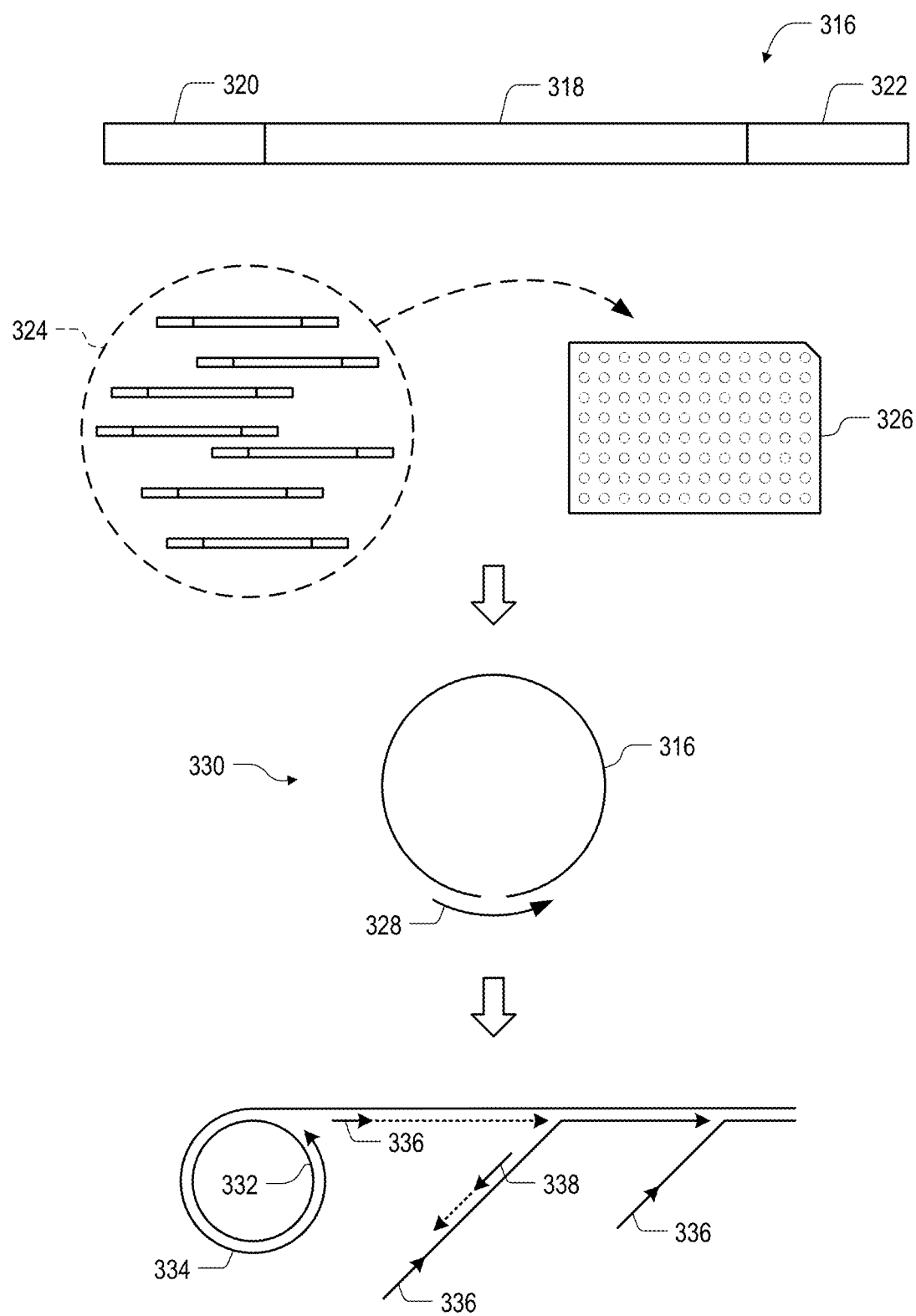
FIG. 3B is a schematic illustration of the method of FIG. 3A.

With reference to FIG. 3B, one embodiment of the method 300 begins with an ssDNA monomer 316 having the formula [A-B—C]. The monomer 316 includes: i) a B region 318 having a nucleotide barcode sequence that is unique to the monomer 316, ii) an A region 320 having a nucleotide sequence that is conserved between different monomers 316, and iii) a C region 322 having a nucleotide sequence that is conserved between different monomers 316. In some embodiments, the nucleotide sequence of the A region 320 can differ from the nucleotide sequence of the C region 322.

A plurality of different monomers 324 (which can include the monomer 316), are arrayed into a suitable article, such as a multi-well plate 326 such that each well of the multi-well plate receives a single one of the different monomers 324. In one aspect, a stochastic approach can be taken whereby the monomers 324 are diluted such that each well of the multi-well plate 326 receives either 0 or 1 of the monomers 324 to prevent any one well from receiving more than one of the monomers 324. In another aspect, a directed approach can be taken whereby each well of the multi-well plate 326 can be directly provided with a single one of the different monomers 324. For example, the different monomers 324 can be directly synthesized in each well of the multi-well plate 326 such that each well contains a different one of the monomers 324.

After arraying the monomers 324 into the multi-well plate 326, a bridge oligo 328 can then be added to each of the wells of the multi-well plate 326. The bridge oligo 328 can anneal to each of the monomers 324 to form a circular construct 330. In the present example, the example circular construct 330 includes the monomer 316, where the ends of monomer 316 are each hybridized to the bridge oligo 328 such that there is nick and no nucleotide gaps between the ends of the monomer 316 relative to the sequence of the bridge oligo 328. In this conformation, the ends of the monomer 316 can be ligated together to provide the circular template 332. The template 332 can then be amplified using, for example, MDA to provide a long ssDNA 334 having multiple contiguous repeat sequences that are complimentary to the sequence of the template 332. Second strand synthesis and subsequence amplification of the ssDNA 334 can be achieved through the addition of a reverse primer 336 and a forward primer 338 to provide a high-molecular weight, double-stranded DNA (dsDNA) tag according to the present disclosure. In one aspect, the resulting tag has the formula $X_i$[A-B—C]$_n$—$Y_j$, where n represents the number of monomer or repeat units of a particular monomer sequence (typically at least two), and X and Y represent additional nucleic acids or nucleic acid modifications made to the ends of the tag.

Figure 4:
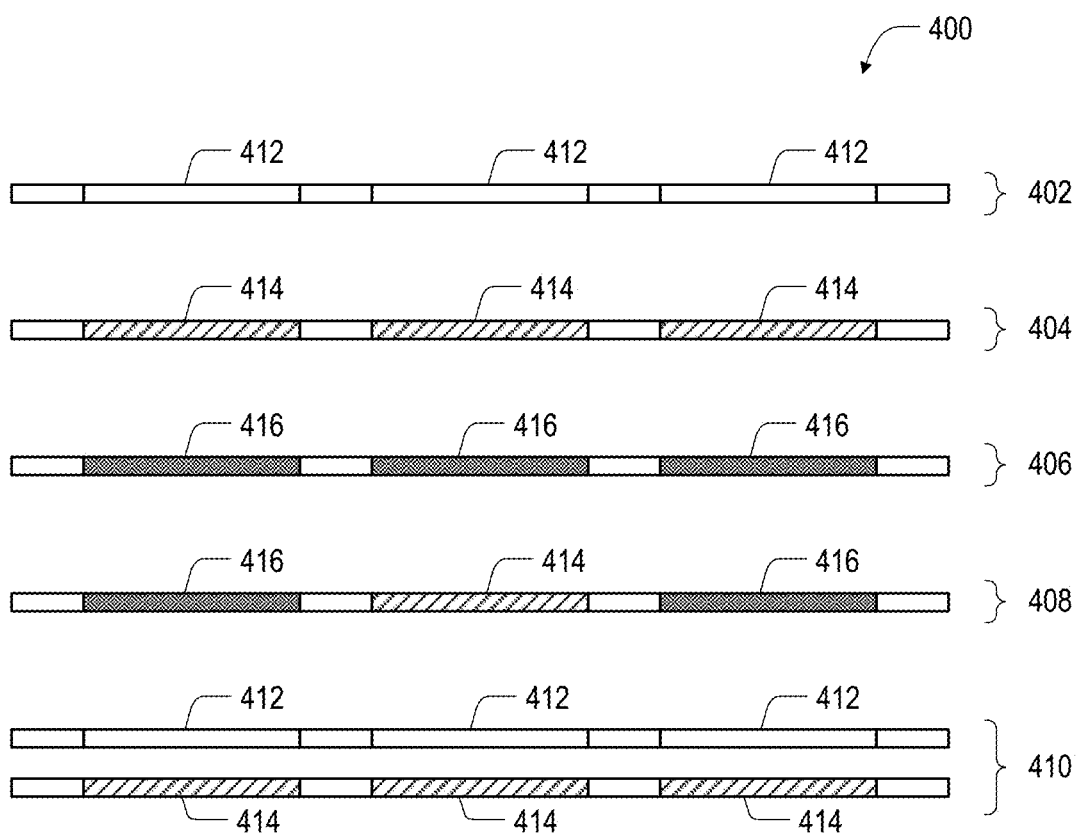
FIG. 4 is a schematic illustration of example products of the method of FIGS. 3A and 3B showing which products would pass example quality control (QC) measures.

Turning now to FIG. 4, each of wells in the multi-well plate 326 shown in FIG. 3B may yield a dsDNA tag. In order to determine whether a given well has yielded a tag comprising a single unique barcode sequence, one or more quality control measures can be taken. For example, the methods described and shown in FIGS. 3A and 3B may yield a plurality of amplification products 400 including a first amplification product 402, a second amplification product 404, a third amplification product 406, a fourth amplification product 408, and a fifth amplification product 410. Each of the first product 402, the second product 404, and the third product 406 were determined to be a composition including a single type of tag where each of the tags includes the same unique monomer sequence (i.e., the monomer includes a unique barcode sequence). For example, the first product 402 only includes repeating units including the unique monomer 412, the second product 404 only includes repeating units including the unique monomer 414, and the third product 406 only includes repeating units of the unique monomer 416.

In some cases, the methods described and shown in FIGS. 3A and 3B may yield products that are contaminated with two or more different monomers or tags. In one example, the product 408 was determined to include a heterogeneous tag sequence that includes both the monomer 414 and the monomer 416. In another example, the product 410 was determined to include a mixture of at least two different homogenous tags. That is, the product 410 is a mixture of the product 402 and the product 404. Notably, other iterations of non-homogenous products containing two or more tags, two or more monomer sequences, or a combination thereof may be possible. Moreover, sequencing-based quality control measures can additionally (or alternatively) be used to determine the fidelity of each of the monomers (e.g., presence of deletions, substitutions, or other like synthesis errors).

In some embodiments, a degenerate comprises a mixture of oligonucleotides which are synthesized in a way that allows the incorporation of all four bases (A, T, G, C) at specific oligonucleotide positions during the synthesis:

e.g., ACGCGACGNNNNNNTGGGACGA (SEQ ID NO: 108) meets criteria to be characterized as degenerate. Oligonucleotide synthesis with the exemplified sequence would produce $4^6$ oligonucleotides due to the presence of the 6 consecutive degenerate nucleotides and the use of 4 different bases (i.e., A, T, G, and C).

In some embodiments, a second step comprises or consists of annealing a bridging oligonucleotide to circularize the tag oligonucleotide and then ligate the nick. In some embodiments, a third step comprises or consists of performing MDA with strand displacement polymerases such as phi29 (φ29) DNA polymerase or Bst DNA polymerase. It is contemplated that the use of such polymerases is advantageous due to proof-reading characteristics and high-fidelity performance of such polymerases. In some embodiments, a fourth step comprises or consists of confirming tag identity and purity by next generation sequencing of at least one MDA product.

In some embodiments, tags are produced using long-range PCR. In some embodiments, tags are produced according to the exemplary method shown in FIGS. 5A and 5B. In some embodiments, provided tags are produced using a high fidelity DNA polymerase with proof-reading activity (e.g., φ29).

Figure 5A:
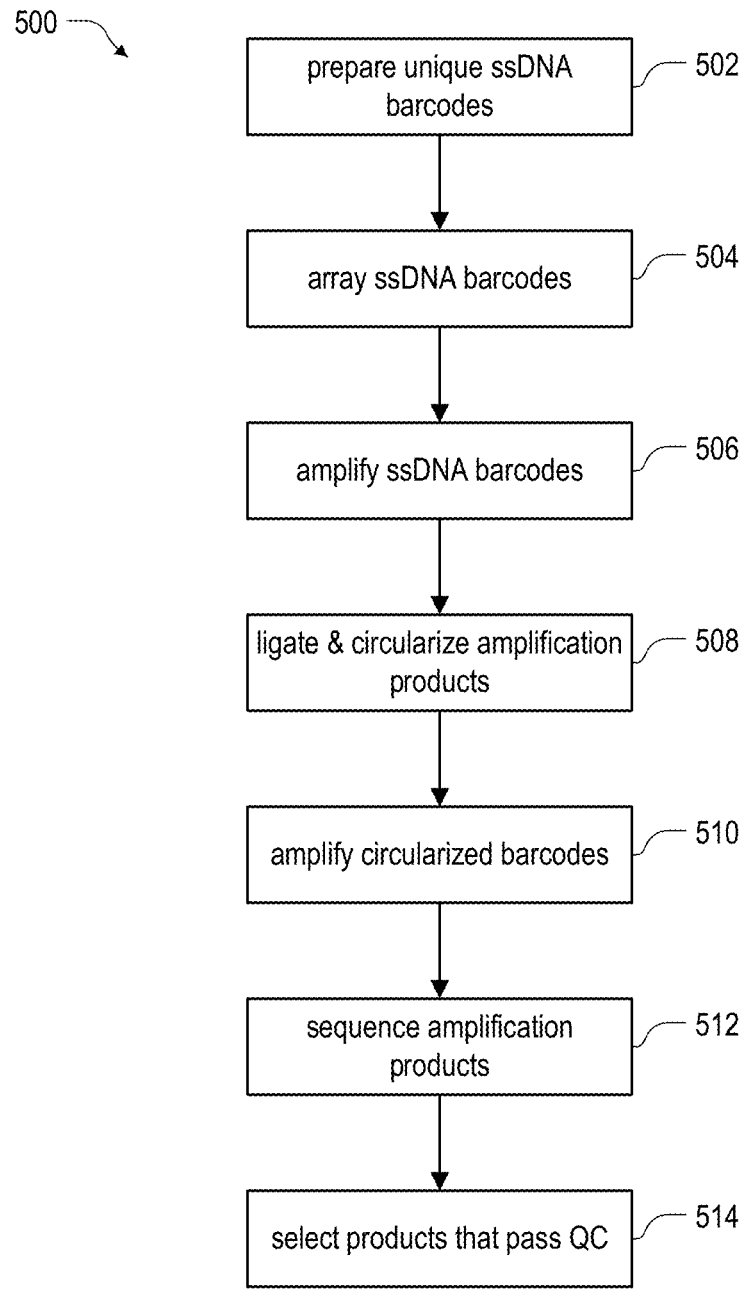
FIG. 5A is a second example of a high-throughput method of producing high-molecular weight sample tracking DNA tags according to the present disclosure.

Turning to FIG. 5A, one example method 500 of producing a tag includes a step 502 of preparing unique single stranded DNA (ssDNA) monomers. In a step 504, the monomers are arrayed, for example, into a multi-well plate (e.g., a standard 96 well plate). Thereafter, each of the ssDNA monomers can be amplified in a step 506. The amplified tag monomers can then be ligated together in an end-to-end fashion to provide a multimer composed of individual tag monomers in a step 508. The step 508 can further include circularizing (e.g., via ligation) the tag multimers to provide a set of circular templates. In one aspect, the ligation and circularization can occur in a single concerted reaction step, whereas in another aspect, the ligation and circularization can occur in sequential reaction steps. In a step 510, the circularized products can be amplified, and the amplification of the circularized multimers can be monitored using, for example, fluorescence-based qPCR, or another suitable technique. In one aspect, it may be useful to monitor amplification as a quality control measure to determine which of the monomers may have been successfully amplified. In a step 512, the products produced from amplification in the step 510 can be sequenced to further confirm successful amplification and to ensure that each of the tags was not contaminated with another one of the tags or monomers. Those products that pass the various quality control measures can be selected for further use in a step 514.

Figure 5B:
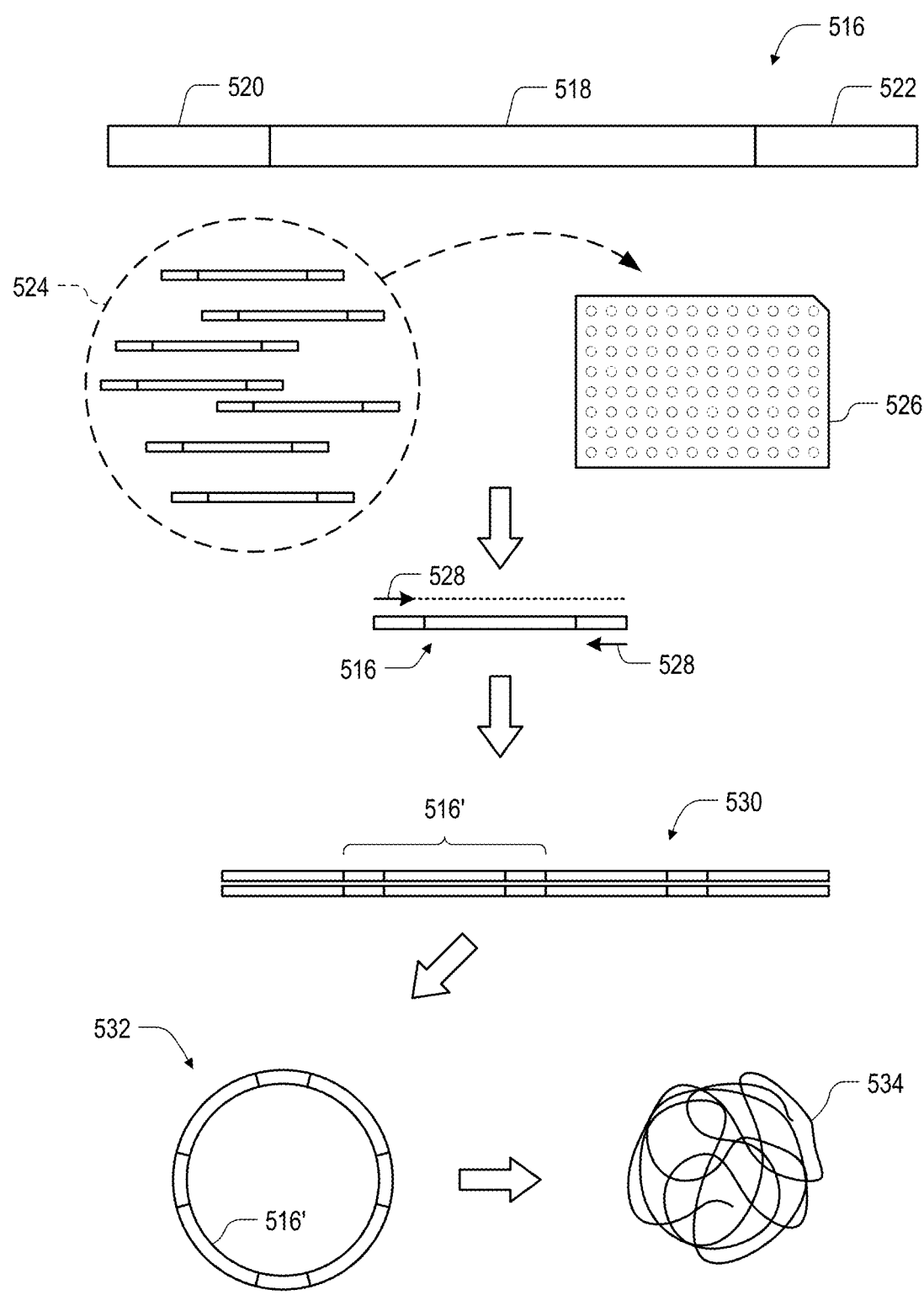
FIG. 5B is a schematic illustration of the method of FIG. 5A.

With reference to FIG. 5B one embodiment of the method 500 begins with an ssDNA monomer 516 having the formula [A-B—C]. The monomer 516 includes: i) a B region 518 having a nucleotide barcode sequence that is unique to the monomer 516, ii) an A region 520 having a nucleotide sequence that is conserved between different monomers 516, and iii) a C region 522 having a nucleotide sequence that is conserved between different monomers 516. In some embodiments, the nucleotide sequence of the A region 520 can differ from the nucleotide sequence of the C region 522.

A plurality of different monomers 524 (which can include the monomer 516), are arrayed into a suitable article, such as a multi-well plate 526 such that each well of the multi-well plate receives a single one of the different monomers 524. In one aspect, a stochastic approach can be taken whereby the monomers 524 are diluted such that each well of the multi-well plate 526 receives either 0 or 1 of the monomers 524 to prevent any one well from receiving more than one of the monomers 524. In another aspect, a directed approach can be taken whereby each well of the multi-well plate 526 can be directly provided with a single one of the different monomers 524. For example, the different monomers 524 can be directly synthesized in each well of the multi-well plate 526 such that each well contains a different one of the monomers 524.

After arraying the monomers 524 into the multi-well plate 526, a set of primers 528 can then be added to each of the wells of the multi-well plate 526. The primers 528 can anneal to each of the monomers 524 to form a plurality of copies of the monomers 524. In the present example, the monomer 516 is shown as being amplified by the primers 528. Copies of the now double-stranded monomer 516' can then be ligated together to form an intermediate linear construct 530 composed of a plurality of copies or monomers of the monomer 516'. The linear construct 530 can be circularized and ligated to provide the circular, double-stranded template 532 that includes a number of repeat units of the monomer 516'. The template 532 can then be amplified using, for example, MDA to provide a long ssDNA tag 534 having multiple contiguous repeat sequences of the template 532, such that tag 534 has the formula $X_i$[A-B—C]$_n$—$Y_j$. In one aspect, n represents the number of monomers or repeat units of a particular monomer sequence (typically at least two), and X and Y represent additional nucleic acids or nucleic acid modifications made to the ends of the tag 534.

In some embodiments, spike-in tags are used for determining and correcting sample indexing barcode cross-talk. For example, sample indexing barcodes (also known as indexes in, e.g., Illumina sequencing platforms, which may have, e.g., 24 distinct indexes) are typically included as part of sequencing analysis processing. The indexes are used to simultaneously sequence multiple libraries as a mixture, with subsequent partitioning of the resultant sequence, based on a sample-specific index. Such barcodes are often comprised of short length nucleic acids, such that the edit distance between indexing barcodes is small. This increases the statistical likelihood that a given barcode could be falsely identified as another barcode due to cumulative sequencing changes during processing. Spike-in tags according to the present invention are useful to overcome and/or correct for this problem for sequence analysis.

In some embodiments, tags according to the present invention are prepared at a limiting dilution, wherein the use of a limiting dilution comprises a degenerate oligonucleotide and such a dilution would make possible production of almost entirely unique barcodes (e.g., one unique tag signature for every sample ever sequenced).

In some embodiments, the use of a degenerate oligonucleotide allows production of many unique oligonucleotides with a single oligonucleotide synthesis. It will be appreciated that, compared to other known methods, the present invention provides advantages such as cost and labor saving measure, by use of degenerate oligonucleotides and limiting dilutions. To give an example for an oligonucleotide of sequence NNNN, $4^4$ (i.e., 256) oligonucleotides are produced in a mixture. Then, using the limiting dilution approach, to dilute to only approximately a single oligonucleotide per well (if, e.g., using a well-plate format), $4^4$ oligonucleotides can be obtained without having to perform $4^4$ syntheses.

Those of ordinary skill in the art, reading the present disclosure, will appreciate that provided tags may be utilized in any of a variety of assays, and with any of a variety of platforms for such assays. In particular, provided tags are useful in any high-throughput (e.g., NGS) sequencing platform. Still further, provided tags are useful in long-read sequencing applications (e.g., PACBIO, OXFORD NANOPORE, GENIA).

Combinatorial Sample Tagging

In some embodiments, combinatorial sample tagging is used in accordance with the present invention. Not wishing to be bound to any particular theory, it is possible that with as few as 384 tags and using three or four tags per sample, unique combinations allowed for each of three and four tags per sample are: C(384,3)=9,363,584 and C(384,4)=891,881,376 unique combinations. In some embodiments, such combinations allow a sequencing core to uniquely tag every sample that moves through its facility. Moreover, in combination with another set of 384 tags, it is possible to uniquely tag every individual on the planet.

Kits

The invention also contemplates kit formats which include a package unit having one or more containers containing at least one tag according to the present invention. In some embodiments, kits comprise containers of various reagents used for tag reconstitution or dilution. In some embodiments, kits comprise containers of various reagents used for e.g., PCR, processing and/or sequencing analysis. In some embodiments, kits may also contain at least one or more of buffers, instructions, and controls.

Methods of Tag Use

A variety of uses for the tags according to the present invention are contemplated. In some embodiments, a sample is tagged by contacting a sample with at least one or more tags. In some embodiments, zero or at least one or more tags are spiked in to vessels containing samples before, during, or immediately after sample collection. In some embodiments zero or at least one or more tags are spiked in to samples before, during or after processing. In some embodiments, 0, 1, or more tags are spiked in to samples before or after separation. In some embodiments, 0, 1, or more tags are spiked in to samples before or after purification. In some embodiments, 0, 1, or more tags are spiked in to a vessel where downstream processing and/or analysis is occurring. It is appreciated that some embodiments may allow the use of synthetic spike-in tags as a means to determine and correct sequencing errors. Such determination and correction is based upon, e.g., high fidelity production of known and variable sequences, wherein one can reasonably be confident that when mismatches are observed following sequences, between observed and expected sequence alignments, it can be determined with high degrees of confidence that such mismatches are attributable to the chemistry and/or base-calling of the sequencing process used to analyze the sample.

The present invention appreciates, e.g., that a benefit of the repeating unit arrangement of the tag includes that many copies of each tag will be analyzed e.g., sequenced, even with a small percentage of tag spiked into a given sample.

In some embodiments, error correction might, e.g., be used if a specific, systemic type of error that a sequencing process makes e.g., G>C mutation would allow for use in development of statistical models to weight SNP calling algorithms against this type of false positive result.

In some embodiments, the tag sequence may be used to assess how good a sequencing process is at sequencing a specific DNA motif/sequence type (e.g., repeats, hairpins etc.), or reference sequences use in analysis platforms (e.g., phiX genome in Illumina sequencing). It is appreciated that the synthetic sequences of the present invention provide an advantage for use in comparison against platforms that use controls derived from genomes of known organisms.

EXAMPLES

The following Examples are meant to be illustrative and are not intended to be limiting in any way.

Example 1

Production of High-molecular Weight (HMW) Tags

High-molecular weight double-stranded DNA tags were produced using the components and methodologies described below.

Single defined 60-mer DNA oligos were designed with priming constant sections (region A) and (region C) and a tag region (region B; marked either as Tag 1 or Tag 2). Oligos used to produce different spike-in tags were designed to have identical constant regions A and C, but different tag or B regions (i.e., Tag 1 and Tag 2).

A first oligo (RCA_Tag_1) including the Tag 1 B region had the sequence:
RCA_Tag_1: ATGCACAAGGCCGACAATAGGCACGAGCATAGAAGTTAGTACGTAGCGTGGTCGCATAAG (SEQ ID NO:1.

The first oligo (SEQ ID NO:1) included an A region, B region, and C region having the following sequences:
A region: ATGCACAAGGCCGACAATA (SEQ ID NO:2).
B region (Tag 1): GGCACGAGCATAGAAGTTAGTA (SEQ ID NO:3.
C region: CGTAGCGTGGTCGCATAAG (SEQ ID NO: 4)

A second oligo (RCA_Tag_2) including the Tag 2 B region had the sequence:
RCA_Tag 2: ATGCACAAGGCCGACAATAGAGTAGGACAATGATTGAGAAGCGTAGCGTGGTCGCATAAG (SEQ ID NO: 5)

The second oligo (SEQ ID NO: 5) included the A region (SEQ ID NO: 2) and C region (SEQ ID NO: 4) from the first oligo (SEQ ID NO: 1). However, the second oligo (SEQ ID NO: 5) included a different B region having the Tag 2 sequence:
B region (Tag 2): GAGTAGGACAATGATTGAGAAG (SEQ ID NO: 6).

The first oligo (SEQ ID NO:1) and the second oligo (SEQ ID NO:5) were circularized using a bridge oligo (RCA_Tag_Bridge) having the sequence:
Bridge oligo (RCA_Tag_Bridge): CCTTGTGCATCT-TATGCGAC (SEQ ID NO:7)

The nick was ligated to create a 60 base ssDNA circle.

Forward and reverse primers (RCA_PCR_F and RCA_PCR_R respectively) and φ29 DNA polymerase were used to amplify the oligo by MDA. The forward and reverse primers had the following sequences:
Forward primer (RCA_PCR_F): ATGCACAAGGCCGACAATA (SEQ ID NO:8)
Reverse primer (RCA_PCR_R): CTTATGCGACCACGC-TACG (SEQ ID NO:9)

Double strandedness was tested by cutting with the restriction enzyme HaeIII (recognition sequence=GGCC)

The first oligo (SEQ ID NO:1) and the second oligo (SEQ ID NO:5) were combined individually and annealed with the bridge oligo (SEQ ID NO:7) to form circular structures (e.g., 330, FIG. 3B), and the nick was ligated using T4 DNA ligase. Next, an excess of primer RCA_PCR_F (SEQ ID NO:8) and RCA_PCR_R (SEQ ID NO:9) was added. The bridge oligo (SEQ ID NO:7) primes ssDNA synthesis using φ29 or another strand displacing DNA polymerase.

The methods of the present example produced a long single strand with the repeating unit containing the constant and tag regions. For example, an amplification product including two repeat units (i.e., [A-B—C]$_2$) would have the sequence:
CTTATGCGACCACGCTACGTACTAACTTC-TATGCTCGTGCCTATTGTCGGCCTTGTGCATC TTATGCGACCACGCTACGTACTAACTTC-TATGCTCGTGCCTATTGTCGGCCTTGTGCAT (SEQ ID NO:10)

RCA_PCR_F primer (SEQ ID NO:8) was annealed to the resulting ssDNA amplification products (e.g., SEQ ID NO:10), enabling the polymerase to synthesize the reverse strand. Following this, the RCA_PCR_R primer (SEQ ID NO:9) primed DNA synthesis on the newly synthesized strand. The combination of the circular template (SEQ ID NO:1; SEQ ID NO:5), bridge oligo (SEQ ID NO:7), RCA_PCR_F (SEQ ID NO:8) and RCA_PCR_R (SEQ ID NO:9) together with a strand displacing DNA polymerase resulted in exponential, isothermal, production of a long, double stranded high-molecular weight DNA with a repeating structure (e.g., SEQ ID NO:10).

In particular, RCA_Tag_1 (SEQ ID NO:1) and RCA_Tag_Bridge (SEQ ID NO:7) oligos were resuspended in 10 mM Tris-Cl pH 8.0 to 100 pmol/μl (μM) to provide oligo stock solutions.

Oligo stock solutions were diluted 1 in 100 with annealing buffer (10 mM Tris-Cl 1 mM EDTA, 10 mM NaCl)

Annealing was carried out with 10 μl (400 ng, 10 pmol) of RCA_Tag_1 (SEQ ID NO:1) and RCA_Tag_Bridge (SEQ ID NO:7) oligo using standard annealing conditions (90° C. for 30 seconds followed by ramp down to 4° C. at 0.2 degrees per second) in a 20 μl reaction volume. The concentration was calculated to be 0.5 pmol/μl or 30 ng/μl.

In a next step, 2 μl (60 ng) of the annealed oligo were ligated using the KAPA rapid ligation kit in a 20 μl reaction mix containing 10 μl 2× ligase buffer, 2 μl template (1 pmol), 1 μl T4 ligase (25U), 7 μl water at room temperature (RT) for 15 min. No cleanup was performed. Template concentration was calculated to be 0.05 pmol/μl, or 3×10$^{10}$ copies/μl.

Next, 1 μl of the ligation product was diluted into 300 μl 10 mM Tris-Cl resulting in 1×10$^8$ copies/μl (100-200 pg/μl).

MDA was performed using a dilution series of the circular template as detailed in the following steps.

A 20 μl amplification reaction mixture with φ29 polymerase (New England Biolabs, catalog number M0269S) was prepared as follows: 0.5 μl φ29 (5U), 2 μl 10× φ29 buffer, 0.2 μl 100× BSA, 10 mM dNTPs (0.4 μl-200 μM each), 1 μl 20× KAPA SYBR GREEN dye, water up to 20 μl. For amplification, the reaction mixture was held at 30° C. for 400 minutes with fluorescence measurements collected every 2 minutes using the green channel for a total of 200 reads.

Primer RCA_PCR_F (SEQ ID NO:8), RCA_PCR_R (SEQ ID NO:8), or both were added to the reaction to a final concentration of 0.5 μM. No template reactions (NTC) and no primer control reactions were also included.

Figure 7:
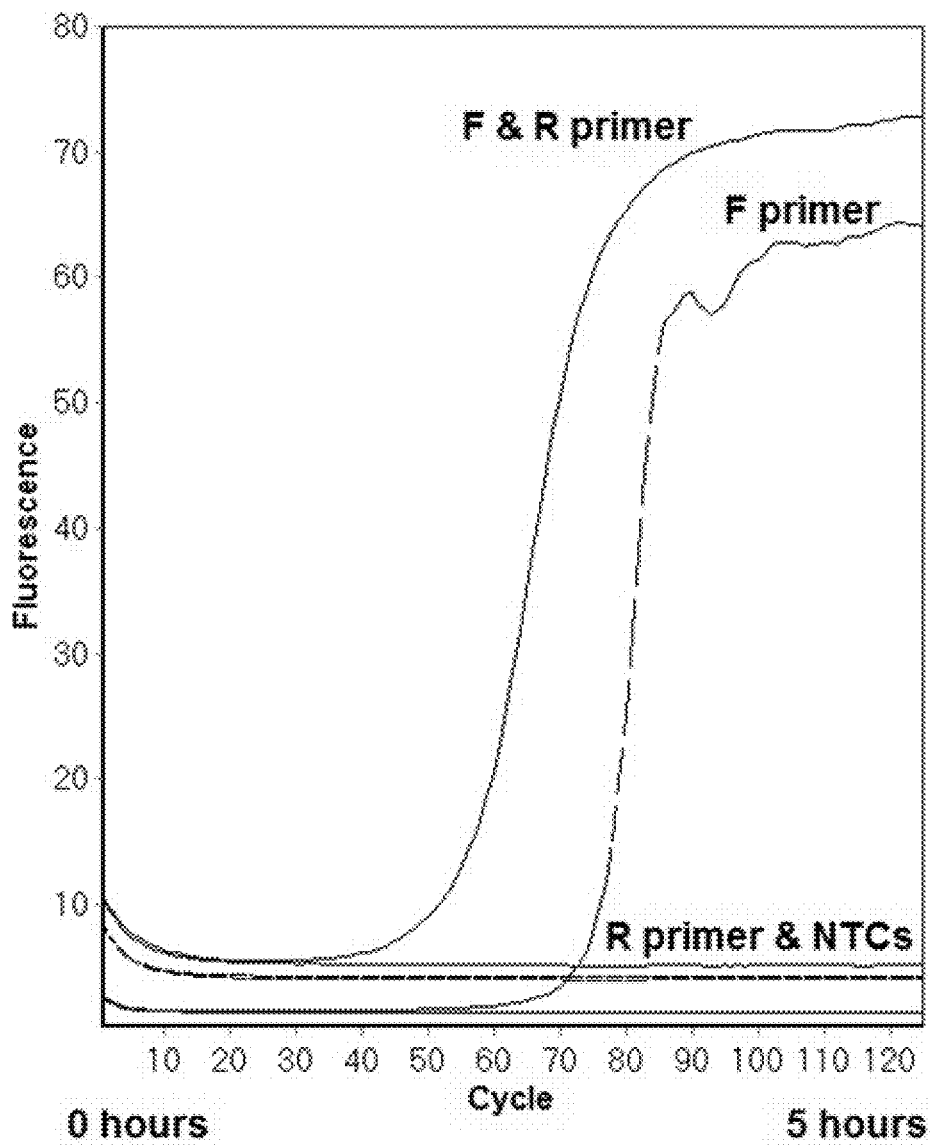
FIG. 7 shows results of real-time amplification of an example high-molecular weight tag. Addition of forward (F) primer (RCA_PCR_F (SEQ ID NO:8)) and reverse (R) primer (RCA_PCR_R (SEQ ID NO:9)) enabled exponential amplification that plateaus after 3 hours. Addition of forward primer alone is also sufficient, whereas addition of the reverse primer alone was not sufficient for multiple displacement amplification to occur. No template control (NTC) reactions produced no amplification product.

Amplification was monitored using SYBR green on a Qiagen Rotorgene instrument. The reaction was allowed to proceed for 12 hours to completion (FIG. 7).

DNA was purified using 1× Ampure XP beads and eluted in 10 mM Tris-Cl, quantified using spectrophotometry (Nanodrop 1000), and normalized to 10 ng/μl.

Figure 6:
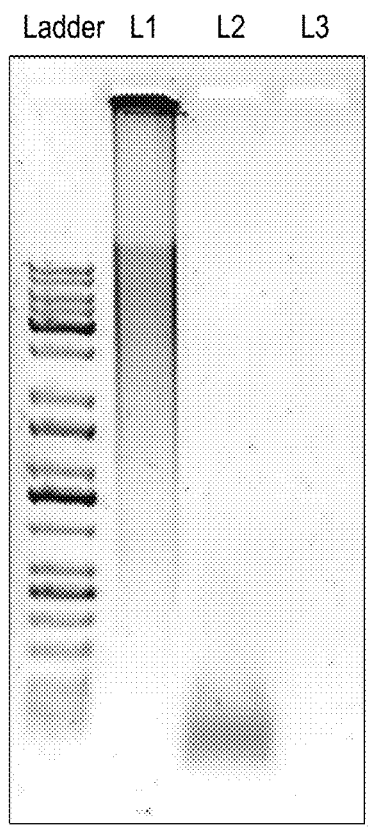
FIG. 6 is an image of an agarose gel following gel electrophoresis of digested and undigested high molecular weight tags prepared with φ29 DNA polymerase. From left to right, the gel lanes were loaded with a standard DNA ladder (Ladder), undigested purified HMW Tag 1 DNA (L1), Tag 1 DNA digested with HaeIII (L2), and a no template control (L3).

An aliquot of the resulting DNA was digested with the HaeIII restriction enzyme to confirm that the resulting DNA was fully double-stranded. The product of the digest was analyzed by gel electrophoresis (FIG. 6).

Allowing the MDA reaction to run to completion at 30° C. produces >3 μg of purified product (equivalent to several thousand sequencing reactions).

Product appears to migrate as high-molecular weight DNA on agarose gel (majority resides in the well).

HMW material digested with HaeIII restriction enzyme (single site per repeat) resolves into low molecular weight material. Therefore the majority of the material appears to be double stranded DNA.

NTCs produce no detectable product after overnight incubation.

Amplification with forward (RCA_PCR_F) and reverse (RCA_PCR_R) primers as well as forward primer alone is exponential.

Reactions without unligated circles make no product.

Reaction plateaus after 3 hours.

Example 2

Production of Sequencing Libraries e.g., for Illumina Platforms where Two Libraries were Tagged with Tag 1

A known mass of Tag 1 from Example 1 was spiked into a known mass of genomic DNA (gDNA) from *Bordetella pertussis* and an Illumina compatible library was created with the KAPA Hyper Plus library preparation kit.

The spiked-in library was sequenced and it was determined whether Tag 1 was detectable at predicted abundance.

Tag 1 HMW material was diluted to 1 ng/μl and 20 pg/μl in 10 mM Tris-Cl. Purified Tag 1 MDA product was added at 2% by mass into 50 ng or 1 ng of *Bordetella pertussis* gDNA (i.e., 1 ng and 20 pg of MDA product, respectively; Library 1 and 2).

Libraries from *Clostridium difficile* gDNA (50 ng and 1 ng) without spike-in tags were built concurrently (Libraries 3 and 4).

Illumina-compatible libraries were created using the KAPA Hyper Plus library preparation kit (30 minute shearing of DNA followed by A-tailing and adapter ligation as per the manufacturer's instructions).

Figure 8:
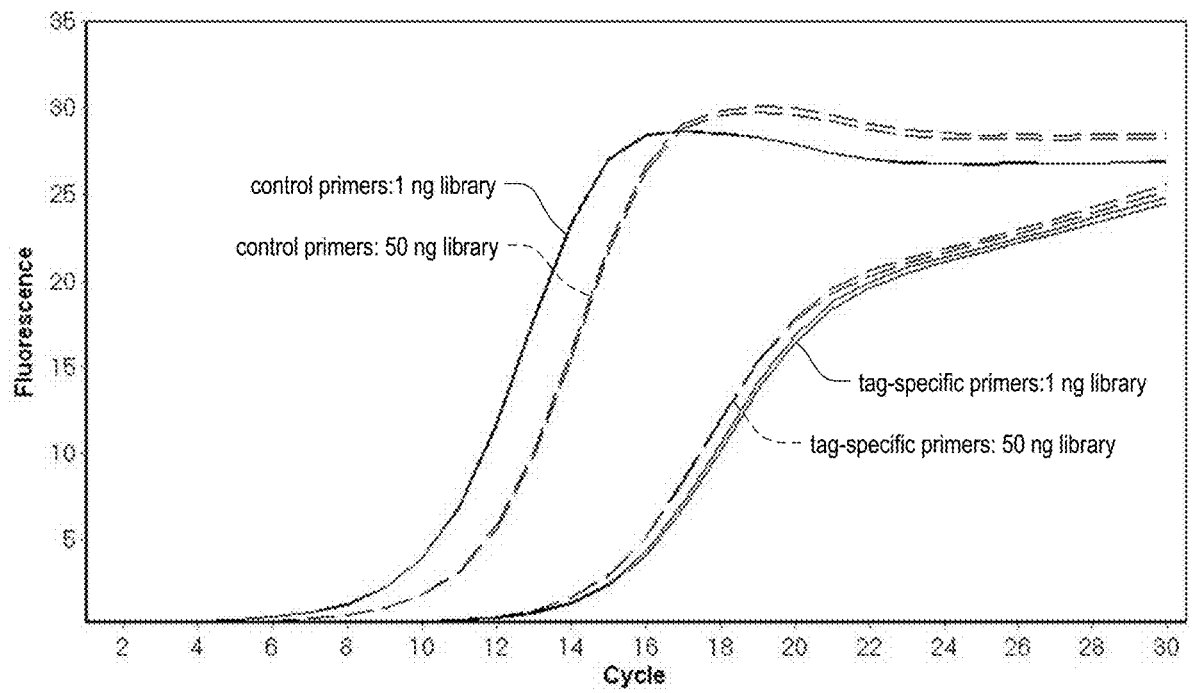
FIG. 8 shows results of real-time PCR for example sequencing libraries prepared from *Bordetella pertussis* DNA and spiked-in high-molecular weight sample tracking tag. Analysis was performed on sample by amplification i) using library-specific primers from the KAPA Library Quantification Kit (LQK) to detect 50 ng or 1 ng of *B. pertussis* library DNA, and ii) using tag-specific primers to detect the 2% spike-in Tag 1 DNA. Both amplified (50 ng) and unamplified (1 ng) libraries exhibited the same ratio of tag-derived library molecules to library molecules.

After library preparation, 50 ng libraries were used without PCR amplification, while 1 ng libraries were amplified for 12 cycles to yield the same amount of end-product ligated library as the 50 ng libraries.

qPCR was performed on libraries with spike-in specific primers RCA_PCR_F (SEQ ID NO: 8) and RCA_PCR_R (SEQ ID NO: 8) to determine whether spike-in tag material became part of the library and whether the amplified library retained the same ratio of tag to library (FIG. 8).

Libraries were pooled and sequenced on an Illumina MiSeq platform.

Trimmed Illumina sequences were aligned to Tag 1 sequence to determine the percentage of reads originating from Tag 1 (FIG. 9). With reference to FIG. 9, the A region of the repeating [A-B—C] monomer sequence is indicated at 900, the B region at 902 and the C region at 904*a* and 904*b*. Notably, the C region is indicated at both ends of the illustrated reads due to the repeating nature of the tag sequence.

Following sequencing of the four libraries, the reads to the Tag 1 sequence were mapped using blastn and the percentage of Tag 1-derived reads were counted. The number of Tag 1: matching reads was as follows:

Library 1: 4000 reads (0.8% of total)
Library 2: 6500 reads (1.3% of total)
Library 3: 0 reads (0% of total)
Library 4: 0 reads (0% of total)

qPCR showed that libraries spiked with 2% of Tag 1 HMW material retained an equal proportion of Tag 1-derived library inserts despite undergoing 12 cycles of library amplification (FIG. 8).

Following de-multiplexing, at least 500,000 reads were obtained for each of library 1 through 4.

The Tag 1-derived reads were regular in structure, i.e., the variable region is flanked by constant regions (FIG. 9).

The presence of the repeating unit of [(constant A regions)–(variable B region)–(constant C region)] showed that the HMW Tag 1 DNA was a concatemer.

Tag 1 HMW contains relatively little error, with only a few mismatches observed, which may not be attributable to sequencing error.

In one aspect, spiking in of Tag 1 HMW DNA allowed the identification of tagged libraries following sequence analysis. Further, spiking in Tag 1 HMW DNA was effective at very low (1 ng) and high (50 ng) amounts of template DNA. In another aspect, Tag 1 DNA was retained in PCR-amplified NGS libraries. In yet another aspect, the mass ratio of spike-in to sample DNA was reflected by the percentage of Illumina short reads mapping to Tag 1 in the libraries spiked with Tag 1 HMW DNA.

Example 3

Spiking in Two Distinct Tags to Demonstrate Ability to Uniquely Identify Tagged Samples The HMW DNA spike-in tags were prepared from RCA_Tag_1 (SEQ ID NO:1) and RCA_Tag_2 (SEQ ID NO: 5) according the protocol described in Example 1, thereby resulting in spike-in tags Tag 1 and Tag 2, respectively.

Spiking in Tag 1 and Tag 2 into a grid of libraries was tested according to the experimental design detailed in Table 1.

TABLE 1

| | Pool 1 (DOP = 24) | | | Pool 2 (DOP = 24) | | |
|---|---|---|---|---|---|---|
| | Fragment size (bp) | | | | | |
| | 300 (shear) | | | 500 (shear) | | |
| | Spike-in (%) | | | | | |
| ID/DNA (200 ng) | 1.00 | 0.10 | 0.01 | 1.00 | 0.10 | 0.01 |
| A/*Chlamydia* | Tag 1 | Tag 2 | Tag 1 | Tag 2 | Tag 1 | Tag 2 |
| B/*Chlamydia* | Tag 2 | Tag 1 | Tag 2 | Tag 1 | Tag 2 | Tag 1 |
| C/*M. ruber* | Tag 1 | Tag 2 | Tag 1 | Tag 2 | Tag 1 | Tag 2 |
| D/*M. ruber* | Tag 2 | Tag 1 | Tag 2 | Tag 1 | Tag 2 | Tag 1 |
| E/*E. coli* | Tag 1 | Tag 2 | Tag 1 | Tag 2 | Tag 1 | Tag 2 |
| F/*E. coli* | Tag 2 | Tag 1 | Tag 2 | Tag 1 | Tag 2 | Tag 1 |
| G/*P. hepatus* | Tag 1 | Tag 2 | Tag 1 | Tag 2 | Tag 1 | Tag 2 |
| H/*P. hepatus* | Tag 2 | Tag 1 | Tag 2 | Tag 1 | Tag 2 | Tag 1 |

Microbial genomic DNA samples were combined with 1%, 0.1% and 0.01% by mass of either of DNA tag Tag 1 or Tag 2. DNA was fragmented by acoustic shearing to an average size of 300 bp or 500 bp, and Illumina-compatible libraries were constructed with different indexes, according to the procedures described in Example 2. Sequencing was performed on an Illumina MiSeq instrument. The number of reads matching each tag were counted in each of the sequenced libraries and results reported as parts per million (ppm).

Tables 2 and 3 illustrate that libraries spiked with DNA tags Tag 1 and Tag 2 could be identified based on the number of reads mapping to the respective reference. All results shown in Tables 2 and 3 are shown as percentages unless indicated otherwise. Further, results in Tables 2 and 3 correspond to the experimental design shown in Table 1.

TABLE 2

Percent Reads mapped to Tag 1 DNA

| | Fragment size (bp) | | | | | |
|---|---|---|---|---|---|---|
| | 300 (shear) | | | 500 (shear) | | |
| | Spike-in (%) | | | | | |
| ID/DNA (200 ng) | 1.00 | 0.10 | 0.01 | 1.00 | 0.10 | 0.01 |
| A/*Chlamydia* | 0.405 | 0.000 | 0.002 | 0.001 | 0.048 | 0.000 |
| B/*Chlamydia* | 0.001 | 0.038 | 0.000 | 0.473 | 0.000 | 0.003 |
| C/*M. ruber* | 0.231 | 0.000 | 0.002 | 0.000 | 0.036 | 0.000 |
| D/*M. ruber* | 0.002 | 0.027 | 0.000 | 0.377 | 0.000 | 0.002 |
| E/*E. coli* | 0.302 | 0.000 | 0.002 | 0.002 | 0.035 | 0.000 |
| F/*E. coli* | 0.000 | 0.029 | 0.000 | 0.381 | 0.000 | 0.002 |
| G/*P. hepatus* | 0.246 | 0.000 | 0.002 | 0.001 | 0.025 | 0.000 |
| H/*P. hepatus* | 0.000 | 0.025 | 0.000 | 0.238 | 0.000 | 0.002 |

TABLE 3

Percent reads mapped to Tag 2 DNA

| | Fragment size (bp) | | | | | |
|---|---|---|---|---|---|---|
| | 300 (shear) | | | 500 (shear) | | |
| | Spike-in (%) | | | | | |
| ID/DNA (200 ng) | 1.00 | 0.10 | 0.01 | 1.00 | 0.10 | 0.01 |
| A/*Chlamydia* | 0.000 | 0.001 | 0.000 | 0.025 | 0.000 | 0.000 |
| B/*Chlamydia* | 0.019 | 0.000 | 0.000 | 0.000 | 0.003 | 0.000 |
| C/*M. ruber* | 0.000 | 0.001 | 0.000 | 0.017 | 0.000 | 0.000 |
| D/*M. ruber* | 0.012 | 0.000 | 0.000 | 0.000 | 0.002 | 0.000 |

TABLE 3-continued

| | Percent reads mapped to Tag 2 DNA | | | | | |
|---|---|---|---|---|---|---|
| | Fragment size (bp) | | | | | |
| | 300 (shear) | | | 500 (shear) | | |
| | Spike-in (%) | | | | | |
| ID/DNA (200 ng) | 1.00 | 0.10 | 0.01 | 1.00 | 0.10 | 0.01 |
| E/*E. coli* | 0.000 | 0.001 | 0.000 | 0.019 | 0.000 | 0.000 |
| F/*E. coli* | 0.016 | 0.000 | 0.000 | 0.000 | 0.002 | 0.000 |
| G/*P. hepatus* | 0.000 | 0.001 | 0.000 | 0.013 | 0.000 | 0.000 |
| H/*P. hepatus* | 0.012 | 0.000 | 0.000 | 0.000 | 0.001 | 0.000 |

In this experiment, only perfect matches to the reference were allowed, which accounts for a less than perfect correlation between spike-in ratio and number of reads observed for each tag.

Tag 1 and Tag 2 HMW material was successfully used to tag whole genome sequencing libraries from a variety of microorganisms at different percentages of spike-in.

Example 4

Designing and Sequencing Tags Produced by Multiple Polymerases

An additional 14 tags were designed, which have an edit distance of >8 in the variable region. HMW DNA tags were synthesized from a subset of these tags using φ29 DNA polymerase and Bst DNA polymerase. The HMW tags were sequenced using an Illumina MiSeq platform to test for purity and sequence concordance. The tags had the following monomer (i.e., [A-B—C]$_1$) sequences (B regions are underlined):

RCA_Tag_3:
(SEQ ID NO.: 11)
ATGCACAAGGCCGACAATA<u>ACTTTGAGCAAACGTCGTCTGT</u>CGTAGCGTG

GTCGCATAAG

RCA_Tag_4
(SEQ ID NO.: 12)
ATGCACAAGGCCGACAATA<u>TAAGCACCTTCTGTGCGTAATG</u>CGTAGCGTG

GTCGCATAAG

RCA_Tag_5
(SEQ ID NO.: 13)
ATGCACAAGGCCGACAATA<u>TTACGACGTAGCTCCGATTTAG</u>CGTAGCGTG

GTCGCATAAG

RCA_Tag_6
(SEQ ID NO.: 14)
ATGCACAAGGCCGACAATA<u>AGTGAGACTGATCCTTCTAGCT</u>CGTAGCGTG

GTCGCATAAG

RCA_Tag_7
(SEQ ID NO.: 15)
ATGCACAAGGCCGACAATA<u>CTCTGATTCGAATGCAAGTCGT</u>CGTAGCGTG

GTCGCATAAG

RCA_Tag_8
(SEQ ID NO.: 16)
ATGCACAAGGCCGACAATA<u>GGTAGCATCAATTTAGCTCGTC</u>CGTAGCGTG

GTCGCATAAG

RCA_Tag_9
(SEQ ID NO.: 17)
ATGCACAAGGCCGACAATA<u>CACGGCTATTTCACGTTGTAGA</u>CGTAGCGTG

GTCGCATAAG

RCA_Tag_10
(SEQ ID NO.: 18)
ATGCACAAGGCCGACAATA<u>GCCGGAACTCTTTTAAGGCATT</u>CGTAGCGTG

GTCGCATAAG

RCA_Tag_11
(SEQ ID NO.: 19)
ATGCACAAGGCCGACAATA<u>GCGCCAATTATGTGGACTACTT</u>CGTAGCGTG

GTCGCATAAG

RCA_Tag_12
(SEQ ID NO.: 20)
ATGCACAAGGCCGACAATA<u>CGTCACCTGTAGAAATGTCGTT</u>CGTAGCGTG

GTCGCATAAG

RCA_Tag_13
(SEQ ID NO.: 21)
ATGCACAAGGCCGACAATA<u>GAGCAGGTCCTATCATTATCTG</u>CGTAGCGTG

GTCGCATAAG

RCA_Tag_14
(SEQ ID NO.: 22)
ATGCACAAGGCCGACAATA<u>TCATTCATCGATTGGCAGGTAC</u>CGTAGCGTG

GTCGCATAAG

RCA_Tag_15
(SEQ ID NO.: 23)
ATGCACAAGGCCGACAATA<u>TCGCTGAGACGGTTCTAAATCT</u>CGTAGCGTG

GTCGCATAAG

RCA_Tag_16
(SEQ ID NO.: 24)
ATGCACAAGGCCGACAATA<u>CATTGACGGGTTAGATATCCTC</u>CGTAGCGTG

GTCGCATAAG

Figure 10:
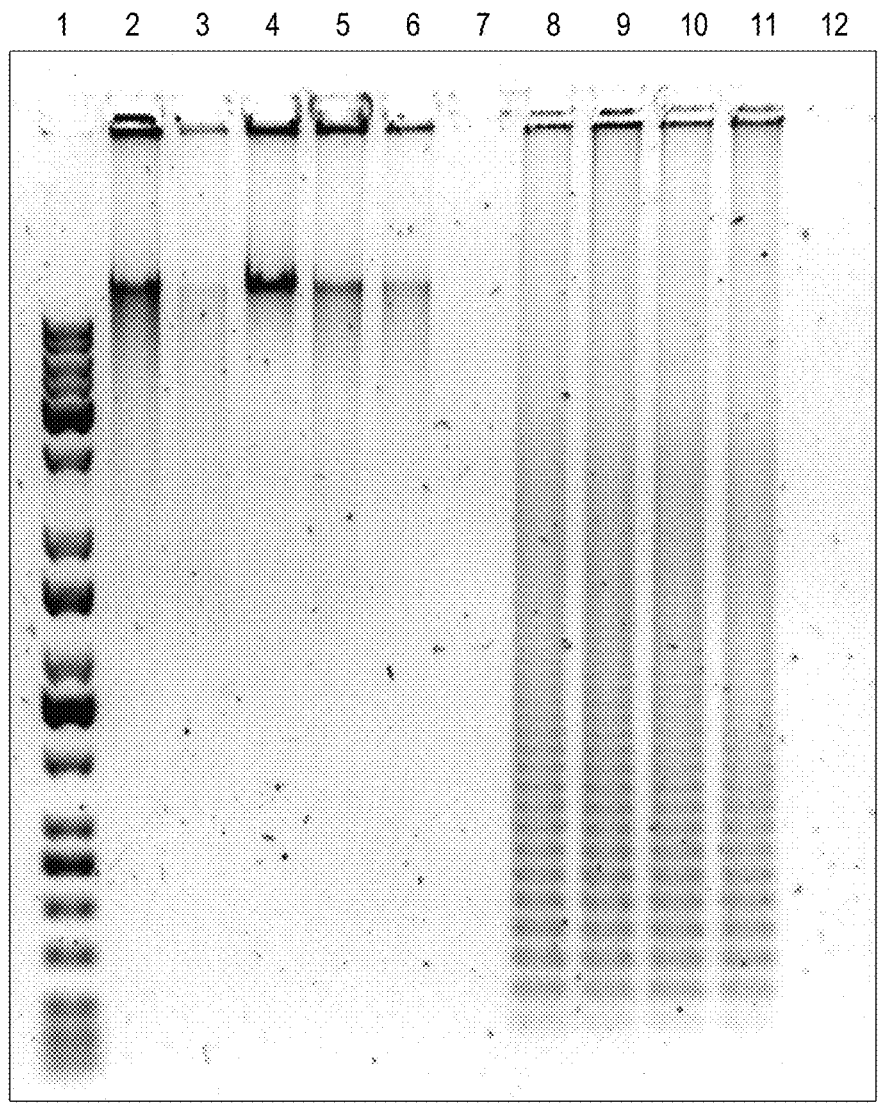
FIG. 10 shows exemplary results of high-molecular weight tag production with two distinct polymerases. Lane 1: KAPA Universal ladder (Kapa Biosystems, Inc.). Lanes 2-3: HMW DNA Tag 1 and Lanes 4-6: HMW DNA Tags 5, 13 and 14, respectively, produced with (p29 DNA polymerase. Lane 7: (p29 DNA polymerase NTC reaction. Lanes 8-11: Tags 1, 5, 13 and 14, respectively, produced with Bst large fragment DNA polymerase. Lane 12: Bst DNA polymerase NTC reaction.
Figure 11:
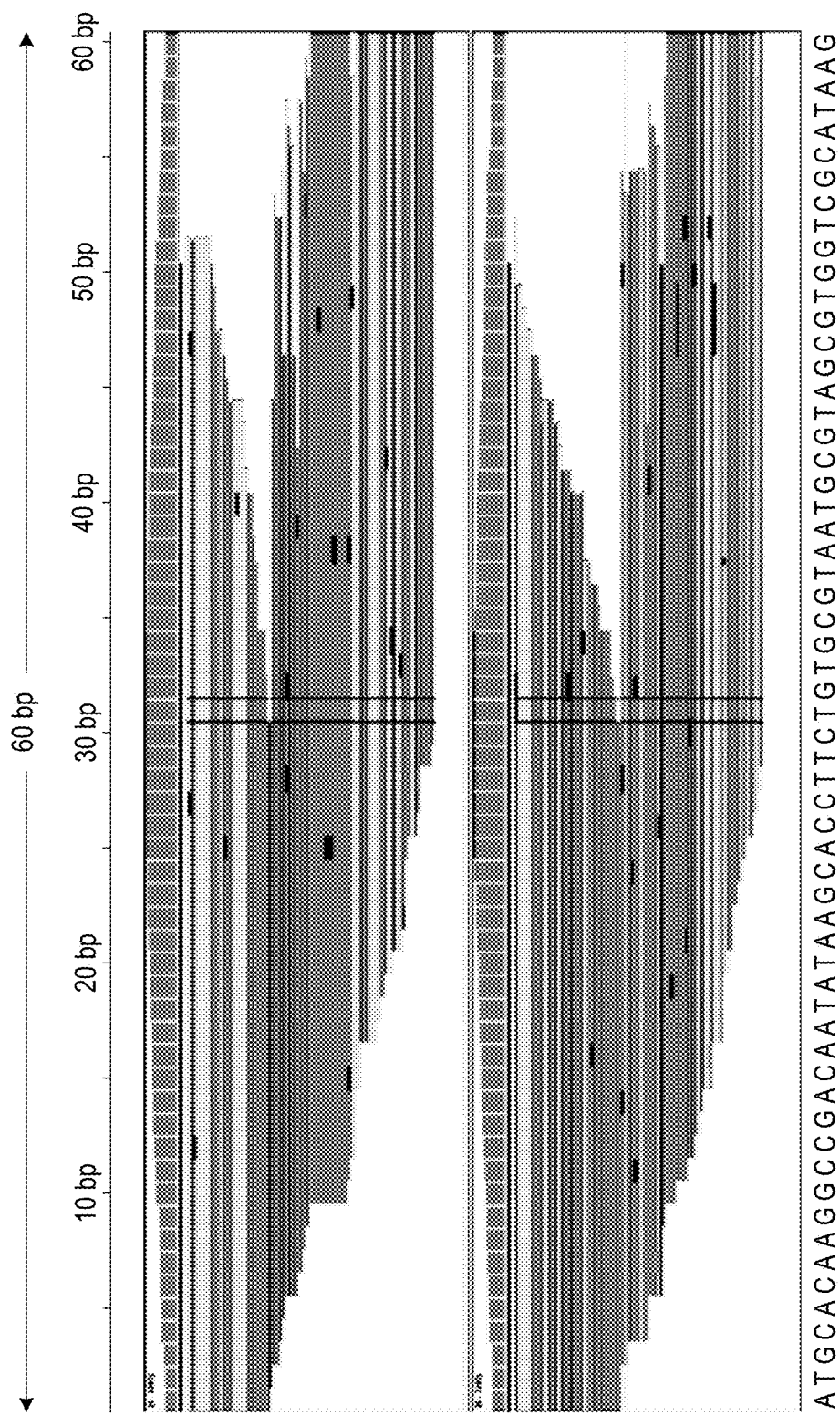
FIG. 11 shows alignment of sequencing reads mapped to an exemplary high-molecular weight tag. Top panel: Tag 4 HMW DNA produced with φ29. Bottom panel: Tag 4 HMW DNA produced with Bst DNA polymerase. At bottom: Tag 4 HMW DNA sequence (SEQ ID NO: 12).

HMW DNA tags produced with φ29 and Bst large fragment (LF) DNA polymerases were analyzed using gel electrophoresis (FIG. 10). In general, HMW tags produced with φ29 and Bst LF DNA polymerase were pure (Table 4) and deep sequencing of HMW DNA Tags 1, 2, 4, 5, 7, 11, and 13 indicated a very good concordance to the predicted sequences (FIG. 11).

Tag purity was measured by sequencing a subset of φ29 or Bst DNA polymerase-produced tags and mapping the resulting Illumina short reads to the tag reference sequences. Extremely low levels of cross contamination were evident (<0.1%), which was attributed to indexing barcode crosstalk (Table 4).

TABLE 4

Number of reads aligned to reference sequences of tags 1-13.
Reads aligned to the tag spiked into each sample are underlined. Sample nomenclature indicates the sequence sample number, the tag spiked into the sample and the polymerase used to derive the HMW tag, e.g., S39_11_bst indicates sequence sample 39, tag 11, and Bst polymerase.

| Sample | Tag Number | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| S34_1_bst | <u>2091</u> | 2 | 0 | 1 | 5 | 0 | 3 | 0 | 0 | 0 | 0 | 0 | 0 |
| S35_2_bst | 5 | <u>1691</u> | 0 | 2 | 0 | 0 | 3 | 0 | 0 | 0 | 4 | 0 | 0 |
| S36_4_bst | 3 | 6 | 0 | <u>2481</u> | 0 | 0 | 0 | 0 | 0 | 0 | 5 | 0 | 5 |
| S37_5_bst | 0 | 0 | 0 | 3 | <u>1655</u> | 0 | 1 | 0 | 0 | 0 | 0 | 0 | 3 |
| S38_7_bst | 2 | 0 | 0 | 0 | 4 | 0 | <u>1773</u> | 0 | 0 | 0 | 1 | 0 | 1 |
| S39_11_bst | 2 | 2 | 0 | 0 | 0 | 0 | 3 | 0 | 0 | 0 | <u>1640</u> | 0 | 5 |
| S40_13_bst | 0 | 1 | 0 | 1 | 2 | 0 | 2 | 0 | 0 | 0 | 3 | 0 | <u>1754</u> |
| S27_1_phi | <u>1379</u> | 3 | 0 | 0 | 0 | 0 | 4 | 0 | 0 | 0 | 1 | 0 | 0 |
| S28_2_phi | 2 | <u>1366</u> | 0 | 2 | 0 | 0 | 0 | 0 | 0 | 0 | 5 | 0 | 2 |
| S29_4_phi | 2 | 0 | 0 | <u>2056</u> | 6 | 0 | 0 | 0 | 0 | 0 | 0 | 0 | 5 |
| S30_5_phi | 3 | 0 | 0 | 3 | <u>1580</u> | 0 | 7 | 0 | 0 | 0 | 0 | 0 | 0 |
| S31_7_phi | 2 | 3 | 0 | 2 | 4 | 0 | <u>1257</u> | 0 | 0 | 0 | 3 | 0 | 0 |
| S32_11_phi | 0 | 2 | 0 | 6 | 1 | 0 | 2 | 0 | 0 | 0 | <u>1397</u> | 0 | 3 |
| S33_13_phi | 3 | 1 | 0 | 8 | 10 | 0 | 0 | 0 | 0 | 0 | 0 | 0 | <u>1254</u> |

Example 5

Manufacture of 96 Tags to Demonstrate Ability to Scale Up Use of Tags

An additional 80 ssDNA oligos were designed, which have an edit distance of >8 in the variable region.

HMW DNA tags were synthesized from ssDNA oligos using Bst DNA polymerase according to the protocol described in Example 1. A total of 96 ssDNA oligos were used, which included Tags 1-16 (SEQ ID NOs:1, 5, and 11-24) and the additional set of 80 oligos (SEQ ID NOs: 28-107) as shown in Table 5.

TABLE 5

| Tag No. | Tag Sequence |
|---|---|
| 17 | ATGCACAAGGCCGACAATAATCGCACTGTAGTGGTAGTGCGTAGCGTGGTCGCATAAG (SEQ ID NO: 28) |
| 18 | ATGCACAAGGCCGACAATAATCATGCGAGGCTCTCTCTACGTAGCGTGGTCGCATAAG (SEQ ID NO: 29) |
| 19 | ATGCACAAGGCCGACAATACCATAGTCCGGTCTCTGTATCGTAGCGTGGTCGCATAAG (SEQ ID NO: 30) |
| 20 | ATGCACAAGGCCGACAATATCGCATCAAGAGGCTCCAATCGTAGCGTGGTCGCATAAG (SEQ ID NO: 31) |
| 21 | ATGCACAAGGCCGACAATAGAGATATCAACTTCGCGAGCCGTAGCGTGGTCGCATAAG (SEQ ID NO: 32) |
| 22 | ATGCACAAGGCCGACAATACGCGAATTAGAACTAGTCCGCGTAGCGTGGTCGCATAAG (SEQ ID NO: 33) |
| 23 | ATGCACAAGGCCGACAATAAGTAGGACCTGCGTTAAGCTCGTAGCGTGGTCGCATAAG (SEQ ID NO: 34) |
| 24 | ATGCACAAGGCCGACAATACTCGCCAGTATACAACTGCTCGTAGCGTGGTCGCATAAG (SEQ ID NO: 35) |
| 25 | ATGCACAAGGCCGACAATAACTCGTCCTCTAGATGCAGACGTAGCGTGGTCGCATAAG (SEQ ID NO: 36) |
| 26 | ATGCACAAGGCCGACAATAGAGAAGTACGGCGCGAATTACGTAGCGTGGTCGCATAAG (SEQ ID NO: 37) |
| 27 | ATGCACAAGGCCGACAATAGCTGCTATGCACTATCTCTCCGTAGCGTGGTCGCATAAG (SEQ ID NO: 38) |
| 28 | ATGCACAAGGCCGACAATAATGTCGCACTACAGGTTGCACGTAGCGTGGTCGCATAAG (SEQ ID NO: 39) |
| 29 | ATGCACAAGGCCGACAATATATCCACCTATCCACATGGCCCGTAGCGTGGTCGCATAAG (SEQ ID NO: 40) |
| 30 | ATGCACAAGGCCGACAATATCACCTGTACTGTGGTGGTTCGTAGCGTGGTCGCATAAG (SEQ ID NO: 41) |
| 31 | ATGCACAAGGCCGACAATAGATCGCATATAGTGCACCTGCGTAGCGTGGTCGCATAAG (SEQ ID NO: 42) |
| 32 | ATGCACAAGGCCGACAATACTTAACGGTTGCACGGATTCCGTAGCGTGGTCGCATAAG (SEQ ID NO: 43) |
| 33 | ATGCACAAGGCCGACAATACACAGGCTGTCTAATCTACGCGTAGCGTGGTCGCATAAG (SEQ ID NO: 44) |
| 34 | ATGCACAAGGCCGACAATACCTATAGCGCAATTGTGTCCCGTAGCGTGGTCGCATAAG (SEQ ID NO: 45) |
| 35 | ATGCACAAGGCCGACAATACCTGTAGCATGCAATGACGTCGTAGCGTGGTCGCATAAG (SEQ ID NO: 46) |
| 36 | ATGCACAAGGCCGACAATAGCGTGTGATTAACCTTGCAGCGTAGCGTGGTCGCATAAG (SEQ ID NO: 47) |
| 37 | ATGCACAAGGCCGACAATATAGTTCATAGGTCCGTGACGCGTAGCGTGGTCGCATAAG (SEQ ID NO: 48) |
| 38 | ATGCACAAGGCCGACAATAGGTCTATTCGGAGCACGTTACGTAGCGTGGTCGCATAAG (SEQ ID NO: 49) |
| 39 | ATGCACAAGGCCGACAATACTTAGGCTAGGAGGCTTGTACGTAGCGTGGTCGCATAAG (SEQ ID NO: 50) |
| 40 | ATGCACAAGGCCGACAATACTAACGTGGTTAGTGAGCACCGTAGCGTGGTCGCATAAG (SEQ ID NO: 51) |
| 41 | ATGCACAAGGCCGACAATAGGTCTAAGAAGTCATCTGCGCGTAGCGTGGTCGCATAAG (SEQ ID NO: 52) |
| 42 | ATGCACAAGGCCGACAATACCAATGTAGCCGCTATTAGGCGTAGCGTGGTCGCATAAG (SEQ ID NO: 53) |

TABLE 5-continued

| Tag No. | Tag Sequence |
|---|---|
| 43 | ATGCACAAGGCCGACAATACTGTGTATTACGGAGCCAAGCGTAGC GTGGTCGCATAAG (SEQ ID NO: 54) |
| 44 | ATGCACAAGGCCGACAATAACCGGTGGTGATCAGTTAAGCGTAGC GTGGTCGCATAAG (SEQ ID NO: 55) |
| 45 | ATGCACAAGGCCGACAATATTCACGGTATGCACACCTTGCGTAGC GTGGTCGCATAAG (SEQ ID NO: 56) |
| 46 | ATGCACAAGGCCGACAATACGTATGACCTCACACTCTCACGTAGC GTGGTCGCATAAG (SEQ ID NO: 57) |
| 47 | ATGCACAAGGCCGACAATAAACTGGCGCCGAACATCTAACGTAGC GTGGTCGCATAAG (SEQ ID NO: 58) |
| 48 | ATGCACAAGGCCGACAATAGATCGGTCGCACTAATGAACCGTAGC GTGGTCGCATAAG (SEQ ID NO: 59) |
| 49 | ATGCACAAGGCCGACAATAGTCTGAACACGTGAATCGGACGTAGC GTGGTCGCATAAG (SEQ ID NO: 60) |
| 50 | ATGCACAAGGCCGACAATATTCCTCGATGCTATCGCACACGTAGC GTGGTCGCATAAG (SEQ ID NO: 61) |
| 51 | ATGCACAAGGCCGACAATAAGATTACGAACCGTAGGACCCGTAGC GTGGTCGCATAAG (SEQ ID NO: 62) |
| 52 | ATGCACAAGGCCGACAATACATGTTCGTATTGGTGCCTGCGTAGC GTGGTCGCATAAG (SEQ ID NO: 63) |
| 53 | ATGCACAAGGCCGACAATAGCCTGTGTTCCATCAGCTTACGTAGC GTGGTCGCATAAG (SEQ ID NO: 64) |
| 54 | ATGCACAAGGCCGACAATAAAGGTCGTGAGTACTCCTTCCGTAGC GTGGTCGCATAAG (SEQ ID NO: 65) |
| 55 | ATGCACAAGGCCGACAATAAGTGTATTGGCGAACCGACTCGTAGC GTGGTCGCATAAG (SEQ ID NO: 66) |
| 56 | ATGCACAAGGCCGACAATAGCCTGATGTATATTGCGCACGTAGC GTGGTCGCATAAG (SEQ ID NO: 67) |
| 57 | ATGCACAAGGCCGACAATACGCTAGAATGAGGTAGGCAACGTAGC GTGGTCGCATAAG (SEQ ID NO: 68) |
| 58 | ATGCACAAGGCCGACAATACATACGCCTTAGTCGGAACACGTAGC GTGGTCGCATAAG (SEQ ID NO: 69) |
| 59 | ATGCACAAGGCCGACAATATTGCTTACGATCTGCGTAGGCGTAGC GTGGTCGCATAAG (SEQ ID NO: 70) |
| 60 | ATGCACAAGGCCGACAATATGCGTTATTGCAGTATCGCCCGTAGC GTGGTCGCATAAG (SEQ ID NO: 71) |
| 61 | ATGCACAAGGCCGACAATACTAGACGCCTGAAGAATGGACGTAGC GTGGTCGCATAAG (SEQ ID NO: 72) |
| 62 | ATGCACAAGGCCGACAATAGAGAAGGAACGAGTGTTACCCGTAGC GTGGTCGCATAAG (SEQ ID NO: 73) |
| 63 | ATGCACAAGGCCGACAATAATTCAACCGACTCGAACTGCCGTAGC GTGGTCGCATAAG (SEQ ID NO: 74) |
| 64 | ATGCACAAGGCCGACAATAGTACTCCTAGATATGACGGCCGTAGC GTGGTCGCATAAG (SEQ ID NO: 75) |
| 65 | ATGCACAAGGCCGACAATACGCGGACATAGTTAAGCGTACGTAGC GTGGTCGCATAAG (SEQ ID NO: 76) |
| 66 | ATGCACAAGGCCGACAATATTCGTACGAGACGTGCTGATCGTAGC GTGGTCGCATAAG (SEQ ID NO: 77) |
| 67 | ATGCACAAGGCCGACAATAACACATAACGCCGCAATCTCCGTAGC GTGGTCGCATAAG (SEQ ID NO: 78) |
| 68 | ATGCACAAGGCCGACAATATAGACCAGCCTACTATTCGCCGTAGC GTGGTCGCATAAG (SEQ ID NO: 79) |
| 69 | ATGCACAAGGCCGACAATAGACACAGTGTCTCTAATGCCCGTAGC GTGGTCGCATAAG (SEQ ID NO: 80) |
| 70 | ATGCACAAGGCCGACAATAATGGCTCGCAGGAGATGTATCGTAGC GTGGTCGCATAAG (SEQ ID NO: 81) |
| 71 | ATGCACAAGGCCGACAATAGCTTACGGTGTGATAGTACGCGTAGC GTGGTCGCATAAG (SEQ ID NO: 82) |
| 72 | ATGCACAAGGCCGACAATATGTACTACGGCTGATTCCTCCGTAGC GTGGTCGCATAAG (SEQ ID NO: 83) |
| 73 | ATGCACAAGGCCGACAATATCGTTCTGTACTGGTTGCTCCGTAGC GTGGTCGCATAAG (SEQ ID NO: 84) |
| 74 | ATGCACAAGGCCGACAATATGAGACGGTATGTCGCAGATCGTAGC GTGGTCGCATAAG (SEQ ID NO: 85) |
| 75 | ATGCACAAGGCCGACAATAACCTTGCAATCCGTCACAAGCGTAGC GTGGTCGCATAAG (SEQ ID NO: 86) |
| 76 | ATGCACAAGGCCGACAATAACCAAGAGTCTTGTCCAGAGCGTAGC GTGGTCGCATAAG (SEQ ID NO: 87) |
| 77 | ATGCACAAGGCCGACAATAGGTAAGCTGACATTCGACACCGTAGC GTGGTCGCATAAG (SEQ ID NO: 88) |
| 78 | ATGCACAAGGCCGACAATACAATTGAGGTGTGCAATGGCCGTAGC GTGGTCGCATAAG (SEQ ID NO: 89) |
| 79 | ATGCACAAGGCCGACAATAGGCTGTTCGTGATAGGATCACGTAGC GTGGTCGCATAAG (SEQ ID NO: 90) |
| 80 | ATGCACAAGGCCGACAATAAGGCGGTGCGTAATAGTGTTCGTAGC GTGGTCGCATAAG (SEQ ID NO: 91) |
| 81 | ATGCACAAGGCCGACAATAGATACGAAGTTACAGCCTGCCGTAGC GTGGTCGCATAAG (SEQ ID NO: 92) |
| 82 | ATGCACAAGGCCGACAATACTAATGCATACTGCTGGAGGCGTAGC GTGGTCGCATAAG (SEQ ID NO: 93) |
| 83 | ATGCACAAGGCCGACAATAGCTTCGGTTAGACTAGAGAGCGTAGC GTGGTCGCATAAG (SEQ ID NO: 94) |
| 84 | ATGCACAAGGCCGACAATACCGGTTGATATTCTAGGCCACGTAGC GTGGTCGCATAAG (SEQ ID NO: 95) |
| 85 | ATGCACAAGGCCGACAATACATGAGGAGAGGTATTCCTCCGTAGC GTGGTCGCATAAG (SEQ ID NO: 96) |
| 86 | ATGCACAAGGCCGACAATAGAATCGTCTACCTAGCTCGTCGTAGC GTGGTCGCATAAG (SEQ ID NO: 97) |
| 87 | ATGCACAAGGCCGACAATAGGTGAAGTTAGACCTGGACTCGTAGC GTGGTCGCATAAG (SEQ ID NO: 98) |
| 88 | ATGCACAAGGCCGACAATAGGATTGTAGGATGACTCCTGCGTAGC GTGGTCGCATAAG (SEQ ID NO: 99) |
| 89 | ATGCACAAGGCCGACAATAAGATTGCGCCGGTACAATTGCGTAGC GTGGTCGCATAAG (SEQ ID NO: 100) |
| 90 | ATGCACAAGGCCGACAATAGTTCCGCCGAGTATTCATAGCGTAGC GTGGTCGCATAAG (SEQ ID NO: 101) |
| 91 | ATGCACAAGGCCGACAATACTTGTACAGCAGTCTAAGCCCGTAGC GTGGTCGCATAAG (SEQ ID NO: 102) |
| 92 | ATGCACAAGGCCGACAATAGAAGCGCGCATGAATTGATCCGTAGC GTGGTCGCATAAG (SEQ ID NO: 103) |
| 93 | ATGCACAAGGCCGACAATATACCGGAATCGTGTCTGTCTCGTAGC GTGGTCGCATAAG (SEQ ID NO: 104) |

TABLE 5-continued

| Tag No. | Tag Sequence |
|---|---|
| 94 | ATGCACAAGGCCGACAATAGCTTCATGGCAATGCATCGTCGTAGC GTGGTCGCATAAG (SEQ ID NO: 105) |
| 95 | ATGCACAAGGCCGACAATAGACCTGCGTACCTTGTCTTACGTAGC GTGGTCGCATAAG (SEQ ID NO: 106) |
| 96 | ATGCACAAGGCCGACAATAGCCGCAGATTACAAGGATTGCGTAGC GTGGTCGCATAAG (SEQ ID NO: 107) |

With reference to Table 5, each of the oligos adhered to the [A-B—C] monomer sequence format (B regions are underlined) as described herein.

Illumina-compatible libraries were created from each tag using the KAPA Hyper Plus library preparation kit (30 minute shearing of DNA followed by A-tailing and adapter ligation as per the manufacturer's instructions).

The 96 libraries were pooled and sequenced on an Illumina MiSeq Platform.

Trimmed Illumina sequences were aligned to a concatemer of the tag sequences to determine the percentage of reads that aligned to the tags. The concatemer comprised the structure $X_{20}$-[A-B—C]$_3$—$Y_{20}$, where $X_{20}$ and $Y_{20}$ each represent a sequence of 20 consecutive degenerate bases (i.e., a combination of any of the four nucleic acids).

Figure 12A:
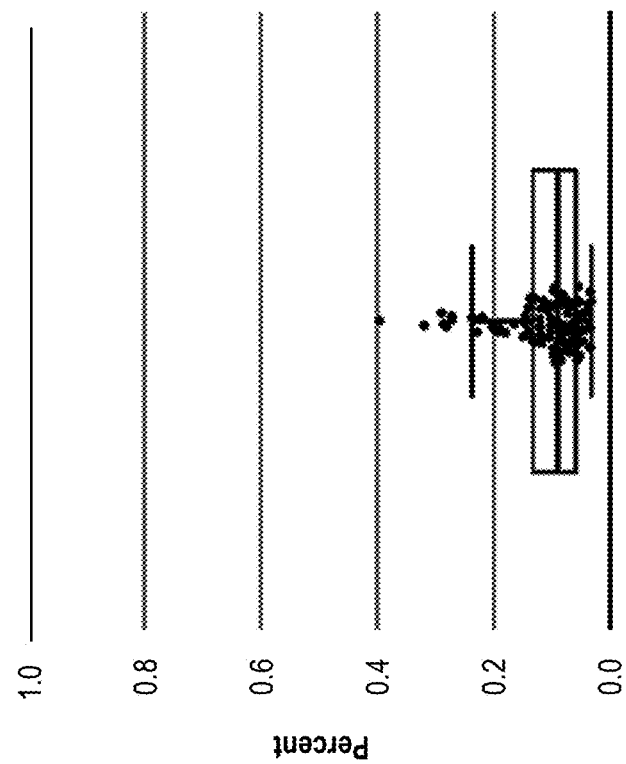
FIG. 12A is a scatter plot showing the percentage of reads aligned to correct tag reference sequences (median 99.9%) for a set of 96 different HMW DNA tags prepared according to the present disclosure. Each dot in the plot represents a single tag.
Figure 12B:
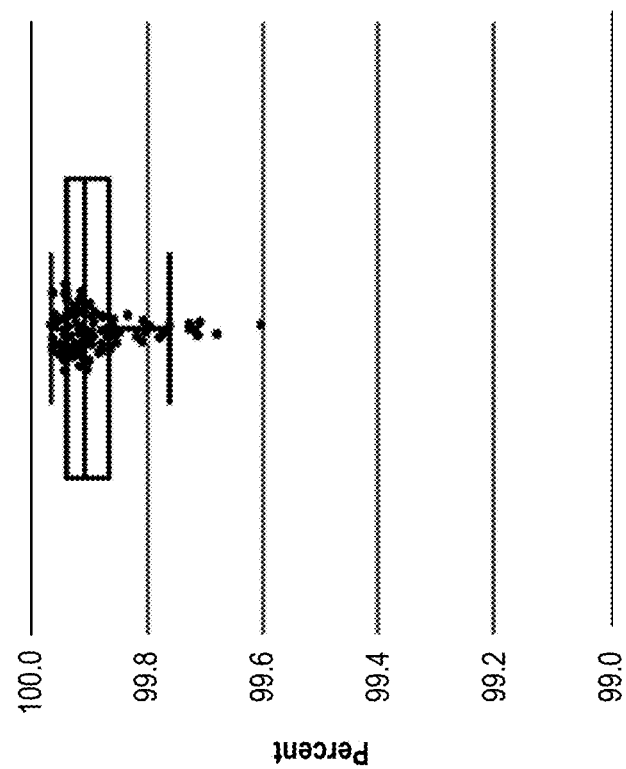
FIG. 12B is a scatter plot showing the percentage of reads aligned to incorrect tag reference sequences (median 0.06%) for the set of 96 different HMW DNA tags of FIG. 12A. Each dot in the plot represents a single tag.

Referring to FIG. 12, the true positive and false negative distribution was determined based on the percentage of total tag reads that aligned to the correct tag reference sequences (true positive) and incorrect tag reference sequences (false negative).

Following de-multiplexing, at least 40,000 reads were obtained for each of library 1 though library 96.

More than 99% (median 99.9%) of reads aligned to the correct tag with a similar distribution across all tag sequences, thereby demonstrating the feasibility of increasing the number of tags used without cross-contamination. Moreover, the false negative rate of less than 0.5% (median 0.06%) indicated that there was sufficient variability between the set of 96 tags to allow for clear identification with minimal cross-talk.

Example 6

Incorporation of Methylated Nucleotides into the Tag Sequence

In one aspect, methylated nucleotides can be incorporated into a tag sequence, which is useful for various applications. One application of a tag having one or more methylated nucleotides includes spike-in controls for bisulfite sequencing experiments, methylated DNA immunoprecipitation (MeDIP) experiments, or a combination thereof. In general, MeDIP is a purification technique in which a sample is enriched for methylated DNA sequences. Therefore, tags having one or more methylated nucleotides can be added to a sample prior to enrichment in order to provide for enrichment of the methylated tags alongside any methylated sequences in the sample.

Tags having one or more methylated nucleotides can additionally (or alternatively) be useful for bisulfite sequencing experiments. In one example, the ratio of methylated nucleotides to non-methylated nucleotides in the tags (i.e., the methylation ratio) can be varied in order to track the degree of bisulfite conversion. Moreover, the methylation ratio can be varied in order to identify the amount of bisulfite conversion required to detect different levels of methylation. In another example, a combination of different tags can be provided where each of the different tags has a distinct methylation ratio or a number of methylated nucleotides. In one embodiment, a combination of different tags can include a first tag having at least one methylated dCTP and a second tag having only non-methylated dCTP (i.e., the second tag includes no methylated dCTP). In another embodiment, a combination of different tags can include a first tag having at least one more methylated dCTP as compared with a second tag. In yet another embodiment, a combination of different tags can include a first tag having an equal number of methylated dCTP as compared with a second tag, where the first tag has a different methylation pattern than the second tag. In the case that the first tag and the second tag have the same nucleic acid sequences (but different methylation patterns) the combination of the two tags can simulate different levels of methylation at a single locus. The methylated tags could be produced as described herein by including 5-methyl-dCTP instead of (or in addition) to dCTP during the polymerization step with a strand displacing DNA polymerase.

Example 7

Tags Having One or More Biotinylated dNTP's

In another embodiment, one or more biotinylated dNTPs can be incorporated into a tag (e.g., during the step of polymerization) as described here. For example, biotin-16-dUTP can be incorporated into the tag sequence by using primers which contain biotinylated bases, by including a percentage of biotinylated nucleotides during the synthesis of the tags, the like, and combinations thereof. Biotinylated tags can be useful in workflows that involve biotin-streptavidin based capture such as in-solution hybrid capture (see, for example, U.S. Patent Application Publication No. 2012/0046175 to Rodesch et al.). In another aspect, addition of biotinylated bases to tags can be generally useful for tag purification or manipulation. In addition (or as an alternative) to biotinylation, a tag can be provided with another like binding moiety, such as digoxigenin, or another suitable binding moiety.

Example 8

Tags Including an RNA Polymerase Promoter Sequence

In one embodiment, a tag can designed to include an RNA polymerase promoter sequence within at least one of the conserved regions of the tag. The RNA polymerase promoter sequence can be selected from a eukaryotic promoter sequence, a prokaryotic promoter sequence, an archaeal promoter sequence, a synthetic promoter sequence, another like promoter sequence, or a combination thereof. The inclusion of a promoter sequence can enable synthesis of RNA-based tags with RNA polymerase to produce run-off transcripts using the DNA-based tags as a template. One example of a tag having an RNA polymerase promoter sequence includes a tag with the following generic structure:

5'-[RNA-polymerase-promoter]-[variable region]-[constant region]-3'

As shown above, the tag includes in the 5' to 3' direction: i) a first region including an RNA polymerase promoter sequence, ii) a second region having a variable sequence, and iii) a third region having a constant or defined sequence.

A specific example of a nucleotide sequence for use in preparing a tag includes the T7 RNA polymerase promoter TAATACGACTCACTATAG (SEQ ID NO:25), the variable sequence GGCACGAGCATAGAAGTTAGTA (SEQ ID NO:3), and the constant sequence GTAGCGTGGTCG-CATAA (SEQ ID NO:26) as follows:
TAATACGACTCACTATAGGGCACGAGCATAGAAGT-TAGTACGTAGCGTGGTCGCATAAG (SEQ ID NO:27)

The nucleotide sequence (SEQ ID NO:27) would be annealed and ligated as described in the preceding examples to provide a ligated circular template for the production of long double stranded DNA (dsDNA), using strand displacing polymerases as described herein. The high-molecular weight dsDNA product can be a substrate for T7 RNA polymerase, thereby resulting in transcription of the tag DNA to a corresponding RNA. The RNA transcript of the tag would contain the repeating structure of the tag and would produce a generally continuous distribution of RNA products of varying lengths due to variable random termination inherent in the transcription of the tag template.

In one example approach for the synthesis of RNA transcripts of tags, 1 µg of the high-molecular weight dsDNA as produced in Example 1 can be used as template in a reaction containing 100 units of T7 RNA polymerase, 1× T7 RNA polymerase reaction buffer (New England Biolabs), 0.5 mM each of ATP, CTP, GTP, and TTP, 1 unit RNase inhibitor, and 5 mM DTT. The reaction can be incubated at 37° C. for 2 hours after which the resulting RNA transcripts can be purified by first digesting the template DNA with DNase I followed by ethanol precipitation of the RNA transcripts. Following quantification, the RNA transcripts of the tag can be added to a sample including mRNA or total RNA prior to library preparation for RNA-seq.

Example 9

Inclusion of Tags in Sample Collection Vessels

In one aspect, tags according to the present disclosure can be provided separately or as a component of a sample collection system. In the case that the tags are included as a component of a sample collection system, instead of supplying the tags as a separate component for addition to a nucleic acid sample prior to library preparation or for addition to a crude tissue sample prior to nucleic acid extraction, the tags can be provided in a vessel such as a sample collection tube or vial. In one example, tags can be included in a collection vial, such as a saliva collection vial, a blood collection vial, or the like. The collection vial can be provided as a uniquely labeled (e.g., barcoded) sample collection tube that already includes a composition disposed therein, where the composition comprises a specific tag that is unique or specific to the label on the collection vial. In the case that a sample (e.g., blood, tissue, saliva, or the like) is added to the collection vial including the tag, the sample, and therefore any nucleic acid material contained therein, can be mixed indelibly at the point of collection. Inclusion of the tags at point of collection can decrease the potential for cross-contamination or incorrect tag assignment during the extraction, library prep, and sequencing workflow. In still another example, the tag is provided in combination with the collection implement by adsorbing the tag onto a solid collection surface such as a blood spot (Guthrie) card, a cheek swab implement, or the like.

Equivalents

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A composition comprising a sample for sequencing and a synthetic nucleic acid tag whose nucleic acid sequence comprises a plurality of repeating units of a structure A-B—C, the synthetic nucleic acid tag having an overall structure represented by the formula:

$$X_i\text{-}[A\text{-}B\text{—}C]_n\text{—}Y_j,$$

wherein the synthetic nucleic acid tag includes n repeats of the structure A-B—C, wherein n is at least two, wherein each of an element A, an element B, and an element C comprises a nucleic acid sequence comprising a defined length of at least two nucleotides, wherein the synthetic nucleic acid tag includes i repeats of X, wherein the synthetic nucleic acid tag includes j repeats of Y, wherein X comprises at least one of a sequence of the element C, a distinct nucleic acid sequence, and a sequence comprising a nucleic acid modification, wherein Y comprises at least one of a sequence of the element A, a distinct nucleic acid sequence, and a sequence comprising nucleic acid modification, wherein the element B comprises a sequence comprising less than 10% identity to any sequence in the sample, as determined by reference to a sequence analysis program, wherein the sequence analysis program is BLASTN, and wherein i and j are integers independent selected from 1-100.

2. A set of samples for sequence analysis, wherein each sample contains at least one synthetic nucleic acid tag whose nucleotide sequence comprises a plurality of repeating units according to the formula $X_i\text{-}[A\text{-}B\text{—}C]_n\text{—}Y_j,$ wherein an element A and an element C each comprise a sequence of at least 8 nucleotides in length, and wherein the element A and the element C are one of the same length and different lengths, wherein an element B comprises a nucleic acid sequence of at least 8 nucleotides, and wherein the synthetic nucleic acid tag includes i repeats of X, wherein the synthetic nucleic acid tag includes j repeats of Y, wherein X comprises at least one of a sequence of the element C, a distinct nucleic acid sequence, and a sequence comprising a nucleic acid modification, wherein Y comprises at least one of a sequence of the element A, a distinct nucleic acid sequence, and a sequence comprising a nucleic acid modification, wherein, for each sample in the set of samples, the element B comprises a sequence comprising less than 10% identity to any sequence in the sample, as determined by reference to a sequence analysis program, wherein the sequence analysis program is BLASTN, and wherein i and j are integers independently selected from 1-100.

3. The composition of claim 1, wherein:

each of the element A and the element C comprises at least one primer landing pad sequence element in that a primer hybridized thereto can be extended, and further wherein the element A and the element C comprise nucleotide sequences that are compatible with one another in that oppositely directed primers can simultaneously hybridize to both of the element A and the element C so that an amplification product is generated by extension of the hybridized primers.

4. The composition of claim 1, wherein the element B has a length sufficient to ensure that each element B sequence in the tag comprises a different nucleic acid sequence from each other element B sequence in the tag.

5. The composition of claim 1 or the set of samples of claim 2, wherein at least a portion of the tag is double stranded.

6. The composition of claim 1 or the set of samples of claim 2, wherein the tag includes at least one methylated nucleotide.

7. The composition of claim 1 or the set of samples of claim 2, wherein the tag includes at least one binding moiety.

8. The composition of claim 1 or the set of samples of claim 2, wherein the tag includes at least one promoter sequence for an RNA polymerase.

9. The composition of claim 1 or the set of samples of claim 2, wherein the tag is one of disposed in a collection vessel, and adsorbed onto the surface of a collection implement.

10. The set of samples for sequence analysis of claim 2, wherein the sequence of the element B in each tag in the set of samples comprises a sequence that differs from the nucleic acid sequence of the element B in all of the other tags in the set of samples.

11. The set of samples of claim 2, wherein the element B has a sequence distinct from any and all sequences present in the sample.

12. A method of preparing an RNA transcript from the synthetic nucleic acid tag of claim 1, comprising transcribing a synthetic nucleic acid tag having a promoter sequence, the synthetic nucleic acid tag comprising a nucleic acid sequence including a plurality of repeating units of structure A-B—C, the synthetic nucleic acid tag further comprising an overall structure represented by the following formula:

$$X_i\text{-}[A\text{-}B\text{—}C]_n\text{—}Y_j,$$

wherein the synthetic nucleic acid tag includes n repeats of the structure A-B—C, wherein n is at least two, and wherein each of an element A, an element B, and an element C comprises a nucleic acid sequence comprising a defined length of at least 2 nucleotides, wherein the synthetic nucleic acid tag includes i repeats of X, wherein the synthetic nucleic acid tag includes j repeats of Y, wherein X comprises at least one of a sequence of the element C, a distinct nucleic acid sequence, and a sequence comprising a nucleic acid modification, wherein Y comprises at least one of a sequence of the element A, a distinct nucleic acid sequence, and a sequence comprising a nucleic acid modification, wherein the element B comprises a sequence comprising less than 10% identity to any sequence in the sample, as determined by reference to a sequence analysis program, wherein the sequence analysis program is BLASTN, and wherein i and j are integers independent selected from 1-100.

13. The method of claim 12, wherein:
each of the element A and the element C comprises at least one primer landing pad sequence element in that a primer hybridized thereto can be extended, and further:
wherein the element A and the element C have nucleotide sequences that are compatible with one another in that oppositely directed primers can simultaneously hybridize to both of the element A and the element C so that an amplification product is generated by extension of the hybridized primers.

14. The method of claim 12, wherein the element B has a sequence distinct from any and all sequences present in the sample.

15. A set of samples for sequence analysis, wherein each sample contains at least one synthetic nucleic acid tag according to claim 1.

16. The composition of claim 1, wherein the element B has a sequence distinct from any and all sequences present in the sample.

17. A kit comprising a plurality of synthetic nucleic acid tags, each of which has a nucleic acid sequence represented by the formula:

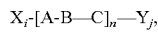

$X_i$-[A-B—C]$_n$—$Y_j$, wherein the synthetic nucleic acid tag includes n repeats of the structure A-B—C, wherein n is at least two, wherein each of an element A, an element B, and an element C comprises a nucleic acid having a defined length of at least 2 nucleotides, wherein the synthetic nucleic acid tag includes i repeats of X, wherein the synthetic nucleic acid tag includes j repeats of Y, wherein X comprises at least one of a sequence of the element C, a distinct nucleic acid sequence, and a sequence comprising a nucleic acid modification, wherein Y comprises at least one of a sequence of the element A, a distinct nucleic acid sequence, and a sequence comprising a nucleic acid modification, wherein the element B comprises a sequence comprising less than 10% identity to any sequence in a sample, as determined by reference to a sequence analysis program, wherein the sequence analysis program is BLASTN, wherein each species of the sequences in the sample is/are known, and wherein the element B comprises a sequence comprising less than 10% identity to any sequence of the species of the sample, as determined by reference to a sequence analysis program, wherein the sequence analysis program is BLASTN, and wherein i and j are integers independently selected from 1-100.

18. The kit of claim 17 wherein:
different tags in the kit are structurally related to one another in that:
the element A of each tag comprises a nucleic acid sequence identical to the nucleic acid sequence of the element A of each tag in the kit;
the element C of each tag comprises a nucleic acid sequence identical to the nucleic acid sequence of the element C of each tag in the kit; and
the element B of each tag comprises a nucleic acid sequence that is not identical to the nucleic acid sequence of the element B of each tag in the kit.

19. The kit of claim 17, further comprising a sample collection tube.

20. The kit of claim 17, wherein at least a portion of the plurality of nucleic acid molecule tags includes at least one methylated nucleotide.

21. The kit of claim 17, wherein at least a portion of the plurality of nucleic acid molecule tags includes at least one binding moiety.

22. The kit of claim 21, wherein the binding moiety is biotin.

23. The kit of claim 17, wherein at least a portion of the plurality of nucleic acid molecule tags includes at least one promoter sequence for an RNA polymerase.

24. The kit of claim 23, wherein the promoter sequence is selected from at least one of a eukaryotic promoter sequence, a prokaryotic promoter sequence, an archaeal promoter sequence or a synthetic promoter sequence.

25. The kit of claim 17, wherein the plurality of nucleic acid molecule tags is one of disposed in a collection vessel, or adsorbed onto the surface of a collection implement.

26. The kit of claim 17, wherein the sequence of each element B in the tag comprises a sequence that differs from the sequence of each other element B within the tag.

27. The kit of claim 17, wherein the sequence of the element B in each tag in the kit comprises a sequence that differs from the nucleic acid sequence of each other element B in the set of tags in the kit.

28. The kit of claim 17, wherein the element B has a sequence distinct from any and all sequences present in the sample.

* * * * *

SEQUENCE LISTING

```
<160> NUMBER OF SEQ ID NOS: 141

<210> SEQ ID NO 1
<211> LENGTH: 60
<212> TYPE: DNA
<213> ORGANISM: Artificial Sequence
<220> FEATURE:
<223> OTHER INFORMATION: synthetic nucleic acid

<400> SEQUENCE: 1
atgcacaagg ccgacaatag gcacgagcat agaagttagt acgtagcgtg gtcgcataag      60

<210> SEQ ID NO 2
<211> LENGTH: 19
<212> TYPE: DNA
<213> ORGANISM: Artificial Sequence
<220> FEATURE:
<223> OTHER INFORMATION: synthetic nucleic acid

<400> SEQUENCE: 2
atgcacaagg ccgacaata                                                  19

<210> SEQ ID NO 3
<211> LENGTH: 22
<212> TYPE: DNA
<213> ORGANISM: Artificial Sequence
```

```
<220> FEATURE:
<223> OTHER INFORMATION: synthetic nucleic acid

<400> SEQUENCE: 3
ggcacgagca tagaagttag ta                                             22

<210> SEQ ID NO 4
<211> LENGTH: 19
<212> TYPE: DNA
<213> ORGANISM: Artificial Sequence
<220> FEATURE:
<223> OTHER INFORMATION: synthetic nucleic acid

<400> SEQUENCE: 4
cgtagcgtgg tcgcataag                                                 19

<210> SEQ ID NO 5
<211> LENGTH: 60
<212> TYPE: DNA
<213> ORGANISM: Artificial Sequence
<220> FEATURE:
<223> OTHER INFORMATION: synthetic nucleic acid

<400> SEQUENCE: 5
atgcacaagg ccgacaatag agtaggacaa tgattgagaa gcgtagcgtg gtcgcataag    60

<210> SEQ ID NO 6
<211> LENGTH: 22
<212> TYPE: DNA
<213> ORGANISM: Artificial Sequence
<220> FEATURE:
<223> OTHER INFORMATION: synthetic nucleic acid

<400> SEQUENCE: 6
gagtaggaca atgattgaga ag                                             22

<210> SEQ ID NO 7
<211> LENGTH: 20
<212> TYPE: DNA
<213> ORGANISM: Artificial Sequence
<220> FEATURE:
<223> OTHER INFORMATION: synthetic nucleic acid

<400> SEQUENCE: 7
ccttgtgcat cttatgcgac                                                20

<210> SEQ ID NO 8
<211> LENGTH: 19
<212> TYPE: DNA
<213> ORGANISM: Artificial Sequence
<220> FEATURE:
<223> OTHER INFORMATION: synthetic nucleic acid

<400> SEQUENCE: 8
atgcacaagg ccgacaata                                                 19

<210> SEQ ID NO 9
<211> LENGTH: 19
<212> TYPE: DNA
<213> ORGANISM: Artificial Sequence
<220> FEATURE:
<223> OTHER INFORMATION: synthetic nucleic acid

<400> SEQUENCE: 9
cttatgcgac cacgctacg                                                 19
```

```
<210> SEQ ID NO 10
<211> LENGTH: 120
<212> TYPE: DNA
<213> ORGANISM: Artificial Sequence
<220> FEATURE:
<223> OTHER INFORMATION: synthetic nucleic acid

<400> SEQUENCE: 10
cttatgcgac cacgctacgt actaacttct atgctcgtgc ctattgtcgg ccttgtgcat      60
cttatgcgac cacgctacgt actaacttct atgctcgtgc ctattgtcgg ccttgtgcat     120

<210> SEQ ID NO 11
<211> LENGTH: 60
<212> TYPE: DNA
<213> ORGANISM: Artificial Sequence
<220> FEATURE:
<223> OTHER INFORMATION: synthetic nucleic acid

<400> SEQUENCE: 11
atgcacaagg ccgacaataa ctttgagcaa acgtcgtctg tcgtagcgtg gtcgcataag      60

<210> SEQ ID NO 12
<211> LENGTH: 60
<212> TYPE: DNA
<213> ORGANISM: Artificial Sequence
<220> FEATURE:
<223> OTHER INFORMATION: synthetic nucleic acid

<400> SEQUENCE: 12
atgcacaagg ccgacaatat aagcaccttc tgtgcgtaat gcgtagcgtg gtcgcataag      60

<210> SEQ ID NO 13
<211> LENGTH: 60
<212> TYPE: DNA
<213> ORGANISM: Artificial Sequence
<220> FEATURE:
<223> OTHER INFORMATION: synthetic nucleic acid

<400> SEQUENCE: 13
atgcacaagg ccgacaatat tacgacgtag ctccgattta gcgtagcgtg gtcgcataag      60

<210> SEQ ID NO 14
<211> LENGTH: 60
<212> TYPE: DNA
<213> ORGANISM: Artificial Sequence
<220> FEATURE:
<223> OTHER INFORMATION: synthetic nucleic acid

<400> SEQUENCE: 14
atgcacaagg ccgacaataa gtgagactga tccttctagc tcgtagcgtg gtcgcataag      60

<210> SEQ ID NO 15
<211> LENGTH: 60
<212> TYPE: DNA
<213> ORGANISM: Artificial Sequence
<220> FEATURE:
<223> OTHER INFORMATION: synthetic nucleic acid

<400> SEQUENCE: 15
atgcacaagg ccgacaatac tctgattcga atgcaagtcg tcgtagcgtg gtcgcataag      60

<210> SEQ ID NO 16
<211> LENGTH: 60
<212> TYPE: DNA
<213> ORGANISM: Artificial Sequence
```

```
<220> FEATURE:
<223> OTHER INFORMATION: synthetic nucleic acid

<400> SEQUENCE: 16
atgcacaagg ccgacaatag gtagcatcaa tttagctcgt ccgtagcgtg gtcgcataag    60

<210> SEQ ID NO 17
<211> LENGTH: 60
<212> TYPE: DNA
<213> ORGANISM: Artificial Sequence
<220> FEATURE:
<223> OTHER INFORMATION: synthetic nucleic acid

<400> SEQUENCE: 17
atgcacaagg ccgacaatac acggctattt cacgttgtag acgtagcgtg gtcgcataag    60

<210> SEQ ID NO 18
<211> LENGTH: 60
<212> TYPE: DNA
<213> ORGANISM: Artificial Sequence
<220> FEATURE:
<223> OTHER INFORMATION: synthetic nucleic acid

<400> SEQUENCE: 18
atgcacaagg ccgacaatag ccggaactct tttaaggcat tcgtagcgtg gtcgcataag    60

<210> SEQ ID NO 19
<211> LENGTH: 60
<212> TYPE: DNA
<213> ORGANISM: Artificial Sequence
<220> FEATURE:
<223> OTHER INFORMATION: synthetic nucleic acid

<400> SEQUENCE: 19
atgcacaagg ccgacaatag cgccaattat gtggactact tcgtagcgtg gtcgcataag    60

<210> SEQ ID NO 20
<211> LENGTH: 60
<212> TYPE: DNA
<213> ORGANISM: Artificial Sequence
<220> FEATURE:
<223> OTHER INFORMATION: synthetic nucleic acid

<400> SEQUENCE: 20
atgcacaagg ccgacaatac gtcacctgta gaaatgtcgt tcgtagcgtg gtcgcataag    60

<210> SEQ ID NO 21
<211> LENGTH: 60
<212> TYPE: DNA
<213> ORGANISM: Artificial Sequence
<220> FEATURE:
<223> OTHER INFORMATION: synthetic nucleic acid

<400> SEQUENCE: 21
atgcacaagg ccgacaatag agcaggtcct atcattatct gcgtagcgtg gtcgcataag    60

<210> SEQ ID NO 22
<211> LENGTH: 60
<212> TYPE: DNA
<213> ORGANISM: Artificial Sequence
<220> FEATURE:
<223> OTHER INFORMATION: synthetic nucleic acid

<400> SEQUENCE: 22
atgcacaagg ccgacaatat cattcatcga ttggcaggta ccgtagcgtg gtcgcataag    60
```

```
<210> SEQ ID NO 23
<211> LENGTH: 60
<212> TYPE: DNA
<213> ORGANISM: Artificial Sequence
<220> FEATURE:
<223> OTHER INFORMATION: synthetic nucleic acid

<400> SEQUENCE: 23
atgcacaagg ccgacaatat cgctgagacg gttctaaatc tcgtagcgtg gtcgcataag      60

<210> SEQ ID NO 24
<211> LENGTH: 60
<212> TYPE: DNA
<213> ORGANISM: Artificial Sequence
<220> FEATURE:
<223> OTHER INFORMATION: synthetic nucleic acid

<400> SEQUENCE: 24
atgcacaagg ccgacaatac attgacgggt tagatatcct ccgtagcgtg gtcgcataag      60

<210> SEQ ID NO 25
<211> LENGTH: 18
<212> TYPE: DNA
<213> ORGANISM: Artificial Sequence
<220> FEATURE:
<223> OTHER INFORMATION: T7 RNA polymerase promoter sequence

<400> SEQUENCE: 25
taatacgact cactatag                                                    18

<210> SEQ ID NO 26
<211> LENGTH: 17
<212> TYPE: DNA
<213> ORGANISM: Artificial Sequence
<220> FEATURE:
<223> OTHER INFORMATION: synthetic nucleic acid

<400> SEQUENCE: 26
gtagcgtggt cgcataa                                                     17

<210> SEQ ID NO 27
<211> LENGTH: 59
<212> TYPE: DNA
<213> ORGANISM: Artificial Sequence
<220> FEATURE:
<223> OTHER INFORMATION: synthetic nucleic acid

<400> SEQUENCE: 27
taatacgact cactataggg cacgagcata gaagttagta cgtagcgtgg tcgcataag       59

<210> SEQ ID NO 28
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 28
atgcacaagg ccgacaataa tcgcactgta gtggtagtgc gtagcgtggt cgcataag        58

<210> SEQ ID NO 29
<211> LENGTH: 58
<212> TYPE: DNA
<213> ORGANISM: Artificial Sequence
<220> FEATURE:
<223> OTHER INFORMATION: synthetic nucleic acid
```

```
<400> SEQUENCE: 29
atgcacaagg ccgacaataa tcatgcgagg ctctctctac gtagcgtggt cgcataag      58

<210> SEQ ID NO 30
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 30
atgcacaagg ccgacaatac catagtccgg tctctgtatc gtagcgtggt cgcataag      58

<210> SEQ ID NO 31
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 31
atgcacaagg ccgacaatat cgcatcaaga ggctccaatc gtagcgtggt cgcataag      58

<210> SEQ ID NO 32
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 32
atgcacaagg ccgacaatag agatatcaac ttcgcgagcc gtagcgtggt cgcataag      58

<210> SEQ ID NO 33
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 33
atgcacaagg ccgacaatac gcgaattaga actagtccgc gtagcgtggt cgcataag      58

<210> SEQ ID NO 34
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 34
atgcacaagg ccgacaataa gtaggacctg cgttaagctc gtagcgtggt cgcataag      58

<210> SEQ ID NO 35
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 35
atgcacaagg ccgacaatac tcgccagtat acaactgctc gtagcgtggt cgcataag      58

<210> SEQ ID NO 36
```

```
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 36
atgcacaagg ccgacaataa ctcgtcctct agatgcagac gtagcgtggt cgcataag        58

<210> SEQ ID NO 37
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 37
atgcacaagg ccgacaatag agaagtacgg cgcgaattac gtagcgtggt cgcataag        58

<210> SEQ ID NO 38
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 38
atgcacaagg ccgacaatag ctgctatgca ctatctctcc gtagcgtggt cgcataag        58

<210> SEQ ID NO 39
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 39
atgcacaagg ccgacaataa tgtcgcacta caggttgcac gtagcgtggt cgcataag        58

<210> SEQ ID NO 40
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 40
atgcacaagg ccgacaatat atcacctatc cacatggccc gtagcgtggt cgcataag        58

<210> SEQ ID NO 41
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 41
atgcacaagg ccgacaatat cacctgtact gtggtggttc gtagcgtggt cgcataag        58

<210> SEQ ID NO 42
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 42
```
atgcacaagg ccgacaatag atcgcatata gtgcacctgc gtagcgtggt cgcataag      58

<210> SEQ ID NO 43
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 43
atgcacaagg ccgacaatac ttaacggttg cacggattcc gtagcgtggt cgcataag      58

<210> SEQ ID NO 44
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 44
atgcacaagg ccgacaatac acaggctgtc taatctacgc gtagcgtggt cgcataag      58

<210> SEQ ID NO 45
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 45
atgcacaagg ccgacaatac ctatagcgca attgtgtccc gtagcgtggt cgcataag      58

<210> SEQ ID NO 46
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 46
atgcacaagg ccgacaatac ctgtagcatg caatgacgtc gtagcgtggt cgcataag      58

<210> SEQ ID NO 47
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 47
atgcacaagg ccgacaatag cgtgtgatta accttgcagc gtagcgtggt cgcataag      58

<210> SEQ ID NO 48
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 48
atgcacaagg ccgacaatat agttcatagg tccgtgacgc gtagcgtggt cgcataag      58

<210> SEQ ID NO 49
<211> LENGTH: 58
<212> TYPE: DNA

<213> ORGANISM: Artificial Sequence
<220> FEATURE:
<223> OTHER INFORMATION: synthetic nucleic acid

<400> SEQUENCE: 49
atgcacaagg ccgacaatag gtctattcgg agcacgttac gtagcgtggt cgcataag    58

<210> SEQ ID NO 50
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 50
atgcacaagg ccgacaatac ttaggctagg aggcttgtac gtagcgtggt cgcataag    58

<210> SEQ ID NO 51
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 51
atgcacaagg ccgacaatac taacgtggtt agtgagcacc gtagcgtggt cgcataag    58

<210> SEQ ID NO 52
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 52
atgcacaagg ccgacaatag gtctaagaag tcatctgcgc gtagcgtggt cgcataag    58

<210> SEQ ID NO 53
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 53
atgcacaagg ccgacaatac caatgtagcc gctattaggc gtagcgtggt cgcataag    58

<210> SEQ ID NO 54
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 54
atgcacaagg ccgacaatac tgtgtattac ggagccaagc gtagcgtggt cgcataag    58

<210> SEQ ID NO 55
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 55
atgcacaagg ccgacaataa ccggtggtga tcagttaagc gtagcgtggt cgcataag    58

<210> SEQ ID NO 56
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 56
atgcacaagg ccgacaatat tcacggtatg cacaccttgc gtagcgtggt cgcataag    58

<210> SEQ ID NO 57
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 57
atgcacaagg ccgacaatac gtatgacctc acactctcac gtagcgtggt cgcataag    58

<210> SEQ ID NO 58
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 58
atgcacaagg ccgacaataa actggcgccg aacatctaac gtagcgtggt cgcataag    58

<210> SEQ ID NO 59
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 59
atgcacaagg ccgacaatag atcggtcgca ctaatgaacc gtagcgtggt cgcataag    58

<210> SEQ ID NO 60
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 60
atgcacaagg ccgacaatag tctgaacacg tgaatcggac gtagcgtggt cgcataag    58

<210> SEQ ID NO 61
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 61
atgcacaagg ccgacaatat tcctcgatgc tatcgcacac gtagcgtggt cgcataag    58

<210> SEQ ID NO 62
<211> LENGTH: 58
<212> TYPE: DNA
<213> ORGANISM: Artificial Sequence
<220> FEATURE:

<223> OTHER INFORMATION: synthetic nucleic acid

<400> SEQUENCE: 62
atgcacaagg ccgacaataa gattacgaac cgtaggaccc gtagcgtggt cgcataag      58

<210> SEQ ID NO 63
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 63
atgcacaagg ccgacaatac atgttcgtat tggtgcctgc gtagcgtggt cgcataag      58

<210> SEQ ID NO 64
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 64
atgcacaagg ccgacaatag cctgtgttcc atcagcttac gtagcgtggt cgcataag      58

<210> SEQ ID NO 65
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 65
atgcacaagg ccgacaataa aggtcgtgag tactccttcc gtagcgtggt cgcataag      58

<210> SEQ ID NO 66
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 66
atgcacaagg ccgacaataa gtgtattggc gaaccgactc gtagcgtggt cgcataag      58

<210> SEQ ID NO 67
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 67
atgcacaagg ccgacaatag cctcgatgta tattgcgcac gtagcgtggt cgcataag      58

<210> SEQ ID NO 68
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 68
atgcacaagg ccgacaatac gctagaatga ggtaggcaac gtagcgtggt cgcataag      58

```
<210> SEQ ID NO 69
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 69
atgcacaagg ccgacaatac atacgcctta gtcggaacac gtagcgtggt cgcataag        58

<210> SEQ ID NO 70
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 70
atgcacaagg ccgacaatat tgcttacgat ctgcgtaggc gtagcgtggt cgcataag        58

<210> SEQ ID NO 71
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 71
atgcacaagg ccgacaatat gcgttattgc agtatcgccc gtagcgtggt cgcataag        58

<210> SEQ ID NO 72
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 72
atgcacaagg ccgacaatac tagacgcctg aagaatggac gtagcgtggt cgcataag        58

<210> SEQ ID NO 73
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 73
atgcacaagg ccgacaatag agaaggaacg agtgttaccc gtagcgtggt cgcataag        58

<210> SEQ ID NO 74
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 74
atgcacaagg ccgacaataa ttcaaccgac tcgaactgcc gtagcgtggt cgcataag        58

<210> SEQ ID NO 75
<211> LENGTH: 58
<212> TYPE: DNA
<213> ORGANISM: Artificial Sequence
<220> FEATURE:
<223> OTHER INFORMATION: synthetic nucleic acid
```

<400> SEQUENCE: 75
atgcacaagg ccgacaatag tactcctaga tatgacggcc gtagcgtggt cgcataag        58

<210> SEQ ID NO 76
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 76
atgcacaagg ccgacaatac gcggacatag ttaagcgtac gtagcgtggt cgcataag        58

<210> SEQ ID NO 77
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 77
atgcacaagg ccgacaatat tcgtacgaga cgtgctgatc gtagcgtggt cgcataag        58

<210> SEQ ID NO 78
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 78
atgcacaagg ccgacaataa cacataacgc cgcaatctcc gtagcgtggt cgcataag        58

<210> SEQ ID NO 79
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 79
atgcacaagg ccgacaatat agaccagcct actattcgcc gtagcgtggt cgcataag        58

<210> SEQ ID NO 80
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 80
atgcacaagg ccgacaatag acacagtgtc tctaatgccc gtagcgtggt cgcataag        58

<210> SEQ ID NO 81
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 81
atgcacaagg ccgacaataa tggctcgcag gagatgtatc gtagcgtggt cgcataag        58

<210> SEQ ID NO 82
<211> LENGTH: 58

```
<212> TYPE: DNA
<213> ORGANISM: Artificial Sequence
<220> FEATURE:
<223> OTHER INFORMATION: synthetic nucleic acid

<400> SEQUENCE: 82
atgcacaagg ccgacaatag cttacggtgt gatagtacgc gtagcgtggt cgcataag      58

<210> SEQ ID NO 83
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 83
atgcacaagg ccgacaatat gtactacggc tgattcctcc gtagcgtggt cgcataag      58

<210> SEQ ID NO 84
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 84
atgcacaagg ccgacaatat cgttctgtac tggttgctcc gtagcgtggt cgcataag      58

<210> SEQ ID NO 85
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 85
atgcacaagg ccgacaatat gagacggtat gtcgcagatc gtagcgtggt cgcataag      58

<210> SEQ ID NO 86
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 86
atgcacaagg ccgacaataa ccttgcaatc cgtcacaagc gtagcgtggt cgcataag      58

<210> SEQ ID NO 87
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 87
atgcacaagg ccgacaataa ccaagagtct tgtccagagc gtagcgtggt cgcataag      58

<210> SEQ ID NO 88
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 88
```
atgcacaagg ccgacaatag gtaagctgac attcgacacc gtagcgtggt cgcataag    58

<210> SEQ ID NO 89
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 89
atgcacaagg ccgacaatac aattgaggtg tgcaatggcc gtagcgtggt cgcataag    58

<210> SEQ ID NO 90
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 90
atgcacaagg ccgacaatag gctgttcgtg ataggatcac gtagcgtggt cgcataag    58

<210> SEQ ID NO 91
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 91
atgcacaagg ccgacaataa ggcggtgcgt aatagtgttc gtagcgtggt cgcataag    58

<210> SEQ ID NO 92
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 92
atgcacaagg ccgacaatag atacgaagtt acagcctgcc gtagcgtggt cgcataag    58

<210> SEQ ID NO 93
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 93
atgcacaagg ccgacaatac taatgcatac tgctggaggc gtagcgtggt cgcataag    58

<210> SEQ ID NO 94
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 94
atgcacaagg ccgacaatag cttcggttag actagagagc gtagcgtggt cgcataag    58

<210> SEQ ID NO 95
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 95
atgcacaagg ccgacaatac cggttgatat tctaggccac gtagcgtggt cgcataag    58

<210> SEQ ID NO 96
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 96
atgcacaagg ccgacaatac atgaggagag gtattcctcc gtagcgtggt cgcataag    58

<210> SEQ ID NO 97
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 97
atgcacaagg ccgacaatag aatcgtctac ctagctcgtc gtagcgtggt cgcataag    58

<210> SEQ ID NO 98
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 98
atgcacaagg ccgacaatag gtgaagttag acctggactc gtagcgtggt cgcataag    58

<210> SEQ ID NO 99
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 99
atgcacaagg ccgacaatag gattgtagga tgactcctgc gtagcgtggt cgcataag    58

<210> SEQ ID NO 100
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 100
atgcacaagg ccgacaataa gattgcgccg gtacaattgc gtagcgtggt cgcataag    58

<210> SEQ ID NO 101
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 101
atgcacaagg ccgacaatag ttccgccgag tattcatagc gtagcgtggt cgcataag    58

<210> SEQ ID NO 102
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 102
atgcacaagg ccgacaatac ttgtacagca gtctaagccc gtagcgtggt cgcataag    58

<210> SEQ ID NO 103
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 103
atgcacaagg ccgacaatag aagcgcgcat gaattgatcc gtagcgtggt cgcataag    58

<210> SEQ ID NO 104
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 104
atgcacaagg ccgacaatat accggaatcg tgtctgtctc gtagcgtggt cgcataag    58

<210> SEQ ID NO 105
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 105
atgcacaagg ccgacaatag cttcatggca atgcatcgtc gtagcgtggt cgcataag    58

<210> SEQ ID NO 106
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 106
atgcacaagg ccgacaatag acctgcgtac cttgtcttac gtagcgtggt cgcataag    58

<210> SEQ ID NO 107
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 107
atgcacaagg ccgacaatag ccgcagatta caaggattgc gtagcgtggt cgcataag    58

<210> SEQ ID NO 108
<211> LENGTH: 22
<212> TYPE: DNA
<213> ORGANISM: Artificial sequence
<220> FEATURE:
<223> OTHER INFORMATION: synethetic nucleic acid

```
<220> FEATURE:
<221> NAME/KEY: misc_feature
<222> LOCATION: (9)..(14)
<223> OTHER INFORMATION: n is a, c, g, or t

<400> SEQUENCE: 108
acgcgacgnn nnnntgggac ga                                              22

<210> SEQ ID NO 109
<211> LENGTH: 51
<212> TYPE: DNA
<213> ORGANISM: Artificial Sequence
<220> FEATURE:
<223> OTHER INFORMATION: aligned read of a synthetic nucleic acid

<400> SEQUENCE: 109
aggccgacaa taggcacgag catagaagtt agtacgtagc gtcgtcgcat a              51

<210> SEQ ID NO 110
<211> LENGTH: 25
<212> TYPE: DNA
<213> ORGANISM: Artificial Sequence
<220> FEATURE:
<223> OTHER INFORMATION: aligned read of a synthetic nucleic acid

<400> SEQUENCE: 110
agttagtacg tagcgtggtc gcata                                           25

<210> SEQ ID NO 111
<211> LENGTH: 42
<212> TYPE: DNA
<213> ORGANISM: Artificial Sequence
<220> FEATURE:
<223> OTHER INFORMATION: aligned read of a synthetic nucleic acid

<400> SEQUENCE: 111
ataggcacga gcatagaagt tagtacgtag cgtcgtcgca ta                        42

<210> SEQ ID NO 112
<211> LENGTH: 45
<212> TYPE: DNA
<213> ORGANISM: Artificial Sequence
<220> FEATURE:
<223> OTHER INFORMATION: aligned read of a synthetic nucleic acid

<400> SEQUENCE: 112
acaataggca cgagcataga agttagtacg tagcgtcgtc acata                     45

<210> SEQ ID NO 113
<211> LENGTH: 60
<212> TYPE: DNA
<213> ORGANISM: Artificial Sequence
<220> FEATURE:
<223> OTHER INFORMATION: aligned read of a synthetic nucleic acid

<400> SEQUENCE: 113
agatgcacaa ggccgacaat aggcacgagc atagaagtta gtacgtagcg tcgtcgcata     60

<210> SEQ ID NO 114
<211> LENGTH: 50
<212> TYPE: DNA
<213> ORGANISM: Artificial Sequence
<220> FEATURE:
<223> OTHER INFORMATION: aligned read of a synthetic nucleic acid

<400> SEQUENCE: 114
```
ggccgacaat aggcacgagc atagaagtta gtacgtagcg tcgtcgcata         50

<210> SEQ ID NO 115
<211> LENGTH: 55
<212> TYPE: DNA
<213> ORGANISM: Artificial Sequence
<220> FEATURE:
<223> OTHER INFORMATION: aligned read of a synthetic nucleic acid

<400> SEQUENCE: 115
cacaaggccg acaataggca cgagcataga agttagtacg tagcgtcgtc gcata    55

<210> SEQ ID NO 116
<211> LENGTH: 60
<212> TYPE: DNA
<213> ORGANISM: Artificial Sequence
<220> FEATURE:
<223> OTHER INFORMATION: aligned read of a synthetic nucleic acid

<400> SEQUENCE: 116
agatgcacaa ggccgacaat aggcacgagc atagatgtta gtccgtttcg tcgccgcata    60

<210> SEQ ID NO 117
<211> LENGTH: 60
<212> TYPE: DNA
<213> ORGANISM: Artificial Sequence
<220> FEATURE:
<223> OTHER INFORMATION: aligned read of a synthetic nucleic acid

<400> SEQUENCE: 117
agatgcacaa ggccgacaat aggcacgagc atagaagtta gtacgtagcg tggtcgcata    60

<210> SEQ ID NO 118
<211> LENGTH: 58
<212> TYPE: DNA
<213> ORGANISM: Artificial Sequence
<220> FEATURE:
<223> OTHER INFORMATION: aligned read of a synthetic nucleic acid

<400> SEQUENCE: 118
atgcacaagg ccgacaatag gcacgagcat agaagttagt acgtagcgtc gtcgcata    58

<210> SEQ ID NO 119
<211> LENGTH: 60
<212> TYPE: DNA
<213> ORGANISM: Artificial Sequence
<220> FEATURE:
<223> OTHER INFORMATION: aligned read of a synthetic nucleic acid

<400> SEQUENCE: 119
agatgcacaa ggccgacaat aggcacgagc atagaaggta gtacgtagcg tcgtcgcata    60

<210> SEQ ID NO 120
<211> LENGTH: 60
<212> TYPE: DNA
<213> ORGANISM: Artificial Sequence
<220> FEATURE:
<223> OTHER INFORMATION: aligned read of a synthetic nucleic acid

<400> SEQUENCE: 120
agatgcacaa ggccgacaat aggcacgagc atagaagtta gtacgtagcg tcgtcgcata    60

<210> SEQ ID NO 121
<211> LENGTH: 60
<212> TYPE: DNA
<213> ORGANISM: Artificial Sequence

```
<220> FEATURE:
<223> OTHER INFORMATION: aligned read of a synthetic nucleic acid

<400> SEQUENCE: 121
agatgcacaa ggccgacaat aggcacgagc atagaagtta gtacgtagcg tcgtcgcata    60

<210> SEQ ID NO 122
<211> LENGTH: 59
<212> TYPE: DNA
<213> ORGANISM: Artificial Sequence
<220> FEATURE:
<223> OTHER INFORMATION: aligned read of a synthetic nucleic acid

<400> SEQUENCE: 122
gatgcacaag gccgacaata ggcacgagca tagaagttag tacgtagcgt cgtcgcata    59

<210> SEQ ID NO 123
<211> LENGTH: 59
<212> TYPE: DNA
<213> ORGANISM: Artificial Sequence
<220> FEATURE:
<223> OTHER INFORMATION: aligned read of a synthetic nucleic acid

<400> SEQUENCE: 123
gatgcacaag gccgacaata ggcacgagca tagaagttag tacgtagcgt cgtcgcata    59

<210> SEQ ID NO 124
<211> LENGTH: 60
<212> TYPE: DNA
<213> ORGANISM: Artificial Sequence
<220> FEATURE:
<223> OTHER INFORMATION: aligned read of a synthetic nucleic acid

<400> SEQUENCE: 124
agatgcacaa ggccgacaat aggcacgagc atagaagtta gtacgtagcg tcgtcgcata    60

<210> SEQ ID NO 125
<211> LENGTH: 60
<212> TYPE: DNA
<213> ORGANISM: Artificial Sequence
<220> FEATURE:
<223> OTHER INFORMATION: aligned read of a synthetic nucleic acid

<400> SEQUENCE: 125
agatgcacaa ggccgacaat aggcacgagc atagaagtta gtacgtagcg tcgtcgcata    60

<210> SEQ ID NO 126
<211> LENGTH: 60
<212> TYPE: DNA
<213> ORGANISM: Artificial Sequence
<220> FEATURE:
<223> OTHER INFORMATION: aligned read of a synthetic nucleic acid

<400> SEQUENCE: 126
agccgctcaa gtccgacaat aagcacgagc atagaagcta gtcactatcg tcgtcgcact    60

<210> SEQ ID NO 127
<211> LENGTH: 11
<212> TYPE: DNA
<213> ORGANISM: Artificial Sequence
<220> FEATURE:
<223> OTHER INFORMATION: aligned read of a synthetic nucleic acid

<400> SEQUENCE: 127
agatgcacaa g    11
```

<210> SEQ ID NO 128
<211> LENGTH: 60
<212> TYPE: DNA
<213> ORGANISM: Artificial Sequence
<220> FEATURE:
<223> OTHER INFORMATION: aligned read of a synthetic nucleic acid

<400> SEQUENCE: 128
cgatgcacaa ggccgacaat aggcacgcgc atagaagtta gtacgtagcg tcgtcgcata    60

<210> SEQ ID NO 129
<211> LENGTH: 60
<212> TYPE: DNA
<213> ORGANISM: Artificial Sequence
<220> FEATURE:
<223> OTHER INFORMATION: aligned read of a synthetic nucleic acid

<400> SEQUENCE: 129
agatgcacaa ggccgacaat aggcacgagc atagaagtga gtacgtagcg tcgtcgcata    60

<210> SEQ ID NO 130
<211> LENGTH: 60
<212> TYPE: DNA
<213> ORGANISM: Artificial Sequence
<220> FEATURE:
<223> OTHER INFORMATION: aligned read of a synthetic nucleic acid

<400> SEQUENCE: 130
agatgcacaa ggccgacaat aggcacgagc atagaagtta gtacgtagcg tcgtcgcata    60

<210> SEQ ID NO 131
<211> LENGTH: 60
<212> TYPE: DNA
<213> ORGANISM: Artificial Sequence
<220> FEATURE:
<223> OTHER INFORMATION: aligned read of a synthetic nucleic acid

<400> SEQUENCE: 131
agatgcacaa ggccgacaat aggcacgagc atagaagtta gtacgtagcg tcgtcgcata    60

<210> SEQ ID NO 132
<211> LENGTH: 22
<212> TYPE: DNA
<213> ORGANISM: Artificial Sequence
<220> FEATURE:
<223> OTHER INFORMATION: aligned read of a synthetic nucleic acid

<400> SEQUENCE: 132
agatgcacaa ggccgacaat ag                                              22

<210> SEQ ID NO 133
<211> LENGTH: 30
<212> TYPE: DNA
<213> ORGANISM: Artificial Sequence
<220> FEATURE:
<223> OTHER INFORMATION: aligned read of a synthetic nucleic acid

<400> SEQUENCE: 133
agatgcacaa ggccgacaat aggcacgagc                                      30

<210> SEQ ID NO 134
<211> LENGTH: 20
<212> TYPE: DNA
<213> ORGANISM: Artificial Sequence
<220> FEATURE:
<223> OTHER INFORMATION: aligned read of a synthetic nucleic acid

<400> SEQUENCE: 134
agatgcacaa ggccgacaat                                         20

<210> SEQ ID NO 135
<211> LENGTH: 60
<212> TYPE: DNA
<213> ORGANISM: Artificial Sequence
<220> FEATURE:
<223> OTHER INFORMATION: aligned read of a synthetic nucleic acid

<400> SEQUENCE: 135
agatgcacaa ggccgacaat aggcacgagc atagaagata gtacgtagcg tcgtcgcata     60

<210> SEQ ID NO 136
<211> LENGTH: 60
<212> TYPE: DNA
<213> ORGANISM: Artificial Sequence
<220> FEATURE:
<223> OTHER INFORMATION: aligned read of a synthetic nucleic acid

<400> SEQUENCE: 136
agatgaacaa gacctacaat aggcactagc ataggactta gtccgccgcg tcgtcccata     60

<210> SEQ ID NO 137
<211> LENGTH: 22
<212> TYPE: DNA
<213> ORGANISM: Artificial Sequence
<220> FEATURE:
<223> OTHER INFORMATION: aligned read of a synthetic nucleic acid

<400> SEQUENCE: 137
agatgcacaa ggccgacaac ag                                      22

<210> SEQ ID NO 138
<211> LENGTH: 29
<212> TYPE: DNA
<213> ORGANISM: Artificial Sequence
<220> FEATURE:
<223> OTHER INFORMATION: aligned read of a synthetic nucleic acid

<400> SEQUENCE: 138
agatgcacaa ggccgacaat aggcacgag                               29

<210> SEQ ID NO 139
<211> LENGTH: 17
<212> TYPE: DNA
<213> ORGANISM: Artificial Sequence
<220> FEATURE:
<223> OTHER INFORMATION: aligned read of a synthetic nucleic acid

<400> SEQUENCE: 139
agatgcacaa ggccgac                                            17

<210> SEQ ID NO 140
<211> LENGTH: 40
<212> TYPE: DNA
<213> ORGANISM: Artificial Sequence
<220> FEATURE:
<223> OTHER INFORMATION: aligned read of a synthetic nucleic acid

<400> SEQUENCE: 140
agatgcacaa ggccgacaac aggcacgcat agaagttagt                   40

<210> SEQ ID NO 141

```
<211> LENGTH: 29
<212> TYPE: DNA
<213> ORGANISM: Artificial Sequence
<220> FEATURE:
<223> OTHER INFORMATION: aligned read of a synthetic nucleic acid

<400> SEQUENCE: 141
agctgcacaa ggccgacaat aggcacgag                                      29
```